US006638934B2

(12) United States Patent
Robichaud et al.

(10) Patent No.: US 6,638,934 B2
(45) Date of Patent: Oct. 28, 2003

(54) SUBSTITUTED PYRAZINOQUINOXALINE DERIVATIVES AS SEROTONIN RECEPTOR AGONIST AND ANTAGONISTS LIGANDS

(75) Inventors: Albert Robichaud, Landenberg, PA (US); Ian S. Mitchell, Wilmington, DE (US); Taekyu Lee, Wilmington, DE (US); Wenting Chen, Exton, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 18 days.

(21) Appl. No.: 10/026,404

(22) Filed: Dec. 19, 2001

(65) Prior Publication Data

US 2002/0177596 A1 Nov. 28, 2002

Related U.S. Application Data

(60) Provisional application No. 60/256,765, filed on Dec. 20, 2000.

(51) Int. Cl.⁷ ................. C07D 487/02; A61K 31/5377; A61K 31/541
(52) U.S. Cl. ............. 514/250; 514/211.09; 514/214.02; 514/224.5; 514/229.5; 540/546; 540/578; 544/14; 544/99; 544/343; 544/346
(58) Field of Search ................................ 544/346, 343, 544/99, 14; 540/578, 546; 514/250, 229.5, 224.5, 211.09, 214.02

(56) References Cited

U.S. PATENT DOCUMENTS

| | | | |
|---|---|---|---|
| 3,914,421 A | 10/1975 | Rajagopalan | 424/248 |
| 4,013,652 A | 3/1977 | Rajagopalan | 260/244 R |
| 4,115,577 A | 9/1978 | Rajagopalan | 424/256 |
| 4,183,936 A | 1/1980 | Rajagopalan | 424/256 |
| 4,219,550 A | 8/1980 | Rajagopalan | 424/246 |
| 4,238,607 A | 12/1980 | Rajagopalan | 544/14 |

FOREIGN PATENT DOCUMENTS

| | | |
|---|---|---|
| EP | 0473550 | 8/1991 |
| WO | WO00/35922 | 6/2000 |

OTHER PUBLICATIONS

Arnt, J., "Pharmacological Specificity of Conditioned Avoidance Response Inhibition in Rats: Inhibition by Neuroleptics and Correlation to Dopamine Receptor Blockade", Acta pharmacol. et toxicol., vol. 51, pp. 321–329 (1982).

Hudlocky, Reductions in Organic Chemistry, Ellis Horwood, Ltd., Chichester, UK, 1984.

Batchelor, M.J. et al., "Total Synthesis of Close Analogues of the Immunosuppressant FK506", Tertrahedron, vol. 50, No. 3, pp. 809–826 (1994).

Guram et al., Angew Chem. Int. Ed. Engl., 34, 1348–1350, 1995.

Berendsen, H.H.G. et al., "Involvement of 5–HT$_{1C}$–receptors in drug–induced penile erections in rats", Psychopharmacology, vol. 101, pp. 57–61 (1990).

Berridge, J. et al., "Lithium amplifies agonist–dependent phosphatidylinositol responses in brain and salivary glands", Biochem. J., vol. 206, pp. 587–595 (1982).

Costall, B. et al., "Detection of the Neuroleptic Properties of Clozapine, Sulpiride and Thioridazine", Psychopharmacologia (Berl.), vol. 43, pp. 69–74 (1975).

Larock, Comprehensive Organic Transformations, VCH Publishers, New York, 1989.

Curzon, G. et al., "m–CPP: a tool for studying behavioural responses associated with 5–HT$_{1C}$ receptors", TiPS, vol. 11, pp. 181–182 (1990).

Dike, S.Y. et al., "A New Enantioselective Chemoenzymatic Synthesis of R–(–)Thiazesim Hydrochloride", Bioorganic & Medicinal Chemistry Letters, vol. 1, No. 8, pp. 383–386 (1991).

(List continued on next page.)

Primary Examiner—Deepak Rao
(74) Attorney, Agent, or Firm—Maureen P. O'Brien; Sammy G. Duncan, Jr.

(57) ABSTRACT

The present invention is directed to novel compounds represented by structural Formulas (I) and (I-a):

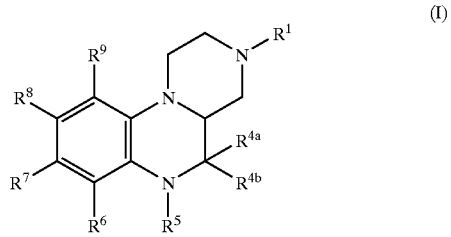

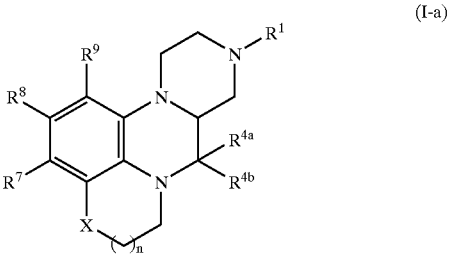

or a pharmaceutically acceptable salt thereof, wherein $R^1$, $R^{4a}$, $R^{4b}$, $R^5$, $R^6$, $R^7$, $R^8$, $R^9$, n, and X are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility.

22 Claims, No Drawings

OTHER PUBLICATIONS

Egan, C.T. et al., "Agonist activity of LSD and lisuride at cloned 5HT$_{2A}$ and 5HT$_{2C}$ receptors", Psychopharmacology, vol. 136, pp. 409–414 (1998).

Fitzgerald, L.W. et al., "High–Affinity Agonist Binding Correlates with Efficacy (Intrinsic Activity) at the Human Serotonin 5–HT$_{2A}$ and 5–HT$_{2C}$ Receptors. . . ", Journal of Neurochemistry, vol. 72, No. 5, pp. 2127–2134 (1999).

Frost, J.J. et al., "In Vivo Binding of $^3$H–N–Methylspiperone to Dopamine and Serotonin Receptors", Life Sciences, vol. 40, pp. 987–995 (1987).

Glennon, R.A. et al., "[$^{125}$]–1–(2, 5–Dimethoxy–4–iodophenyl)–2–amino–propane: An Iodinated Radioligand That Specifically Labels the Agonist High–Affinity State of 5–HT$_2$ Serotonin Receptors", J. Med. Chem., vol. 31, pp. 5–7 (1988).

Kinbara et al., Journal of the Chemical Society, Perkin Trans. 2, 2615–2622, 1996.

Horlick, R.A. et al., "Rapid Generation of Stable Cell Lines Expressing Corticotropin–Releasing Hormone Receptor for Drug Discovery", Protein Expression and Purification, vol. 9, pp. 301–308 (1997).

House, H.O., Modern Synthetic Reactions, 2nd ed., W.A. Benjamin, Inc. (table of contents) (1972).

Ismaiel, A.M. et al., "Binding of N$_2$–Substituted Pyrido[4, 3–b]Indole Analogs of Spiperone at Human 5–HT2A, 5–HT2B, and 5HT2C Serotonin Receptors", Med. Chem. Res., pp. 197–211 (1996).

Tomori et al., Bull Chem. Soc. Japan, 69, 3581–3590, 1996.

Greene et al., "Protective Groups in Organic Synthesis", 2$^{nd}$ Edition, John Wiley and Sons, Inc., New York, pp. 309–405, 1991.

Koek, W. et al., "Behavioral Pharmacology of Antagonists at 5–HT$_2$/5–HT$_{1C}$ Receptors", Neuroscience & Biobehavioral Reviews, vol. 16, pp. 95–105 (1992).

Leonard, B.E., "The Comparative Pharmacology of New Antidepressants", J. Clin. Psychiatry, vol. 54, No. 8 (suppl.), pp. 3–15 (1993), and vol. 54, No. 12, p. 491 (1993) (correction).

Leonhardt, S. et al., "Molecular Pharmacological Differences in the Interaction of Serotonin with 5–Hydroxytryptamine$_{1C}$ and 5–Hydroxytryptamine$_2$ Receptors", Molecular Pharmacology, vol. 42, pp. 328–335 (1992).

Lucaites, V.L. et al., "Receptor Subtype and Density Determine the Coupling Repertoire of the 5–HT$_2$ Receptor Subfamily", Life Sciences, vol. 59, No. 13, pp. 1081–1095 (1996).

Lucki, I. et al., "Differential Actions of Serotonin Antagonists on Two Behavioral Models of Serotonin Receptor Activation in the Rat", The Journal of Pharmacology and Experimental Therapeutics, vol. 228, No. 1, pp. 133–139 (1984).

Miyaura, N. et al., "Palladium–Catalyzed Cross–Coupling Reactions of Organoboron Compounds", Chem. Rev., vol. 95, pp. 2457–2483 (1995).

Kharasch, J. Organic Chemistry, 1903–1905, 1963.

Buchwald et al., J. Am. Chem. Soc., 9722–9723, 1998.

Stille et al., J. Am. Chem. Soc., 7500–7506, 1984.

Thompson et al., Chem. Rev., 96 (1), 555–600, 1996.

Olah, G.A., Friedel–Crafts and Related Reactions, Interscience Publishers, a division of John Wiley & Sons Inc., vol. III, Part 1, pp. xi–xxvi (1964).

Olah, G.A., Friedel–Crafts Chemistry, John Wiley & Sons, Inc. (table of contents) (1973).

Sibi, M.P. et al., "N,N'–Dimethoxy–N,N'–Dimethylethanediamide: A Useful α–Oxo–N–Methoxy–N–Methylamide and 1,2–Diketone Synthon", Tetrahedron Letters, vol. 33, No. 15, pp. 1941–1944 (1992).

Smith, P.A.S., "The Schmidt Reaction: Experimental Conditions and Mechanism", J. Am. Chem. Soc., vol. 70, pp. 320–323 (1948).

Stanforth, S.P., "Catalytic Cross–coupling Reactions in Biaryl Synthesis", Tetrahedron, vol. 54, pp. 263–303 (1998).

Tsuji, J., Palladium Reagents and Catalysts, Innovations in Organic Synthesis, John Wiley & Sons Ltd., pp. v–ix (1995).

Ugedo, L. et al., "Ritanserin, a 5–HT$_2$ receptor antagonist, activates midbrain dopamine neurons by blocking serotonergic inhibition", Psychopharmacology, vol. 98, pp. 45–50 (1989).

SUBSTITUTED PYRAZINOQUINOXALINE DERIVATIVES AS SEROTONIN RECEPTOR AGONIST AND ANTAGONISTS LIGANDS

This application claims the benefit of provisional application 60/256,765 filed Dec. 20, 2000.

FIELD OF THE INVENTION

The present invention is directed to novel compounds represented by structural Formulas (I) and (I-a):

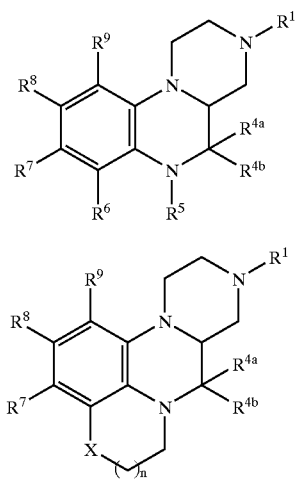

or a pharmaceutically acceptable salt thereof, wherein $R^1$, $R^{4a}$, $R^{4b}$, $R^5$, $R^6$, $R^7$, $R^8$, $R^9$, n, and X are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility.

BACKGROUND OF THE INVENTION

There exists a substantial correlation for the relationship between 5-HT2 receptor modulation and a variety of diseases and therapies. To date, three subtypes of the 5-HT2 receptor class have been identified, 5-HT2A, 5-HT2B, and 5-HT2C. Prior to the early 1990's the 5-HT2C and 5-HT2A receptors were referred to as 5-HT1C and 5-HT2, respectively.

The agonism or antagonism of 5-HT2 receptors, either selectively or nonselectively, has been associated with the treatment of various central nervous system (CNS) disorders. Ligands possessing affinity for the 5-HT2 receptors have been shown to have numerous physiological and behavioral effects (Trends in Pharmacological Sciences, 11, 181, 1990). In the recent past the contribution of serotonergic activity to the mode of action of antidepressant drugs has been well documented. Compounds that increase the overall basal tone of serotonin in the CNS have been successfully developed as antidepressants. The serotonin selective reuptake inhibitors (SSRI) function by increasing the amount of serotonin present in the nerve synapse. These breakthrough treatments, however, are not without side effects and suffer from delayed onset of action (Leonard, J. Clin. Psychiatry, 54(suppl), 3, 1993). Due to the mechanism of action of the SSRIs, they effect the activity of a number of serotonin receptor subtypes. This non-specific modulation of the serotonin family of receptors most likely plays a significant role in the side effect profile. In addition, these compounds often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

There is ample evidence to support the role of selective 5-HT2 receptor ligands in a number of disease therapies. Modulation of 5-HT2 receptors has been associated with the treatment of schizophrenia and psychoses (Ugedo, L., et.al., Psychopharmacology, 98, 45, 1989). Mood, behavior and hallucinogenesis can be affected by 5-HT2 receptors in the limbic system and cerebral cortex. 5-HT2 receptor modulation in the hypothalamus can influence appetite, thermoregulation, sleep, sexual behavior, motor activity, and neuroendocrine function (Hartig, P., et.al., Annals New York Academy of Science, 149, 159). There is also evidence indicating that 5-HT2 receptors mediate hypoactivity, effect feeding in rats, and mediate penile erections (Pyschopharmacology, 101, 57, 1990).

Compounds exhibiting selectivity for the 5-HT2B receptor are useful in treating conditions such as tachygastria, hypermotility associated with irritable bowel disorder, constipation, dyspepsia, and other peripherally mediated conditions.

5-HT2A antagonists have been shown to be effective in the treatment of schizophrenia, anxiety, depression, and migraines (Koek, W., Neuroscience and Behavioral reviews, 16, 95, 1996). Aside from the beneficial antipsychotic effects, classical neuroleptic are frequently responsible for eliciting acute extrapyramidal side effects and neuroendocrine disturbances. These compounds generally possess signifcant dopamine D2 receptor affinity (as well as other nuisance receptor affinity) which frequently is associated with extra pyramidal symptoms and tardive dyskinesia, thus detracting from their efficacy as front line treatments in schizophrenia and related disorders. Compounds possessing a more favorable selectivity profile would represent a possible improvement for the treatment of CNS disorders.

U.S. Pat. Nos. 3,914,421; 4,013,652; 4,115,577; 4,183,936; and 4,238,607 disclose pyridopyrrolobenzheterocycles of formula:

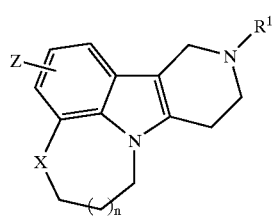

where X is O, S, S(=O), or $SO_2$; n is 0 or 1; $R^1$ is various carbon substituents, and Z is a monosubstituent of H, methyl, or chloro.

U.S. Pat. No. 4,219,550 discloses pyridopyrrolobenzheterocycles of formula:

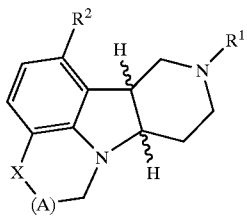

where X is O or S; $R^1$ is $C_{1-4}$ alkyl or cyclopropyl; $R^2$ is H, $CH_3$, $OCH_3$, Cl, Br, F, or $CF_3$; and (A) is —$CH_2$—, —$CH(CH_3)$—, or —$CH_2CH_2$—.

European Patent Application EP 473,550 A1 discloses indolonaphthyridines of formula:

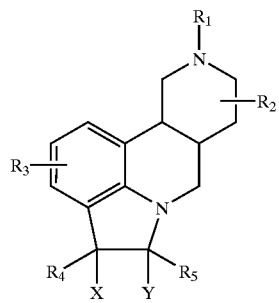

wherein X and Y are H or a simple ring, $R^1$, is H, alkyl, alkylcarbonylalkyl, arylcarbonylalkyl, aralkyl, or a mono or disubstituted carbamoylalkyl; and $R^3$, $R^4$, and $R^5$ are H, halogen, alkyl, alkoxy, alkylthio or trifluoromethyl.

PCT International Patent Application WO 00/35922 discloses tetrahydro-1H-pyrazino(1,2-A-quinoxalin-5(6H)one derivatives of formula:

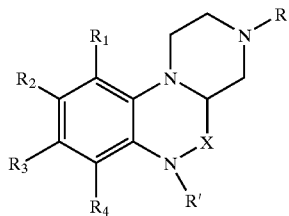

as being 5HT2C agonists; wherein X is CR5R6 or carbonyl; R is H or alkyl; R' is H, alkyl, acyl, or aroyl; and R1, R2, R3, and R4 are independently, H, alkyl, alkoxy, halogen, trifluoroalkyl, cyano, alkylsulfonamide, alkyl amide, amino, alkylamino, dialkylamino, trifluoroalkoxy, acyl, or aroyl.

None of the above references suggest or disclose the compounds of the present invention.

There remains a need to discover new compounds useful as serotonin agonists and antagonists which are useful in the control or prevention of central nervous system disorders. As such, the present invention discloses novel compounds which are of low molecular weight, useful as serotonin agonists and antagonists, and provide good in vitro potency.

SUMMARY OF THE INVENTION

One object of the present invention is to provide novel compounds which are useful as agonists or antagonists of 5-HT2 receptors, more specifically 5-HT2A and 5-HT2C receptors, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility comprising administering to a host in need of such treatment a therapeutically effective amount of at least one of the compounds of the present invention or a pharmaceutically acceptable salt or prodrug form thereof. More specifically, the present invention provides a method for treating obesity anxiety, depression, or schizophrenia.

These and other objects, which will become apparent during the following detailed description, have been achieved by the inventors' discovery that compounds of Formula (I):

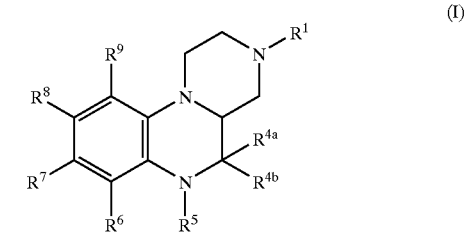

(I)

or pharmaceutically acceptable salt or prodrug forms thereof, wherein $R^1$, $R^{4a}$, $R^{4b}$, $R^5$, $R^6$, $R^7$, $R^8$, and $R^9$ are defined below, are effective agonists or antagonists of 5-HT2 receptors.

DETAILED DESCRIPTION OF THE EMBODIMENTS

Thus, in a first embodiment, the present invention provides a novel compound of Formula (I):

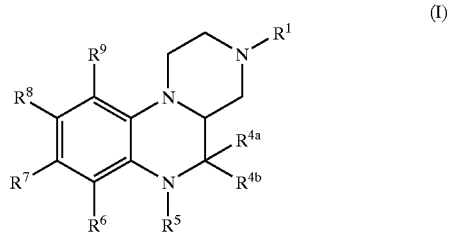

(I)

or a stereoisomer or a pharmaceutically acceptable salt form thereof, wherein:
$R^1$ is selected from
H,
C(=O)$R^2$,
C(=O) O$R^2$,
$C_{1-8}$ alkyl,
$C_{2-8}$ alkenyl,
$C_{2-8}$ alkynyl,
$C_{3-7}$ cycloalkyl,
$C_{1-6}$ alkyl substituted with Z, $C_{2-6}$ alkenyl substituted with Z,
$C_{2-6}$ alkynyl substituted with Z,
$C_{3-6}$ alkyl substituted with Z,
aryl substituted with Z,
5–6 membered heterocyclic ring system containing at least one heteroatom selected from the group consisting of N, O, and S, said heterocyclic ring system substituted with Z;
$C_{1-3}$ alkyl substituted with Y,
$C_{2-3}$ alkenyl substituted with Y,
$C_{2-3}$ alkynyl substituted with Y,
$C_{1-6}$ alkyl substituted with 0–2 $R^2$,
$C_{2-6}$ alkenyl substituted with 0–2 $R^2$,
$C_{2-6}$ alkynyl substituted with 0–2 $R^2$,
aryl substituted with 0–2 $R^2$, and
5–6 membered heterocyclic ring system containing at least one heteroatom selected from the group consisting of N, O, and S, said heterocyclic ring system substituted with 0–2 $R^2$;

Y is selected from
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{3-6}$ cycloalkyl substituted with —($C_{1-3}$ alkyl)-Z,
aryl substituted with —($C_{1-3}$ alkyl)-Z, and
5–6 membered heterocyclic ring system containing at least one heteroatom selected from the group consisting of N, O, and S, said heterocyclic ring system substituted with —($C_{1-3}$ alkyl)-Z;

Z is selected from H,
—CH(OH)$R^2$,
—C(ethylenedioxy)$R^2$,
—O$R^2$,
—S$R^2$,
—N$R^2R^3$,
—C(O)$R^2$,
—C(O)N$R^2R^3$,
—N$R^3$C(O)$R^2$,
—C(O) O$R^2$,
—OC(O)$R^2$,
—CH(=N$R^4$)N$R^2R^3$,
—NHC(=N$R^4$)N$R^2R^3$,
—S(O)$R^2$,
—S(O)$_2R^2$,
—S(O)$_2$N$R^2R^3$, and —N$R^3$S(O)$_2R^2$;

$R^2$, at each occurrence, is independently selected from
halo,
$C_{1-3}$ haloalkyl,
$C_{1-4}$ alkyl,
$C_{2-4}$ alkenyl,
$C_{2-4}$ alkynyl,
$C_{3-6}$ cycloalkyl,
aryl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;
alternatively, $R^2$ and $R^3$ join to form a 5- or 6-membered ring optionally substituted with —O— or —N($R^4$)—;
$R^4$, at each occurrence, is independently selected from H and $C_{1-4}$ alkyl;
$R^{4a}$ is H or $C_{1-4}$ alkyl;
$R^{4b}$ is H;
alternatively, $R^{4a}$ and $R^{4b}$ are taken together to form =O or =S;
$R^5$ is H or $C_{1-4}$ alkyl;
$R^6$ is H or $C_{1-4}$ alkyl;
alternatively, $R^5$ and $R^6$ are taken together to form a fused heterocyclic ring of formula:

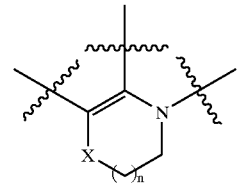

wherein:
X is a bond, —CH$_2$—, —O—, —S—, —S(=O)—, —S(=O)$_2$—,
—NR$^{10}$—, —CH$_2$CH$_2$—, —OCH$_2$—, —SCH$_2$—, —CH$_2$O—, —CH$_2$S—,
—CH$_2$NR$^{10}$—, —NR$^{10}$CH$_2$—, —NHC(=O)—, or —C(=O)NH—; and
n is 1 or 2;
$R^7$ and $R^9$, at each occurrence, are independently selected from
H, halo, —CF$_3$, —OCF$_3$, —OH, —CN, —NO$_2$, —NR$^{46}R^{47}$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
OR$^{12}$, SR$^{12}$, NR$^{12}R^{13}$, C(O)H, C(O)R$^{12}$, C(O)NR$^{12}R^{13}$, NR$^{14}$C(O)R$^{12}$, C(O)OR$^{12}$, OC(O)R$^{12}$, OC(O)OR$^{12}$,
CH(=NR$^{14}$)NR$^{12}R^{13}$, NHC(=NR$^{14}$)NR$^{12}R^{13}$, S(O)R$^{12}$, S(O)$_2R^{12}$,
S(O)NR$^{12}R^{13}$, S(O)$_2$NR$^{12}R^{13}$, NR$^{14}$S(O)R$^{12}$, NR$^{14}$S(O)$_2R^{12}$,
NR$^{12}$C(O)R$^{15}$, NR$^{12}$C(O)OR$^{15}$, NR$^{12}$S(O)$_2R^{15}$, and NR$^{12}$C(O) NHR$^{15}$;
$R^8$ is selected from
H, halo, —CF$_3$, —OCF$_3$, —OH, —CN, —NO$_2$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{10}$ is selected from H, $C_{1-4}$ alkyl substituted with 0–2 $R^{10A}$, $C_{2-4}$ alkenyl substituted with 0–2 $R^{10A}$, $C_{2-4}$ alkynyl substituted with 0–1 $R^{10A}$, and $C_{1-4}$ alkoxy;

$R^{10A}$ is selected from $C_{1-4}$ alkoxy, $C_{3-6}$ carbocyclic residue substituted with 0–3 $R^{33}$, phenyl substituted with 0–3 $R^{33}$, and 5–6 membered heterocyclic ring system containing 1, 2, or 3 heteroatoms selected from the group consisting of N, O, and S; substituted with 0–2 $R^{44}$;

$R^{11}$ is selected from

H, halo, $-CF_3$, $-CN$, $-NO_2$, $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, aryl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with $-O-$ or $-N(R^{14})-$;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$, $SO_2R^{45}$, $NR^{46}R^{47}$, $-C(=O)H$, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{31}$, at each occurrence, is independently selected from H, OH, halo, $CF_3$, $SO_2R^{45}$, $NR^{46}R^{47}$, and $C_{1-4}$ alkyl;

$R^{33}$, at each occurrence, is independently selected from

H, OH, halo, CN, $NO_2$, $CF_3$, $SO_2R^{45}$, $NR^{46}R^{47}$, $-C(=O)H$, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-$C(=O)-$, $C_{1-4}$ alkyl-$C(=O)NH-$, $C_{1-4}$ alkyl-$OC(=O)-$, $C_{1-4}$ alkyl-$C(=O)O-$, $C_{3-6}$ cycloalkyl-oxy-, $C_{3-6}$ cycloalkylmethyl-oxy-;

$C_{1-6}$ alkyl substituted with OH, methoxy, ethoxy, propoxy, butoxy, $-SO_2R^{45}$, $-NR^{46}R^{47}$, $NR^{46}R^{47}C(=O)-$, or $(C_{1-4}\text{ alkyl})CO_2-$; and $C_{2-6}$ alkenyl substituted with OH, methoxy, ethoxy, propoxy, butoxy, $-SO_2R^{45}$, $-NR^{46}R^{47}$, $NR^{46}R^{47}C(=O)-$, or $(C_{1-4}\text{ alkyl})CO_2-$;

$R^{41}$, at each occurrence, is independently selected from

H, $CF_3$, halo, OH, $CO_2H$, $SO_2R^{45}$, $NR^{46}R^{47}$, $NO_2$, CN, $=O$;

$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from

H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, $CH(=NH)NH_2$, $NHC(=NH)NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, $-OH$, $NR^{46}R^{47}$, $CO_2H$, $SO_2R^{45}$, $-CF_3$, $-OCF_3$, $-CN$, $-NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl; and $R^{47}$, at each occurrence, is independently selected from H, $C_{1-4}$ alkyl, $-C(=O)NH(C_{1-4}\text{ alkyl})$, $-SO_2(C_{1-4}\text{ alkyl})$, $-C(=O)O(C_{1-4}\text{ alkyl})$, $-C(=O)(C_{1-4}\text{ alkyl})$, and $-C(=O)H$;

provided when $R^5$ is H or $C_{1-4}$ alkyl; and $R^6$ is H or $C_{1-4}$ alkyl; then at least one of $R^7$, $R^8$ and $R^9$ must be either 1)

an aryl group substituted with 1–5 $R^{33}$; 2) an arylmethyl-group substituted with 1–5 $R^{33}$; or 3) —$NR^{12}R^{13}$ wherein $R^{12}$ is an aryl group substituted with 1–5 $R^{33}$.

[2] In another embodiment, the present invention provides a novel compound of Formula (I) wherein:

$R^1$ is selected from
- H,
- C(=O)$R^2$,
- C(=O)O$R^2$,
- $C_{1-8}$ alkyl,
- $C_{2-8}$ alkenyl,
- $C_{2-8}$ alkynyl,
- $C_{3-7}$ cycloalkyl,
- $C_{1-6}$ alkyl substituted with 0–2 $R^2$,
- $C_{2-6}$ alkenyl substituted with 0–2 $R^2$,
- $C_{2-6}$ alkynyl substituted with 0–2 $R^2$,
- aryl substituted with 0–2 $R^2$, and
- 5–6 membered heterocyclic ring system containing at least one heteroatom selected from the group consisting of N, O, and S, said heterocyclic ring system substituted with 0–2 $R^2$;

$R^2$, at each occurrence, is independently selected from
- F, Cl, $CH_2F$, $CHF_2$, $CF_3$,
- $C_{1-4}$ alkyl,
- $C_{2-4}$ alkenyl,
- $C_{2-4}$ alkynyl,
- $C_{3-6}$ cycloalkyl,
- phenyl substituted with 0–5 $R^{42}$;
- $C_{3-10}$ carbocyclic residue substituted with 0–3 $R^{41}$, and
- 5–10 membered heterocyclic ring system containing from 1–4 heteroatoms selected from the group consisting of N, O, and S substituted with 0–3 $R^{41}$;

$R^{4a}$ is H or $C_{1-4}$ alkyl;
$R^{4b}$ is H;
alternatively, $R^{4a}$ and $R^{4b}$ are taken together to form =O or =S;
$R^5$ is H or $C_{1-4}$ alkyl;
$R^6$ is H or $C_{1-4}$ alkyl;
$R^7$ is selected from
- H, F, Cl, —$CF_3$, —$OCF_3$, —OH, —CN, —$NO_2$, $NR^{12}R^{13}$,
- $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
- methyl substituted with $R^{11}$;
- $C_{3-6}$ carbocyclic residue substituted with 0–3 $R^{33}$; and
- aryl substituted with 0–5 $R^{33}$;

$R^8$ is selected from
- H, F, Cl, —$CF_3$, —$OCF_3$, —OH, —CN, —$NO_2$, $NR^{12}R^{13}$,
- $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
- methyl substituted with $R^{11}$;
- $C_{3-6}$ carbocyclic residue substituted with 0–3 $R^{33}$; and
- aryl substituted with 0–5 $R^{33}$;

$R^9$ is selected from
- H, F, Cl, —$CF_3$, —$OCF_3$, —OH, —CN, —$NO_2$,
- $C_{1-8}$ alkyl, $C_{2-8}$ alkenyl, $C_{2-8}$ alkynyl, $C_{1-4}$ haloalkyl, $C_{1-8}$ alkoxy, and ($C_{1-4}$ haloalkyl)oxy;

$R^{11}$ is aryl substituted with 0–5 $R^{33}$,
$R^{12}$ is aryl substituted with 0–5 $R^{33}$,
$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl; $R^{16}$, at each occurrence, is independently selected from H, OH, halo, CN, $NO_2$, $CF_3$, $SO_2R^{45}$, $NR^{46}R^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{33}$, at each occurrence, is independently selected from
- H, OH, halo, CN, $NO_2$, $CF_3$, $SO_2R^{45}$, $NR^{46}R^{47}$, —C(=O)H,
- phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;
- $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and
- $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{41}$, at each occurrence, is independently selected from
- H, $CF_3$, halo, OH, $CO_2H$, $SO_2R^{45}$, $NR^{46}R^{47}$, $NO_2$, CN, =O;
- $C_{2-8}$ alkenyl, $C_{2-8}$ alkynyl, $C_{1-4}$ alkoxy, $C_{1-4}$ haloalkyl
- $C_{1-4}$ alkyl substituted with 0–1 $R^{43}$,
- aryl substituted with 0–3 $R^{42}$, and
- 5–10 membered heterocyclic ring system containing from 1–4 heteroatoms selected from the group consisting of N, O, and S substituted with 0–3 $R^{44}$;

$R^{42}$, at each occurrence, is independently selected from
- H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, CH(=NH)$NH_2$, NHC(=NH)$NH_2$,
- $C_{2-6}$ alkenyl, $C_{2-6}$ alkynyl, $C_{1-4}$ alkoxy, $C_{1-4}$ haloalkyl, $C_{3-6}$ cycloalkyl,
- $C_{1-4}$ alkyl substituted with 0–1 $R^{43}$,
- aryl substituted with 0–3 $R^{44}$, and
- 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;
$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;
$R^{45}$ is $C_{1-4}$ alkyl;
$R^{46}$, at each occurrence, is independently selected from H and $C_{1-4}$ alkyl; and
$R^{47}$, at each occurrence, is independently selected from H, $C_{1-4}$ alkyl, —C(=O)NH($C_{1-4}$ alkyl), —$SO_2$($C_{1-4}$ alkyl), —C(=O)O($C_{1-4}$ alkyl), —C(=O)($C_{1-4}$ alkyl), and —C(=O)H;

provided at least one of $R^7$ or $R^8$ must be either 1) an aryl group substituted with 1–5 $R^{33}$; 2) an arylmethyl-group substituted with 1–5 $R^{33}$; or 3) —$NR^{12}R^{13}$ wherein $R^{12}$ is an aryl group substituted with 1–5 $R^{33}$.

[3] In another embodiment, the present invention provides a novel compound of Formula (I) wherein:

$R^1$ is selected from H,
  $C_{1-5}$ alkyl substituted with 0–1 $R^2$,
  $C_{2-5}$ alkenyl substituted with 0–1 $R^2$, and
  $C_{2-3}$ alkynyl substituted with 0–1 $R^2$;

$R^2$ is $C_{3-6}$ cycloalkyl;

$R^{4a}$ is H;

$R^{4b}$ is H;

$R^7$ is selected from
  H, F, Cl, —CH$_3$, —OCH$_3$, —CF$_3$, —OCF$_3$, —CN, —NO$_2$, NR$^{12}$R$^{13}$, R$^{11}$;
  methyl substituted with R$^{11}$; and
  phenyl substituted with 0–2 R$^{33}$;

$R^8$ is selected from
  H, F, Cl, —CH$_3$, —OCH$_3$, —CF$_3$, —OCF$_3$, —CN, —NO$_2$, NR$^{12}$R$^{13}$, R$^{11}$;
  methyl substituted with R$^{11}$; and
  phenyl substituted with 0–2 R$^{33}$;

$R^9$ is selected from
  H, F, Cl, —CH$_3$, —OCH$_3$, —CF$_3$, —OCF$_3$, —CN, and —NO$_2$;

$R^{11}$ is selected from
  phenyl-substituted with 0–5 fluoro;
  naphthyl-substituted with 0–3 R$^{33}$;
  2-(H$_3$CCH$_2$C(=O)-phenyl-substituted with R$^{33}$;
  2-(H$_3$CC(=O))-phenyl-substituted with R$^{33}$;
  2-(HC(=O))-phenyl-substituted with R$^{33}$;
  2-(H$_3$CCH(OH))-phenyl-substituted with R$^{33}$;
  2-(H$_3$CCH$_2$CH(OH))-phenyl-substituted with R$^{33}$;
  2-(HOCH$_2$)-phenyl-substituted with R$^{33}$;
  2-(HOCH$_2$CH$_2$)-phenyl-substituted with R$^{33}$;
  2-(H$_3$COCH$_2$)-phenyl-substituted with R$^{33}$;
  2-(H$_3$COCH$_2$CH$_2$)-phenyl-substituted with R$^{33}$;
  2-(H$_3$CCH(OMe))-phenyl-substituted with R$^{33}$;
  2-(H$_3$COC(=O))-phenyl-substituted with R$^{33}$;
  2-(HOCH$_2$CH=CH)-phenyl-substituted with R$^{33}$;
  2-((MeOC=O)CH=CH)-phenyl-substituted with R$^{33}$;
  2-(methyl)-phenyl-substituted with R$^{33}$;
  2-(ethyl)-phenyl-substituted with R$^{33}$;
  2-(i-propyl)-phenyl-substituted with R$^{33}$;
  2-(F$_3$C)-phenyl-substituted with R$^{33}$;
  2-(NC)-phenyl-substituted with R$^{33}$;
  2-(H$_3$CO)-phenyl-substituted with R$^{33}$;
  2-(fluoro)-phenyl-substituted with R$^{33}$;
  2-(chloro)-phenyl-substituted with R$^{33}$;
  3-(NC)-phenyl-substituted with R$^{33}$;
  3-(H$_3$CO)-phenyl-substituted with R$^{33}$;
  3-(fluoro)-phenyl-substituted with R$^{33}$;
  3-(chloro)-phenyl-substituted with R$^{33}$;
  4-(NC)-phenyl-substituted with R$^{33}$;
  4-(fluoro)-phenyl-substituted with R$^{33}$;
  4-(chloro)-phenyl-substituted with R$^{33}$;
  4-(H$_3$CS)-phenyl-substituted with R$^{33}$;
  4-(H$_3$CO)-phenyl-substituted with R$^{33}$;
  4-(ethoxy)-phenyl-substituted with R$^{33}$;
  4-(i-propoxy)-phenyl-substituted with R$^{33}$;
  4-(i-butoxy)-phenyl-substituted with R$^{33}$;
  4-(H$_3$CCH$_2$CH$_2$C(=O))-phenyl-substituted with R$^{33}$;
  4-((H$_3$C)$_2$CHC(=O))-phenyl-substituted with R$^{33}$;
  4-(H$_3$CCH$_2$C(=O))-phenyl-substituted with R$^{33}$;
  4-(H$_3$CC(=O))-phenyl-substituted with R$^{33}$;
  4-(H$_3$CCH$_2$CH$_2$CH(OH))-phenyl-substituted with R$^{33}$;
  4-((H$_3$C)$_2$CHCH(OH))-phenyl-substituted with R$^{33}$;
  4-(H$_3$CCH$_2$CH(OH))-phenyl-substituted with R$^{33}$;
  4-(H$_3$CCH(OH))-phenyl-substituted with R$^{33}$;
  4-(cyclopropyloxy)-phenyl-substituted with R$^{33}$;
  4-(cyclobutyloxy)-phenyl-substituted with R$^{33}$; and
  4-(cyclopentyloxy)-phenyl-substituted with R$^{33}$;

$R^{12}$ is selected from
  phenyl-substituted with 0–5 fluoro;
  naphthyl-substituted with 0–3 R$^{33}$;
  2-(H$_3$CCH$_2$C(=O))-phenyl-substituted with R$^{33}$;
  2-(H$_3$CC(=O))-phenyl-substituted with R$^{33}$;
  2-(HC(=O))-phenyl-substituted with R$^{33}$;
  2-(H$_3$CCH(OH))-phenyl-substituted with R$^{33}$;
  2-(H$_3$CCH$_2$CH(OH))-phenyl-substituted with R$^{33}$;
  2-(HOCH$_2$)-phenyl-substituted with R$^{33}$;
  2-(HOCH$_2$CH$_2$)-phenyl-substituted with R$^{33}$;
  2-(H$_3$COCH$_2$)-phenyl-substituted with R$^{33}$;
  2-(H$_3$COCH$_2$CH$_2$)-phenyl-substituted with R$^{33}$;
  2-(H$_3$CCH(OMe))-phenyl-substituted with R$^{33}$;
  2-(H$_3$COC(=O))-phenyl-substituted with R$^{33}$;
  2-(HOCH$_2$CH=CH)-phenyl-substituted with R$^{33}$;
  2-((MeOC=O)CH=CH)-phenyl-substituted with R$^{33}$;
  2-(methyl)-phenyl-substituted with R$^{33}$;
  2-(ethyl)-phenyl-substituted with R$^{33}$;
  2-(i-propyl)-phenyl-substituted with R$^{33}$;
  2-(F$_3$C)-phenyl-substituted with R$^{33}$;
  2-(NC)-phenyl-substituted with R$^{33}$;
  2-(H$_3$CO)-phenyl-substituted with R$^{33}$;
  2-(fluoro)-phenyl-substituted with R$^{33}$;
  2-(chloro)-phenyl-substituted with R$^{33}$;
  3-(NC)-phenyl-substituted with R$^{33}$;
  3-(H$_3$CO)-phenyl-substituted with R$^{33}$;
  3-(fluoro)-phenyl-substituted with R$^{33}$;
  3-(chloro)-phenyl-substituted with R$^{33}$;
  4-(NC)-phenyl-substituted with R$^{33}$;
  4-(fluoro)-phenyl-substituted with R$^{33}$;
  4-(chloro)-phenyl-substituted with R$^{33}$;
  4-(H$_3$CS)-phenyl-substituted with R$^{33}$;
  4-(H$_3$CO)-phenyl-substituted with R$^{33}$;
  4-(ethoxy)-phenyl-substituted with R$^{33}$;
  4-(i-propoxy)-phenyl-substituted with R$^{33}$;
  4-(i-butoxy)-phenyl-substituted with R$^{33}$;
  4-(H$_3$CCH$_2$CH$_2$C(=O))-phenyl-substituted with R$^{33}$;
  4-((H$_3$C)$_2$CHC(=O))-phenyl-substituted with R$^{33}$;
  4-(H$_3$CCH$_2$C(=O))-phenyl-substituted with R$^{33}$;
  4-(H$_3$CC(=O))-phenyl-substituted with R$^{33}$;
  4-(H$_3$CCH$_2$CH$_2$CH(OH))-phenyl-substituted with R$^{33}$;
  4-((H$_3$C)$_2$CHCH(OH))-phenyl-substituted with R$^{33}$;
  4-(H$_3$CCH$_2$CH(OH))-phenyl-substituted with R$^{33}$;
  4-(H$_3$CCH(OH))-phenyl-substituted with R$^{33}$;
  4-(cyclopropyloxy)-phenyl-substituted with R$^{33}$;
  4-(cyclobutyloxy)-phenyl-substituted with R$^{33}$; and 4-(cyclopentyloxy)-phenyl-substituted with $R^{33}$;

$R^{13}$ is H, methyl, or ethyl;

alternatively, $R^{12}$ and R13 join to form a 5- or 6-membered ring selected from pyrrolyl, pyrrolidinyl, imidazolyl, piperidinyl, piperizinyl, methylpiperizinyl,and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy; and $R^{33}$, at each occurrence, is independently selected from H, F, Cl, —$CH_3$, —$OCH_3$, —$CF_3$, —$OCF_3$, —CN, and —$NO_2$.

provided at least one of $R^7$ or $R^8$ must be either 1) an aryl group substituted with 1–5 $R^{33}$; 2) an arylmethyl-group substituted with 1–5 $R^{33}$; or 3) —$NR^{12}R^{13}$ wherein $R^{12}$ is an aryl group substituted with 1–5 $R^{33}$.

[4] In another embodiment, the present invention provides a novel compound of Formula (I) wherein:

$R^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, —CH=$CH_2$, —$CH_2$—CH=$CH_2$, —CH=CH—$CH_3$, —C≡CH, —C≡C—$CH_3$, and —$CH_2$—C≡CH;

$R^{4a}$ is H;

$R^{4b}$ is H;

alternatively, $R^{4a}$ and $R^{4b}$ are taken together to form =O;

$R^7$ is selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;

$R^8$ is selected from 2-chlorophenyl, 2-fluorophenyl, 2-bromophenyl, 2-cyanophenyl, 2-methylphenyl, 2-trifluoromethylphenyl, 2-methoxyphenyl, 2-trifluoromethoxyphenyl, 3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl, 4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl, 2,3-dichlorophenyl, 2,3-difluorophenyl, 2,3-dimethylphenyl, 2,3-ditrifluoromethylphenyl, 2,3-dimethoxyphenyl, 2,3-ditrifluoromethoxyphenyl, 2,4-dichlorophenyl, 2,4-difluorophenyl, 2,4-dimethylphenyl, 2,4-ditrifluoromethylphenyl, 2,4-dimethoxyphenyl, 2,4-ditrifluoromethoxyphenyl, 2,5-dichlorophenyl, 2,5-difluorophenyl, 2,5-dimethylphenyl, 2,5-ditrifluoromethylphenyl, 2,5-dimethoxyphenyl, 2,5-ditrifluoromethoxyphenyl, 2,6-dichlorophenyl, 2,6-difluorophenyl, 2,6-dimethylphenyl, 2,6-ditrifluoromethylphenyl, 2,6-dimethoxyphenyl, 2,6-ditrifluoromethoxyphenyl, 3,4-dichlorophenyl, 3,4-difluorophenyl, 3,4-dimethylphenyl, 3,4-ditrifluoromethylphenyl, 3,4-dimethoxyphenyl, 3,4-ditrifluoromethoxyphenyl, 2,4,6-trichlorophenyl, 2,4,6-trifluorophenyl, 2,4,6-trimethylphenyl, 2,4,6-tritrifluoromethylphenyl, 2,4,6-trimethoxyphenyl, 2,4,6-tritrifluoromethoxyphenyl, 2-chloro-4-$CF_3$-phenyl, 2-fluoro-3-chloro-phenyl, 2-chloro-4-$CF_3$-phenyl, 2-chloro-4-methoxy-phenyl, 2-methoxy-4-isopropyl-phenyl, 2-$CF_3$-4-methoxy-phenyl, 2-methyl-4-methoxy-5-fluoro-phenyl, 2-methyl-4-methoxy-phenyl, 2-chloro-4-$CF_3O$-phenyl, 2,4,5-trimethyl-phenyl, 2-methyl-4-chloro-phenyl, 4-acetylphenyl, 3-acetamidophenyl, 2-naphthyl;

2-Me-5-F-phenyl, 2-F-5-Me-phenyl, 2-MeO-5-F-phenyl,

2-Me-3-Cl-phenyl, 3-$NO_2$-phenyl, 2-$NO_2$-phenyl,

2-Cl-3-Me-phenyl, 2-Me-4-EtO-phenyl, 2-Me-4-F-phenyl,

2-Cl-6-F-phenyl, 2-Cl-4-($CHF_2$)O-phenyl, 2,4-diMeO-6-F-phenyl, 2-$CF_3$-6-F-phenyl, 2-MeS-phenyl, 2,6-diCl-4-MeO-phenyl, 2,3,4-triF-phenyl, 2,6-diF-4-Cl-phenyl, 2,3,4,6-tetraF-phenyl, 2,3,4,5,6-pentaF-phenyl, 2-$CF_3$-4-EtO-phenyl, 2-$CF_3$-4-iPrO-phenyl, 2-$CF_3$-4-Cl-phenyl, 2-$CF_3$-4-F-phenyl, 2-Cl-4-EtO-phenyl, 2-Cl-4-iPrO-phenyl, 2-Et-4-MeO-phenyl, 2-CHO-4-MeO-phenyl, 2-$CH_3$CH(OH)-4-MeO-phenyl, 2-$CH_3$CH(OH)-4-F-phenyl, 2-$CH_3$CH(OH)-4-Cl-phenyl, 2-$CH_3$CH(OH)-4-Me-phenyl, 2-$CH_3$CH(OMe)-4-MeO-phenyl, 2-$CH_3$C(=O)-4-MeO-phenyl, 2-$CH_3$C(=O)-4-F-phenyl, 2-$CH_3$C(=O)-4-Cl-phenyl, 2-$CH_3$C(=O)-4-Me-phenyl, 2-$H_2$C(OH)-4-MeO-phenyl, 2-$H_2$C(OMe)-4-MeO-phenyl, 2-$H_3$CCH$_2$CH(OH)-4-MeO-phenyl, 2-$H_3$CCH$_2$C(=O)-4-MeO-phenyl, 2-$CH_3CO_2CH_2CH_2$-4-MeO-phenyl, (Z)-2-HOCH$_2$CH=CH-4-MeO-phenyl, (E)-2-HOCH$_2$CH=CH-4-MeO-phenyl, (Z)-2-$CH_3CO_2$CH=CH-4-MeO-phenyl, (E)-2-$CH_3CO_2$CH=CH-4-MeO-phenyl, 2-$CH_3OCH_2CH_2$-4-MeO-phenyl, 2-F-4-MeO-phenyl, 2-Cl-4-F-phenyl, cyclohexyl, cyclopentyl, cyclohexylmethyl,
benzyl, 2-F-benzyl, 3-F-benzyl, 4-F-benzyl,
3-MeO-benzyl, 3-OH-benzyl, 2-MeO-benzyl,
2-OH-benzyl, 2-MeOC(=O)-3-MeO-phenyl,
2-Me-4-CN-phenyl, 2-Me-3-CN-phenyl,
2-Me-4-MeS-phenyl, 2-CF$_3$-4-CN-phenyl,
2-CHO-phenyl, 3-CHO-phenyl, 2-HOCH$_2$-phenyl,
3-HOCH$_2$-phenyl, 3-MeOCH$_2$-phenyl,
3-Me$_2$NCH$_2$-phenyl, 3-CN-4-F-phenyl,
2-Me-4-H$_2$NCO-phenyl, 2-Me-4-MeOC(=O)-phenyl,
3-H$_2$NCO-4-F-phenyl, 2-Me$_2$NCH$_2$-4-MeO-phenyl-,
2-Me-4-CH$_3$C(=O)-phenyl,
phenyl-NH—, (1-naphthyl)-NH—,
(2-naphthyl)-NH—, (2-[1,1'-biphenyl])-NH—,
(3-[1,1'-biphenyl])-NH—, (4-[1,1'-biphenyl])-NH—,
(2-F-phenyl)-NH—, (2-Cl-phenyl)-NH—,
(2-CF$_3$-phenyl)-NH—, (2-CH$_3$-phenyl)-NH—,
(2-OMe-phenyl)-NH—, (2-CN-phenyl)-NH—,
(2-OCF$_3$-phenyl)-NH—, (2-SMe-phenyl)-NH—,
(3-F-phenyl)-NH—, (3-Cl-phenyl)-NH—,
(3-CF$_3$-phenyl)-NH—, (3-CH$_3$-phenyl)-NH—,
(3-OMe-phenyl)-NH—, (3-CN-phenyl)-NH—,
(3-OCF$_3$-phenyl)-NH—, (3-SMe-phenyl)-NH—,
(4-F-phenyl)-NH—, (4-Cl-phenyl)-NH—,
(4-CF$_3$-phenyl)-NH—, (4-CH$_3$-phenyl)-NH—,
(4-OMe-phenyl)-NH—, (4-CN-phenyl)-NH—,
(4-OCF$_3$-phenyl)-NH—, (4-SMe-phenyl)-NH—,
(2,3-diCl-phenyl)-NH—, (2,4-diCl-phenyl)-NH—,
(2,5-diCl-phenyl)-NH—, (2,6-diCl-phenyl)-NH—,
(3,4-diCl-phenyl)-NH—, (3,5-diCl-phenyl)-NH—,
(2,3-diF-phenyl)-NH—, (2,4-diF-phenyl)-NH—,
(2,5-diF-phenyl)-NH—, (2,6-diF-phenyl)-NH—,
(3,4-diF-phenyl)-NH—, (3,5-diF-phenyl)-NH—,
(2,3-diCH$_3$-phenyl)-NH—, (2,4-diCH$_3$-phenyl)-NH—,
(2,5-diCH$_3$-phenyl)-NH—, (2,6-diCH$_3$-phenyl)-NH—,
(3,4-diCH$_3$-phenyl)-NH—, (3,5-diCH$_3$-phenyl)-NH—,
(2,3-diCF$_3$-phenyl)-NH—, (2,4-diCF$_3$-phenyl)-NH—,
(2,5-diCF$_3$-phenyl)-NH—, (2,6-diCF$_3$-phenyl)-NH—,
(3,4-diCF$_3$-phenyl)-NH—, (3,5-diCF$_3$-phenyl)-NH—,
(2,3-diOMe-phenyl)-NH—, (2,4-diOMe-phenyl)-NH—,
(2,5-diOMe-phenyl)-NH—, (2,6-dioMe-phenyl)-NH—,
(3,4-diOMe-phenyl)-NH—, (3,5-diOMe-phenyl)-NH—,
(2-F-3-Cl-phenyl)-NH—, (2-F-4-Cl-phenyl)-NH—,
(2-F-5-Cl-phenyl)-NH—, (2-F-6-Cl-phenyl)-NH—,
(2-F-3-CH$_3$-phenyl)-NH—, (2-F-4-CH$_3$-phenyl)-NH—,
(2-F-5-CH$_3$-phenyl)-NH—, (2-F-6-CH$_3$-phenyl)-NH—,
(2-F-3-CF$_3$-phenyl)-NH—, (2-F-4-CF$_3$-phenyl)-NH—,
(2-F-5-CF$_3$-phenyl)-NH—, (2-F-6-CF$_3$-phenyl)-NH—,
(2-F-3-OMe-phenyl)-NH—, (2-F-4-OMe-phenyl)-NH—,
(2-F-5-OMe-phenyl)-NH—, (2-F-6-OMe-phenyl)-NH—,
(2-Cl-3-F-phenyl)-NH—, (2-Cl-4-F-phenyl)-NH—,
(2-Cl-5-F-phenyl)-NH—, (2-Cl-6-F-phenyl)-NH—,
(2-Cl-3-CH$_3$-phenyl)-NH—, (2-Cl-4-CH$_3$-phenyl)-NH—,
(2-Cl-5-CH$_3$-phenyl)-NH—, (2-Cl-6-CH$_3$-phenyl)-NH—,
(2-Cl-3-CF$_3$-phenyl)-NH—, (2-Cl-4-CF$_3$-phenyl)-NH—,
(2-Cl-5-CF$_3$-phenyl)-NH—, (2-Cl-6-CF$_3$-phenyl)-NH—,
(2-Cl-3-OMe-phenyl)-NH—, (2-Cl-4-OMe-phenyl)-NH—,
(2-Cl-5-OMe-phenyl)-NH—, (2-Cl-6-OMe-phenyl)-NH—,
(2-CH$_3$-3-F-phenyl)-NH—, (2-CH$_3$-4-F-phenyl)-NH—,
(2-CH$_3$-5-F-phenyl)-NH—, (2-CH$_3$-6-F-phenyl)-NH—,
(2-CH$_3$-3-Cl-phenyl)-NH—, (2-CH$_3$-4-Cl-phenyl)-NH—,
(2-CH$_3$-5-Cl-phenyl)-NH—, (2-CH$_3$-6-Cl-phenyl)-NH—,
(2-CH$_3$-3-CF$_3$-phenyl)-NH—, (2-CH$_3$-4-CF$_3$-phenyl)-NH—,
(2-CH$_3$-5-CF$_3$-phenyl)-NH—, (2-CH$_3$-6-CF$_3$-phenyl)-NH—,
(2-CH$_3$-3-OMe-phenyl)-NH—, (2-CH$_3$-4-OMe-phenyl)-NH—,
(2-CH$_3$-5-OMe-phenyl)-NH—, (2-CH$_3$-6-OMe-phenyl)-NH—,
(2-CF$_3$-3-F-phenyl)-NH—, (2-CF$_3$-4-F-phenyl)-NH—,
(2-CF$_3$-5-F-phenyl)-NH—, (2-CF$_3$-6-F-phenyl)-NH—,
(2-CF$_3$-3-Cl-phenyl)-NH—, (2-CF$_3$-4-Cl-phenyl)-NH—,
(2-CF$_3$-5-Cl-phenyl)-NH—, (2-CF$_3$-6-Cl-phenyl)-NH—,
(2-CF$_3$-3-CH$_3$-phenyl)-NH—, (2-CF$_3$-4-CH$_3$-phenyl)-NH—,
(2-CH$_3$-5-CF$_3$-phenyl)-NH—, (2-CF$_3$-6-CH$_3$-phenyl)-NH—,
(2-CF$_3$-3-OMe-phenyl)-NH—, (2-CF$_3$-4-OMe-phenyl)-NH—,
(2-CF$_3$-5-OMe-phenyl)-NH—, (2-CF$_3$-6-OMe-phenyl)-NH—,
(2-OMe-3-F-phenyl)-NH—, (2-OMe-4-F-phenyl)-NH—,
(2-OMe-5-F-phenyl)-NH—, (2-OMe-6-F-phenyl)-NH—,
(2-OMe-3-Cl-phenyl)-NH—, (2-OMe-4-Cl-phenyl)-NH—,
(2-OMe-5-Cl-phenyl)-NH—, (2-OMe-6-Cl-phenyl)-NH—,
(2-OMe-3-CH$_3$-phenyl)-NH—, (2-OMe-4-CH$_3$-phenyl)-NH—,
(2-OMe-5-CH$_3$-phenyl)-NH—, (2-OMe-6-CH$_3$-phenyl)-NH—,
(2-OMe-3-CF$_3$-phenyl)-NH—, (2-OMe-4-CF$_3$-phenyl)-NH—,
(2-OMe-5-CF$_3$-phenyl)-NH—, (2-OMe-6-CF$_3$-phenyl)-NH—
(3-CF$_3$-4-Cl-phenyl)-NH—, (3-CF$_3$-4-C(O)CH$_3$-phenyl)-NH—,
(2,3,5-triCl-phenyl)-NH—, (3-CH$_3$-4-CO$_2$Me-phenyl)-NH—, and
(3-CHO-4-OMe-phenyl)-NH—; and $R^9$ is selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy.

[5] In another embodiment, the present invention provides a novel compound of Formula (I-a):

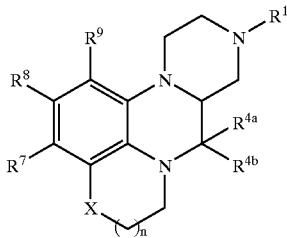

(I-a)

wherein:

X is a bond —$CH_2$—, —O—, —S—, —S(=O)—, —S(=O)$_2$—, —$NR^{10}$—, —$CH_2CH_2$—, —$OCH_2$—, —$SCH_2$—, —$CH_2O$—, —$CH_2S$—, —$NR^{10}CH_2$—, or —$CH_2NR^{10}$—;

n is 1 or 2;

$R^1$ is selected from

H,

C(=O)$R^2$,

C(=O) O$R^2$, $C_{1-8}$ alkyl, $C_{2-8}$ alkenyl, $C_{2-8}$ alkynyl, $C_{3-7}$ cycloalkyl, $C_{1-6}$ alkyl substituted with 0–2 $R^2$, $C_{2-6}$ alkenyl substituted with 0–2 $R^2$, $C_{2-6}$ alkynyl substituted with 0–2 $R^2$, aryl substituted with 0–2 $R^2$, and 5–6 membered heterocyclic ring system containing at least one heteroatom selected from the group consisting of N, O, and S, said heterocyclic ring system substituted with 0–2 $R^2$;

$R^2$, at each occurrence, is independently selected from

F, Cl, $CH_2F$, $CHF_2$, $CF_3$, $C_{1-4}$ alkyl, $C_{2-4}$ alkenyl, $C_{2-4}$ alkynyl, $C_{3-6}$ cycloalkyl, phenyl substituted with 0–5 $R^{42}$;

$C_{3-10}$ carbocyclic residue substituted with 0–3 $R^{41}$, and

5–10 membered heterocyclic ring system containing from 1–4 heteroatoms selected from the group consisting of N, O, and S substituted with 0–3 $R^{41}$;

$R^{4a}$ is H or $C_{1-4}$ alkyl;

$R^{4b}$ is H;

alternatively, $R^{4a}$ and $R^{4b}$ are taken together to form =O or =S;

$R^7$ and $R^9$, at each occurrence, are independently selected from

H, halo, —$CF_3$, —$OCF_3$, —OH, —CN, —$NO_2$, —$NR^{46}R^{47}$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

O$R^{12}$, S$R^{12}$, N$R^{12}R^{13}$, C(O)H, C(O)$R^{12}$, C(O)N$R^{12}R^{13}$, $NR^{14}C(O)R^{12}$, C(O)O$R^{12}$, OC(O)$R^{12}$, OC(O)O$R^{12}$,

CH(=$NR^{14}$)N$R^{12}R^{13}$, NHC(=$NR^{14}$)N$R^{12}R^{13}$, S(O)$R^{12}$, S(O)$_2R^{12}$,

S(O)N$R^{12}R^{13}$, S(O)$_2$N$R^{12}R^{13}$, $NR^{14}$S(O)$R^{12}$, $NR^{14}$S(O)$_2R^{12}$, $NR^{12}$C(O)$R^{15}$, $NR^{12}$C(O)O$R^{15}$, $NR^{12}$S(O)$_2R^{15}$, and $NR^{12}$C(O)NH$R^{15}$;

$R^8$ is selected from

H, halo, —$CF_3$, —$OCF_3$, —OH, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

O$R^{12}$, S$R^{12}$, N$R^{12}R^{13}$, C(O)H, C(O)$R^{12}$, C(O)N$R^{12}R^{13}$, $NR^{14}C(O)R^{12}$, C(O)O$R^{12}$, OC(O)$R^{12}$, OC(O)O$R^{12}$,

CH(=$NR^{14}$)N$R^{12}R^{13}$, NHC(=$NR^{14}$)N$R^{12}R^{13}$, S(O)$R^{12}$, S(O)$_2R^{12}$,

S(O)N$R^{12}R^{13}$, S(O)$_2$N$R^{12}R^{13}$, $NR^{14}$S(O)$R^{12}$, $NR^{14}$S(O)$_2R^{12}$, $NR^{12}$C(O)$R^{15}$, $NR^{12}$C(O)O$R^{15}$, $NR^{12}$S(O)$_2R^{15}$, and $NR^{12}$C(O)NH$R^{15}$;

$R^{10}$ is selected from H, $C_{1-4}$ alkyl, $C_{2-4}$ alkenyl, $C_{2-4}$ alkynyl, and $C_{1-4}$ alkoxy;

$R^{11}$ is selected from

H, halo, —$CF_3$, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

O$R^{12}$, S$R^{12}$, N$R^{12}R^{13}$, C(O)H, C(O)$R^{12}$, C(O)N$R^{12}R^{13}$, $NR^{14}C(O)R^{12}$, C(O)O$R^{12}$, OC(O)$R^{12}$, OC(O)O$R^{12}$,

CH(=$NR^{14}$)N$R^{12}R^{13}$, NHC(=$NR^{14}$)N$R^{12}R^{13}$, S(O)$R^{12}$, S(O)$_2R^{12}$,

S(O)N$R^{12}R^{13}$, S(O)$_2$N$R^{12}R^{13}$, $NR^{14}$S(O)$R^{12}$, $NR^{14}$S(O)$_2R^{12}$, $NR^{12}$C(O)$R^{15}$, $NR^{12}$C(O)O$R^{15}$, $NR^{12}$S(O)$_2R^{15}$, and $NR^{12}$C(O)NH$R^{15}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, aryl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

C$_{3-10}$ carbocyclic residue substituted with 0–3 R$^{33}$, and
5–10 membered heterocyclic ring system containing from 1–4 heteroatoms selected from the group consisting of N, O, and S substituted with 0–3 R$^{31}$.
R$^{13}$, at each occurrence, is independently selected from H, C$_{1-4}$ alkyl, C$_{2-4}$ alkenyl, and C$_{2-4}$ alkynyl;
alternatively, R$^{12}$ and R$^{13}$ join to form a 5- or 6-membered ring optionally substituted with —O— or —N(R$^{14}$)—;
alternatively, R$^{12}$ and R$^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 R$^{16}$;
R$^{14}$, at each occurrence, is independently selected from H and C$_{1-4}$ alkyl;
R$^{15}$, at each occurrence, is independently selected from H, C$_{1-4}$ alkyl, C$_{2-4}$ alkenyl, and C$_{2-4}$ alkynyl;
R$^{16}$, at each occurrence, is independently selected from H, OH, halo, CN, NO$_2$, CF$_3$, SO$_2$R$^{45}$, NR$^{46}$R$^{47}$, —C(=O)H, C$_{1-4}$ alkyl, C$_{2-4}$ alkenyl, C$_{2-4}$ alkynyl, C$_{1-4}$ haloalkyl, C$_{1-3}$ haloalkyl-oxy-, and C$_{1-3}$ alkyloxy-;
R$^{31}$, at each occurrence, is independently selected from H, OH, halo, CF$_3$, SO$_2$R$^{45}$, NR$^{46}$R$^{47}$, and C$_{1-4}$ alkyl;
R$^{33}$, at each occurrence, is independently selected from
  H, OH, halo, CN, NO$_2$, CF$_3$, SO$_2$R$^{45}$, NR$^{46}$R$^{47}$, —C(=O)H, phenyl, C$_{1-6}$ alkyl, C$_{2-6}$ alkenyl, C$_{2-6}$ alkynyl,
  C$_{3-6}$ cycloalkyl, C$_{1-4}$ haloalkyl, C$_{1-4}$ haloalkyl-oxy-, C$_{1-4}$ alkyloxy-, C$_{1-4}$ alkylthio-, C$_{1-4}$ alkyl-C(=O)—,
  C$_{1-4}$ alkyl-C(=O)NH—, C$_{1-4}$ alkyl-OC(=O)—,
  C$_{1-4}$ alkyl-C(=O)O—, C$_{3-6}$ cycloalkyl-oxy-,
  C$_{3-6}$ cycloalkylmethyl-oxy-;
  C$_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—; and
  C$_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—;
R$^{41}$, at each occurrence, is independently selected from
  H, CF$_3$, halo, OH, CO$_2$H, SO$_2$R$^{45}$, NR$^{46}$R$^{47}$, NO$_2$, CN;
  C$_{2-8}$ alkenyl, C$_{2-8}$ alkynyl, C$_{1-4}$ alkoxy, C$_{1-4}$ haloalkyl
  C$_{1-4}$ alkyl substituted with 0–1 R$^{43}$,
  aryl substituted with 0–3 R$^{42}$, and
  5–10 membered heterocyclic ring system containing from 1–4 heteroatoms selected from the group consisting of N, O, and S substituted with 0–3 R$^{44}$;
R$^{42}$, at each occurrence, is independently selected from
  H, CF$_3$, halo, OH, CO$_2$H, SO$_2$R$^{45}$, NR$^{46}$R$^{47}$, NO$_2$, CN, CH(=NH)NH$_2$, NHC(=NH)NH$_2$,
  C$_{2-6}$ alkenyl, C$_{2-6}$ alkynyl, C$_{1-4}$ alkoxy, C$_{1-4}$ haloalkyl, C$_{3-6}$ cycloalkyl,
  C$_{1-4}$ alkyl substituted with 0–1 R$^{43}$,
  aryl substituted with 0–3 R$^{44}$, and
  5–10 membered heterocyclic ring system containing from 1–4 heteroatoms selected from the group consisting of N, O, and S substituted with 0–3 R$^{44}$;
R$^{43}$ is C$_{3-6}$ cycloalkyl or aryl substituted with 0–3 R$^{44}$;
R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, C$_{1-4}$ alkyl, and C$_{1-4}$ alkoxy;
R$^{45}$ is C$_{1-4}$ alkyl;
R$^{46}$, at each occurrence, is independently selected from H and C$_{1-4}$ alkyl; and
R$^{47}$, at each occurrence, is independently selected from H and C$_{1-4}$ alkyl.

[6] In another embodiment, the present invention provides a novel compound of Formula (I-b):

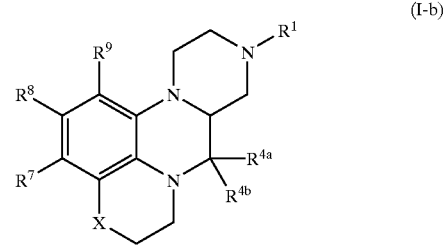

(I-b)

wherein:
X is —CH$_2$—, —O—, —S—, —CH$_2$CH$_2$—, —OCH$_2$—, —SCH$_2$—, —CH$_2$O—, or —CH$_2$S—;
R$^1$ is selected from
  H,
  C(=O) R$^2$,
  C(=O)OR$^2$,
  C$_{1-6}$ alkyl,
  C$_{2-6}$ alkenyl,
  C$_{2-6}$ alkynyl,
  C$_{3-6}$ cycloalkyl,
  C$_{1-4}$ alkyl substituted with 0–2 R$^2$,
  C$_{2-4}$ alkenyl substituted with 0–2 R$^2$, and
  C$_{2-4}$ alkynyl substituted with 0–2 R$^2$;
R$^2$, at each occurrence, is independently selected from
  C$_{1-4}$ alkyl,
  C$_{2-4}$ alkenyl,
  C$_{2-4}$ alkynyl,
  C$_{3-6}$ cycloalkyl,
  phenyl substituted with 0–5 R$^{42}$;
  C$_{3-10}$ carbocyclic residue substituted with 0–3 R$^{41}$, and
  5–10 membered heterocyclic ring system containing from 1–4 heteroatoms selected from the group consisting of N, O, and S substituted with 0–3 R$^{41}$;
R$^{4a}$ is H or C$_{1-4}$ alkyl;
R$^{4b}$ is H;
alternatively, R$^{4a}$ and R$^{4b}$ are taken together to form =O or =S;
R$^7$ and R$^9$, at each occurrence, are independently selected from
  H, halo, —CF$_3$, —OCF$_3$, —OH, —CN, —NO$_2$, —NR$^{46}$R$^{47}$,
  C$_{1-6}$ alkyl, C$_{2-6}$ alkenyl, C$_{2-6}$ alkynyl, C$_{1-6}$ haloalkyl, C$_{1-6}$ alkoxy, (C$_{1-4}$ haloalkyl)oxy,
  C$_{3-10}$ cycloalkyl substituted with 0–2 R$^{33}$,
  C$_{1-4}$ alkyl substituted with 0–2 R$^{11}$,
  C$_{3-10}$ carbocyclic residue substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, and NR$^{14}$S(O)$_2$R$^{12}$;
R$^8$ is selected from H, halo, —$CF_3$, —$OCF_3$, —OH, —CN, —$NO_2$,
$C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(=$NR^{14}$)$NR^{12}R^{13}$, NHC(=$NR^{14}$) $NR^{12}R^{13}$, S(O)$R^{12}$, S(O)$_2R^{12}$,
S(O)$NR^{12}R^{13}$, S(O)$_2NR^{12}R^{13}$, $NR^{14}$S(O)$R^{12}$, $NR^{14}$S(O)$_2$ $R^{12}$,
$NR^{12}C(O)R^{15}$, $NR^{12}C(O)OR^{15}$, $NR^{12}$S(O)$_2R^{15}$, and $NR^{12}C(O)NHR^{15}$;
$R^{11}$ is selected from
H, halo, —$CF_3$, —CN, —$NO_2$, $C_{1-6}$ alkyl,
$C_{2-6}$ alkenyl, $C_{2-6}$ alkynyl, $C_{1-4}$ haloalkyl, $C_{1-6}$ alkoxy, $C_{3-10}$ cycloalkyl,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, and $NR^{14}$S(O)$_2R^{12}$;
$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;
$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;
$R^{13}$, at each occurrence, is independently selected from H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)—;
alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H, methyl, ethyl, propyl, and butyl;
$R^{15}$, at each occurrence, is independently selected from H, $C_{1-4}$ alkyl, $C_{2-4}$ alkenyl, and $C_{2-4}$ alkynyl;
$R^{16}$, at each occurrence, is independently selected from H, OH, F, Cl, CN, $NO_2$, $CF_3$, $SO_2R^{45}$, $NR^{46}R^{47}$, —C(=O) H, methyl, ethyl, methoxy, ethoxy, trifluoromethyl, and trifluoromethoxy;
$R^{31}$, at each occurrence, is independently selected from H, OH, halo, $CF_3$, $SO_2R^{45}$, $NR^{46}R^{47}$, and $C_{1-4}$ alkyl;
$R^{33}$, at each occurrence, is independently selected from H, OH, halo, CN, $NO_2$, $CF_3$, $SO_2R^{45}$, $NR^{46}R^{47}$, —C(=O)H, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{41}$, at each occurrence, is independently selected from

H, $CF_3$, halo, OH, $CO_2$H, $SO_2R^{45}$, $NR^{46}R^{47}$, $NO_2$, CN, $C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from

H, $CF_3$, halo, OH, $CO_2$H, $SO_2R^{45}$, $NR^{46}R^{47}$, $NO_2$, CN, CH(=NH)$NH_2$, NHC(=NH)$NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2$H, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl; and $R^{47}$, at each occurrence, is independently selected from H and $C_{1-4}$ alkyl.

[7] In another embodiment, the present invention provides a novel compound of Formula (I-b):

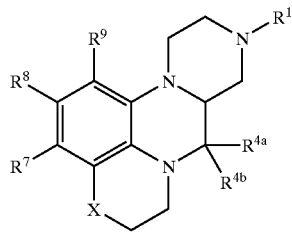

(I-b)

wherein:

X is —CH$_2$—, —O—, —S—, —CH$_2$CH$_2$—, —OCH$_2$—, or —SCH$_2$—;

R$^1$ is selected from
- H,
- C$_{1-4}$ alkyl,
- C$_{2-4}$ alkenyl,
- C$_{2-4}$ alkynyl,
- C$_{3-4}$ cycloalkyl,
- C$_{1-3}$ alkyl substituted with 0–1 R$^2$,
- C$_{2-3}$ alkenyl substituted with 0–1 R$^2$, and
- C$_{2-3}$ alkynyl substituted with 0–1 R$^2$;

R$^2$, at each occurrence, is independently selected from
- C$_{1-4}$ alkyl,
- C$_{2-4}$ alkenyl,
- C$_{2-4}$ alkynyl,
- C$_{3-6}$ cycloalkyl,
- phenyl substituted with 0–5 R$^{42}$;
- C$_{3-6}$ carbocyclic residue substituted with 0–3 R$^{41}$, and
- 5–6 membered heterocyclic ring system containing 1, 2, or 3 heteroatoms selected from the group consisting of N, O, and S substituted with 0–3 R$^{41}$;

R$^{4a}$ is H, methyl, ethyl, propyl, or butyl;
R$^{4b}$ is H;
alternatively, R$^{4a}$ and R$^{4b}$ are taken together to form =O or =S;

R$^7$ and R$^9$, at each occurrence, are independently selected from
- H, halo, —CF$_3$, —OCF$_3$, —OH, —CN, —NO$_2$, —NR$^{46}$R$^{47}$,
- C$_{1-4}$ alkyl, C$_{2-4}$ alkenyl, C$_{2-4}$ alkynyl, C$_{1-4}$ haloalkyl,
- C$_{1-4}$ alkoxy, (C$_{1-4}$ haloalkyl)oxy,
- C$_{3-10}$ cycloalkyl substituted with 0–2 R$^{33}$,
- C$_{1-4}$ alkyl substituted with 0–2 R$^{11}$,
- C$_{3-10}$ carbocyclic residue substituted with 0–3 R$^{33}$,
- aryl substituted with 0–5 R$^{33}$, and
- 5–6 membered heterocyclic ring system containing 1, 2, or 3 heteroatoms selected from the group consisting of N, O, and S substituted with 0–3 R$^{31}$;

R$^8$ is selected from
- H, halo, —CF$_3$, —OCF$_3$, —OH, —CN, —NO$_2$,
- C$_{1-4}$ alkyl, C$_{2-4}$ alkenyl, C$_{2-4}$ alkynyl, C$_{1-4}$ haloalkyl, C$_{1-4}$ alkoxy, (C$_{1-4}$ haloalkyl)oxy,
- C$_{3-10}$ cycloalkyl substituted with 0–2 R$^{33}$,
- C$_{1-4}$ alkyl substituted with 0–2 R$^{11}$,
- C$_{2-4}$ alkenyl substituted with 0–2 R$^{11}$,
- C$_{2-4}$ alkynyl substituted with 0–1 R$^{11}$,
- C$_{3-10}$ carbocyclic residue substituted with 0–3 R$^{33}$,
- aryl substituted with 0–5 R$^{33}$,
- 5–6 membered heterocyclic ring system containing 1, 2, or 3 heteroatoms selected from the group consisting of N, O, and S substituted with 0–3 R$^{31}$;
- OR$^{12}$, SR$^{12}$, NR$^{12}$R$^{13}$, NR$_{12}$C(O)R$^{15}$, NR$^{12}$C(O)OR$^{15}$, NR$^{12}$S(O)$_2$R$^{15}$, and NR$^{12}$C(O)NHR$^{15}$;

R$^{11}$ is selected from
- H, halo, —CF$_3$, —CN, —NO$_2$,
- C$_{1-4}$ alkyl, C$_{2-4}$ alkenyl, C$_{2-4}$ alkynyl, C$_{1-4}$ haloalkyl, C$_{1-4}$ alkoxy, (C$_{1-4}$ haloalkyl)oxy,
- C$_{3-10}$ cycloalkyl substituted with 0–2 R$^{33}$,
- C$_{3-10}$ carbocyclic residue substituted with 0–3 R$^{33}$,
- aryl substituted with 0–5 R$^{33}$, and
- 5–6 membered heterocyclic ring system containing 1, 2, or 3 heteroatoms selected from the group consisting of N, O, and S substituted with 0–3 R$^{31}$;

R$^{12}$, at each occurrence, is independently selected from
- C$_{1-4}$ alkyl substituted with 0–1 R$^{12a}$,
- C$_{2-4}$ alkenyl substituted with 0–1 R$^{12a}$,
- C$_{2-4}$ alkynyl substituted with 0–1 R$^{12a}$,
- C$_{3-6}$ cycloalkyl substituted with 0–3 R$^{33}$,
- aryl substituted with 0–5 R$^{33}$;
- C$_{3-10}$ carbocyclic residue substituted with 0–3 R$^{33}$, and
- 5–10 membered heterocyclic ring system containing from 1–4 heteroatoms selected from the group consisting of N, O, and S substituted with 0–3 R$^{31}$;

R$^{12a}$, at each occurrence, is independently selected from
- phenyl substituted with 0–5 R$^{33}$;
- C$_{3-10}$ carbocyclic residue substituted with 0–3 R$^{33}$, and
- 5–10 membered heterocyclic ring system containing from 1–4 heteroatoms selected from the group consisting of N, O, and S substituted with 0–3 R$^{31}$;

R$^{13}$, at each occurrence, is independently selected from H, C$_{1-4}$ alkyl, C$_{2-4}$ alkenyl, and C$_{2-4}$ alkynyl;

alternatively, R$^{12}$ and R$^{13}$ join to form a 5- or 6-membered ring optionally substituted with —O— or —N(R$^{14}$)—;

alternatively, R$^{12}$ and R$^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 R$^{16}$;

R$^{14}$, at each occurrence, is independently selected from H, methyl, ethyl, propyl, and butyl;

R$^{15}$, at each occurrence, is independently selected from H, methyl, ethyl, propyl, and butyl;

R$^{16}$, at each occurrence, is independently selected from H, OH, F, Cl, CN, NO$_2$, methyl, ethyl, methoxy, ethoxy, trifluoromethyl, and trifluoromethoxy;

R$^{31}$, at each occurrence, is independently selected from H, OH, halo, CF$_3$, methyl, ethyl, and propyl;

R$^{33}$, at each occurrence, is independently selected from
- H, OH, halo, CN, NO$_2$, CF$_3$, SO$_2$R$^{45}$, NR$^{46}$R$^{47}$, —C(=O)H,
- phenyl, C$_{1-6}$ alkyl, C$_{2-6}$ alkenyl, C$_{2-6}$ alkynyl,
- C$_{3-6}$ cycloalkyl, C$_{1-4}$ haloalkyl, C$_{1-4}$ haloalkyl-oxy-,
- C$_{1-4}$ alkyloxy-, C$_{1-4}$ alkylthio-, C$_{1-4}$ alkyl-C(=O)—,
- C$_{1-4}$ alkyl-C(=O)NH—, C$_{1-4}$ alkyl-OC(=O)—,
- C$_{1-4}$ alkyl-C(=O)O—, C$_{3-6}$ cycloalkyl-oxy-,
- C$_{3-6}$ cycloalkylmethyl-oxy-;
- C$_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—; and $C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from
  H, $CF_3$, halo, OH, $CO_2H$, $SO_2R^{45}$, $NR^{46}R^{47}$, $NO_2$, CN, CH(=NH)$NH_2$, NHC(=NH)$NH_2$,
  $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl; and $R^{47}$, at each occurrence, is independently selected from from H, methyl, ethyl, propyl, and butyl.

[8] In another embodiment, the present invention provides a novel compound of Formula (I-b):

X is —$CH_2$—, —O— or —S—;

$R^1$ is selected from
  H,
  $C_{1-4}$ alkyl,
  $C_{2-4}$ alkenyl,
  $C_{2-4}$ alkynyl,
  $C_{3-4}$ cycloalkyl,
  $C_{1-3}$ alkyl substituted with 0–1 $R^2$,
  $C_{2-3}$ alkenyl substituted with 0–1 $R^2$, and
  $C_{2-3}$ alkynyl substituted with 0–1 $R^2$;

$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{42}$;
  $C_{3-6}$ carbocyclic residue substituted with 0–3 $R^{41}$, and
  5–6 membered heterocyclic ring system containing 1, 2, or 3 heteroatoms selected from the group consisting of N, O, and S substituted with 0–3 $R^{41}$;

$R^{4a}$ is H;

$R^{4b}$ is H;

alternatively, $R^{4a}$ and $R^{4b}$ are taken together to form =O;

$R^7$ and $R^9$, at each occurrence, are independently selected from
  H, F, Cl, —$CH_3$, —$OCH_3$, —$CF_3$, —$OCF_3$, —CN, and —$NO_2$, $R^8$ is selected from
  H, F, Cl, Br, —$CF_3$, —$OCF_3$, —OH, —CN, —$NO_2$,
  $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^{11}$,
  $C_{2-4}$ alkenyl substituted with 0–2 $R^{11}$,
  $C_{2-4}$ alkynyl substituted with 0–1 $R^{11}$,
  $C_{3-10}$ carbocyclic residue substituted with 0–3 $R^{33}$,
  aryl substituted with 0–5 $R^{33}$,
  5–6 membered heterocyclic ring system containing 1, 2, or 3 heteroatoms selected from the group consisting of N, O, and S substituted with 0–3 $R^{31}$;
  $OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
  H, halo, —$CF_3$, —CN, —$NO_2$,
  $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
  $C_{3-10}$ cycloalkyl substituted with 0–2 $R^{33}$,
  $C_{3-10}$ carbocyclic residue substituted with 0–3 $R^{33}$,
  aryl substituted with 0–5 $R^{33}$, and
  5–6 membered heterocyclic ring system containing 1, 2, or 3 heteroatoms selected from the group consisting of N, O, and S substituted with 0–3 $R^{31}$;

$R^{12}$, at each occurrence, is independently selected from
  $C_{1-4}$ alkyl substituted with 0–1 $R^{12a}$,
  $C_{2-4}$ alkenyl substituted with 0–1 $R^{12a}$,
  $C_{2-4}$ alkynyl substituted with 0–1 $R^{12a}$,
  $C_{3-6}$ cycloalkyl substituted with 0–3 $R^{33}$,
  aryl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{31}$;

$R^{12a}$, at each occurrence, is independently selected from
  phenyl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from
  H, OH, halo, CN, $NO_2$, $CF_3$, $SO_2R^{45}$, $NR^{46}R^{47}$, —C(=O)H,
  phenyl, $C_{1-6}$ alkyl, $C_{2-6}$ alkenyl, $C_{2-6}$ alkynyl,
  $C_{3-6}$ cycloalkyl, $C_{1-4}$ haloalkyl, $C_{1-4}$ haloalkyl-oxy-,
  $C_{1-4}$ alkyloxy-, $C_{1-4}$ alkylthio-, $C_{1-4}$ alkyl-C(=O)—,
  $C_{1-4}$ alkyl-C(=O)NH—, $C_{1-4}$ alkyl-OC(=O)—,
  $C_{1-4}$ alkyl-C(=O)O—, $C_{3-6}$ cycloalkyl-oxy-,
  $C_{3-6}$ cycloalkylmethyl-oxy-;
  $C_{1-6}$ alkyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—; and $C_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—;

R$^{41}$, at each occurrence, is independently selected from H, CF$_3$, halo, OH, CO$_2$H, SO$_2$R$^{45}$, NR$^{46}$R$^{47}$, NO$_2$, CN, C$_{2-4}$ alkenyl, C$_{2-4}$ alkynyl, C$_{1-3}$ alkoxy, C$_{1-3}$ haloalkyl, and C$_{1-3}$ alkyl;

R$^{42}$, at each occurrence, is independently selected from H, CF$_3$, halo, OH, CO$_2$H, SO$_2$R$^{45}$, NR$^{46}$R$^{47}$, NO$_2$, CN, CH(=NH)NH$_2$, NHC(=NH)NH$_2$, C$_{2-4}$ alkenyl, C$_{2-4}$ alkynyl, C$_{1-3}$ alkoxy, C$_{1-3}$ haloalkyl, C$_{3-6}$ cycloalkyl, and C$_{1-3}$ alkyl;

R$^{43}$ is cyclopropyl, cyclobutyl, cyclopentyl, cyclohexyl, phenyl, or pyridyl, each substituted with 0–3 R$^{44}$;

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, methyl, ethyl, propyl, butyl, methoxy, ethoxy, propoxy, and butoxy;

R$^{45}$ is methyl, ethyl, propyl, or butyl;

R$^{46}$, at each occurrence, is independently selected from H, methyl, ethyl, propyl, and butyl; and R$^{47}$, at each occurrence, is independently selected from from H, methyl, ethyl, propyl, and butyl.

[9] In another embodiment, the present invention provides a novel compound of Formula (I-b):

X is —CH$_2$—, —O—, or —S—;

R$^1$ is selected from H,
  C$_{1-5}$ alkyl substituted with 0–1 R$^2$,
  C$_{2-5}$ alkenyl substituted with 0–1 R$^2$, and
  C$_{2-3}$ alkynyl substituted with 0–1 R$^2$;

R$^2$ is C$_{3-6}$ cycloalkyl;

R$^{4a}$ is H;

R$^{4b}$ is H;

R$^7$ and R$^9$, at each occurrence, are independently selected from H, F, Cl, —CH$_3$, —OCH$_3$, —CF$_3$, —OCF$_3$, —CN, and —NO$_2$;

R$^8$ is selected from R$^{11}$;
  methyl substituted with R$^{11}$;
  phenyl substituted with 0–2 R$^{33}$;
  OR$^{12}$, SR$^{12}$, NR$^{12}$R$^{13}$, NR$^{12}$C(O) R$^{15}$, NR$^{12}$C(O)OR$^{15}$, NR$^{12}$S(O)$_2$R$^{15}$, and NR$^{12}$C(O)NHR$^{15}$;

R$^{11}$ is selected from
  phenyl-substituted with 0–5 fluoro;
  naphthyl-substituted with 0–3 R$^{33}$;
  2-(H$_3$CCH$_2$C(=O))-phenyl-substituted with R$^{33}$;
  2-(H$_3$CC(=O))-phenyl-substituted with R$^{33}$;
  2-(HC(=O))-phenyl-substituted with R$^{33}$;
  2-(H$_3$CCH(OH))-phenyl-substituted with R$^{33}$;
  2-(H$_3$CCH$_2$CH(OH))-phenyl-substituted with R$^{33}$;
  2-(HOCH$_2$)-phenyl-substituted with R$^{33}$;
  2-(HOCH$_2$CH$_2$)-phenyl-substituted with R$^{33}$;
  2-(H$_3$COCH$_2$)-phenyl-substituted with R$^{33}$;
  2-(H$_3$COCH$_2$CH$_2$)-phenyl-substituted with R$^{33}$;
  2-(H$_3$CCH(OMe))-phenyl-substituted with R$^{33}$;
  2-(H$_3$COC(=O))-phenyl-substituted with R$^{33}$;
  2-(HOCH$_2$CH=CH)-phenyl-substituted with R$^{33}$;
  2-((MeOC=O)CH=CH)-phenyl-substituted with R$^{33}$;
  2-(methyl)-phenyl-substituted with R$^{33}$;
  2-(ethyl)-phenyl-substituted with R$^{33}$;
  2-(i-propyl)-phenyl-substituted with R$^{33}$;
  2-(F$_3$C)-phenyl-substituted with R$^{33}$;
  2-(NC)-phenyl-substituted with R$^{33}$;
  2-(H$_3$CO)-phenyl-substituted with R$^{33}$;
  2-(fluoro)-phenyl-substituted with R$^{33}$;
  2-(chloro)-phenyl-substituted with R$^{33}$;
  3-(NC)-phenyl-substituted with R$^{33}$;
  3-(H$_3$CO)-phenyl-substituted with R$^{33}$;
  3-(fluoro)-phenyl-substituted with R$^{33}$;
  3-(chloro)-phenyl-substituted with R$^{33}$;
  4-(NC)-phenyl-substituted with R$^{33}$;
  4-(fluoro)-phenyl-substituted with R$^{33}$;
  4-(chloro)-phenyl-substituted with R$^{33}$;
  4-(H$_3$CS)-phenyl-substituted with R$^{33}$;
  4-(H$_3$CO)-phenyl-substituted with R$^{33}$;
  4-(ethoxy)-phenyl-substituted with R$^{33}$;
  4-(i-propoxy)-phenyl-substituted with R$^{33}$;
  4-(i-butoxy)-phenyl-substituted with R$^{33}$;
  4-(H$_3$CCH$_2$CH$_2$C(=O))-phenyl-substituted with R$^{33}$;
  4-((H$_3$C)$_2$CHC(=O))-phenyl-substituted with R$^{33}$;
  4-(H$_3$CCH$_2$C(=O))-phenyl-substituted with R$^{33}$;
  4-(H$_3$CC(=O))-phenyl-substituted with R$^{33}$;
  4-(H$_3$CCH$_2$CH$_2$CH(OH))-phenyl-substituted with R$^{33}$;
  4-(H$_3$C)$_2$CHCH (OH))-phenyl-substituted with R$^{33}$;
  4-(H$_3$CCH$_2$CH (OH))-phenyl-substituted with R$^{33}$;
  4-(H$_3$CCH(OH))-phenyl-substituted with R$^{33}$;
  4-(cyclopropyloxy)-phenyl-substituted with R$^{33}$;
  4-(cyclobutyloxy)-phenyl-substituted with R$^{33}$; and
  4-(cyclopentyloxy)-phenyl-substituted with R$^{33}$;

R$^{12}$ is selected from
  phenyl-substituted with 0–5 fluoro;
  naphthyl-substituted with 0–3 R$^{33}$;
  2-(H$_3$CCH$_2$C(=O))-phenyl-substituted with R$^{33}$;
  2-(H$_3$CC(=O))-phenyl-substituted with R$^{33}$;
  2-(HC(=O))-phenyl-substituted with R$^{33}$;
  2-(H$_3$CCH(OH))-phenyl-substituted with R$^{33}$;
  2-(H$_3$CCH$_2$CH (OH))-phenyl-substituted with R$^{33}$;
  2-(HOCH$_2$)-phenyl-substituted with R$^{33}$;
  2-(HOCH$_2$CH$_2$)-phenyl-substituted with R$^{33}$;
  2-(H$_3$COCH$_2$)-phenyl-substituted with R$^{33}$;
  2-(H$_3$COCH$_2$CH$_2$)-phenyl-substituted with R$^{33}$;
  2-(H$_3$CCH(OMe))-phenyl-substituted with R$^{33}$;
  2-(H$_3$COC(=O))-phenyl-substituted with R$^{33}$;
  2-(HOCH$_2$CH=CH)-phenyl-substituted with R$^{33}$;
  2-((MeOC=O)CH=CH)-phenyl-substituted with R$^{33}$;
  2-(methyl)-phenyl-substituted with R$^{33}$;
  2-(ethyl)-phenyl-substituted with R$^{33}$;
  2-(i-propyl)-phenyl-substituted with R$^{33}$;
  2-(F$_3$C)-phenyl-substituted with R$^{33}$;
  2-(NC)-phenyl-substituted with R$^{33}$;
  2-(H$_3$CO)-phenyl-substituted with R$^{33}$;
  2-(fluoro)-phenyl-substituted with R$^{33}$;
  2-(chloro)-phenyl-substituted with R$^{33}$;
  3-(NC)-phenyl-substituted with R$^{33}$;
  3-(H$_3$CO)-phenyl-substituted with R$^{33}$;
  3-(fluoro)-phenyl-substituted with R$^{33}$;
  3-(chloro)-phenyl-substituted with R$^{33}$;
  4-(NC)-phenyl-substituted with R$^{33}$;
  4-(fluoro)-phenyl-substituted with R$^{33}$;
  4-(chloro)-phenyl-substituted with R$^{33}$;

4-(($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C(=O)$)-phenyl-substituted with $R^{33}$;
4-(($H_3C)_2CHC(=O)$)-phenyl-substituted with $R^{33}$;
4-($H_3CCH_2CH(=O)$)-phenyl-substituted with $R^{33}$;
4-($H_3CC(=O)$)-phenyl-substituted with $R^{33}$;
4-($H_3CCH_2CH_2CH(OH)$)-phenyl-substituted with $R^{33}$;
4-(($H_3C)_2CHCH(OH)$)-phenyl-substituted with $R^{33}$;
4-($H_3CCH_2CH(OH)$)-phenyl-substituted with $R^{33}$;
4-($H_3CCH(OH)$)-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy; and $R^{33}$, at each occurrence, is independently selected from H, F, Cl, —$CH_3$, —$OCH_3$, —$CF_3$, —$OCF_3$, —CN, and —$NO_2$.

[10] In another embodiment, the present invention provides a novel compound of Formula (I-b):

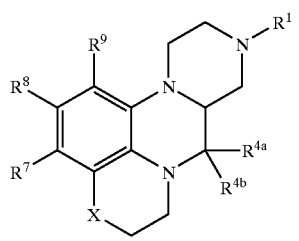

(I-b)

wherein:

$R^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, —CH=$CH_2$, —$CH_2$—CH=$CH_2$, —CH=CH—$CH_3$, —C≡CH, —C≡C—$CH_3$, and —$CH_2$—C≡CH;

$R^{4a}$ is H;
$R^{4b}$ is H;
alternatively, $R^{4a}$ and $R^{4b}$ are taken together to form =O;

$R^7$ and $R^9$, at each occurrence, are independently selected from hydrogen, fluoro, methyl, trifluoromethyl, and methoxy;

$R^8$ is selected from
  hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl,
  methylC(=O)—, ethylC(=O)—, propylC(=O)—, isopropylC(=O)—, butylC(=O)—, phenylC(=O)—,
  methyl$CO_2$—, ethyl$CO_2$—, propyl$CO_2$—, isopropyl$CO_2$—,
  butyl$CO_2$—, phenyl$CO_2$—,
  dimethylamino-S(=O)—, diethylamino-S(=O)—,
  dipropylamino-S(=O)—, di-isopropylamino-S(=O)—,
  dibutylamino-S(=O)—, diphenylamino-S(=O)—,
  dimethylamino-$SO_2$—, diethylamino-$SO_2$—,
  dipropylamino-$SO_2$—, di-isopropylamino-$SO_2$—,
  dibutylamino-$SO_2$—, diphenylamino-$SO_2$—,
  dimethylamino-C(=O)—, diethylamino-C(=O)—,
  dipropylamino-C(=O)—, di-isopropylamino-C(=O)—,
  dibutylamino-C(=O)—, diphenylamino-C(=O)—,
  2-chlorophenyl, 2-fluorophenyl, 2-bromophenyl,
  2-cyanophenyl, 2-methylphenyl, 2-trifluoromethylphenyl,
  2-methoxyphenyl, 2-trifluoromethoxyphenyl,
  3-chlorophenyl, 3-fluorophenyl, 3-bromophenyl,
  3-cyanophenyl, 3-methylphenyl, 3-ethylphenyl,
  3-propylphenyl, 3-isopropylphenyl, 3-butylphenyl,
  3-trifluoromethylphenyl, 3-methoxyphenyl,
  3-isopropoxyphenyl, 3-trifluoromethoxyphenyl,
  3-thiomethoxyphenyl,
  4-chlorophenyl, 4-fluorophenyl, 4-bromophenyl,
  4-cyanophenyl, 4-methylphenyl, 4-ethylphenyl,
  4-propylphenyl, 4-isopropylphenyl, 4-butylphenyl,
  4-trifluoromethylphenyl, 4-methoxyphenyl,
  4-isopropoxyphenyl, 4-trifluoromethoxyphenyl,
  4-thiomethoxyphenyl,
  2,3-dichlorophenyl, 2,3-difluorophenyl,
  2,3-dimethylphenyl, 2,3-ditrifluoromethylphenyl,
  2,3-dimethoxyphenyl, 2,3-ditrifluoromethoxyphenyl,
  2,4-dichlorophenyl, 2,4-difluorophenyl,
  2,4-dimethylphenyl, 2,4-ditrifluoromethylphenyl,
  2,4-dimethoxyphenyl, 2,4-ditrifluoromethoxyphenyl,
  2,5-dichlorophenyl, 2,5-difluorophenyl,
  2,5-dimethyphenyl, 2,5-ditrifluoromethylphenyl,
  2,5-dimethoxyphenyl, 2,5-ditrifluoromethoxyphenyl,
  2,6-dichlorophenyl, 2,6-difluorophenyl,
  2,6-dimethylphenyl, 2,6-ditrifluoromethylphenyl,
  2,6-dimethoxyphenyl, 2,6-ditrifluoromethoxyphenyl,
  3,4-dichlorophenyl, 3,4-difluorophenyl,
  3,4-dimethylphenyl, 3,4-ditrifluoromethylphenyl,
  3,4-dimethoxyphenyl, 3,4-ditrifluoromethoxyphenyl,
  2,4,6-trichlorophenyl, 2,4,6-trifluorophenyl,
  2,4,6-trimethylphenyl, 2,4,6-tritrifluoromethylphenyl, 2,4,6-trimethoxyphenyl, 2,4,6-tritrifluoromethoxyphenyl,
2-chloro-4-CF$_3$-phenyl, 2-fluoro-3-chloro-phenyl,
2-chloro-4-CF$_3$-phenyl, 2-chloro-4-methoxy-phenyl,
2-methoxy-4-isopropyl-phenyl, 2-CF$_3$-4-methoxy-phenyl,
2-methyl-4-methoxy-5-fluoro-phenyl,
2-methyl-4-methoxy-phenyl, 2-chloro-4-CF$_3$O-phenyl,
2,4,5-trimethyl-phenyl, 2-methyl-4-chloro-phenyl,
methyl-C(=O)NH—, ethyl-C(=O)NH—, propyl-C(=O)NH—,
isopropyl-C(=O)NH—, butyl-C(=O)NH—, phenyl-C(=O)NH—,
4-acetylphenyl, 3-acetamidophenyl, 4-pyridyl, 2-furanyl, 2-thiophenyl, 2-naphthyl;
2-Me-5-F-phenyl, 2-F-5-Me-phenyl, 2-MeO-5-F-phenyl,
2-Me-3-Cl-phenyl, 3-NO$_2$-phenyl, 2-NO$_2$-phenyl,
2-Cl-3-Me-phenyl, 2-Me-4-EtO-phenyl, 2-Me-4-F-phenyl,
2-Cl-6-F-phenyl, 2-Cl-4-(CHF$_2$)O-phenyl,
2,4-diMeO-6-F-phenyl, 2-CF$_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-CF$_3$-4-EtO-phenyl, 2-CF$_3$-4-iPrO-phenyl,
2-CF$_3$-4-Cl-phenyl, 2-CF$_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH$_3$CH(OH)-4-MeO-phenyl,
2-CH$_3$CH(OH)-4-F-phenyl, 2-CH$_3$CH(OH)-4-Cl-phenyl,
2-CH$_3$CH(OH)-4-Me-phenyl, 2-CH$_3$CH(OMe)-4-MeO-phenyl,
2-CH$_3$C(=O)-4-MeO-phenyl, 2-CH$_3$C(=O)-4-F-phenyl,
2-CH$_3$C(=O)-4-Cl-phenyl, 2-CH$_3$C(=O)-4-Me-phenyl,
2-H$_2$C(OH)-4-MeO-phenyl, 2-H$_2$C(OMe)-4-MeO-phenyl,
2-H$_3$CCH$_2$CH(OH)-4-MeO-phenyl, 2-H$_3$CCH$_2$C(=O)-4-MeO-phenyl,
2-CH$_3$CO$_2$CH$_2$CH$_2$-4-MeO-phenyl,
(Z)-2-HOCH$_2$CH=CH-4-MeO-phenyl,
(E)-2-HOCH$_2$CH=CH-4-MeO-phenyl,
(Z)-2-CH$_3$CO$_2$CH=CH-4-MeO-phenyl,
(E)-2-CH$_3$CO$_2$CH=CH-4-MeO-phenyl,
2-CH$_3$OCH$_2$CH$_2$-4-MeO-phenyl,
2-F-4-MeO-phenyl, 2-Cl-4-F-phenyl,
(2-Cl-phenyl)-CH=CH—, (3-Cl-phenyl)-CH=CH—,
(2,6-diF-phenyl)-CH=CH—, —CH$_2$CH=CH$_2$,
phenyl-CH=CH—, (2-Me-4-MeO-phenyl)-CH=CH—,
cyclohexyl, cyclopentyl, cyclohexylmethyl,
EtCO$_2$CH$_2$CH$_2$—, EtCO$_2$CH$_2$CH$_2$CH$_2$—, EtCO$_2$CH$_2$CH$_2$CH$_2$CH$_2$—,
benzyl, 2-F-benzyl, 3-F-benzyl, 4-F-benzyl,
3-MeO-benzyl, 3-OH-benzyl, 2-MeO-benzyl,
2-OH-benzyl, 2-MeOC(=O)-3-MeO-phenyl,
2-Me-4-CN-phenyl, 2-Me-3-CN-phenyl,
2-Me-4-MeS-phenyl, 2-CF$_3$-4-CN-phenyl,
2-CHO-phenyl, 3-CHO-phenyl, 2-HOCH$_2$-phenyl,
3-HOCH$_2$-phenyl, 3-MeOCH$_2$-phenyl,
3-Me$_2$NCH$_2$-phenyl, 3-CN-4-F-phenyl,
2-Me-4-H$_2$NCO-phenyl, 2-Me-4-MeOC(=O)-phenyl,
3-H$_2$NCO-4-F-phenyl, 2-Me$_2$NCH$_2$-4-MeO-phenyl-,
2-Me-4-CH$_3$C(=O)-phenyl, phenyl-S—, Me$_2$N—,
1-pyrrolidinyl,
phenyl-NH—, benzyl-NH—, (1-naphthyl)-NH—,
(2-naphthyl)-NH—, (2-[1,1'-biphenyl])-NH—,
(3-[1,1'-biphenyl])-NH—, (4-[1,1'-biphenyl])-NH—,
(2-F-phenyl)-NH—, (2-Cl-phenyl)-NH—,
(2-CF$_3$-phenyl)-NH—, (2-CH$_3$-phenyl)-NH—,
(2-OMe-phenyl)-NH—, (2-CN-phenyl)-NH—,
(2-OCF$_3$-phenyl)-NH—, (2-SMe-phenyl)-NH—,
(3-F-phenyl)-NH—, (3-Cl-phenyl)-NH—,
(3-CF$_3$-phenyl)-NH—, (3-CH$_3$-phenyl)-NH—,
(3-OMe-phenyl)-NH—, (3-CN-phenyl)-NH—,
(3-OCF$_3$-phenyl)-NH—, (3-SMe-phenyl)-NH—,
(4-F-phenyl)-NH—, (4-Cl-phenyl)-NH—,
(4-CF$_3$-phenyl)-NH—, (4-CH$_3$-phenyl)-NH—,
(4-OMe-phenyl)-NH—, (4-CN-phenyl)-NH—,
(4-OCF$_3$-phenyl)-NH—, (4-SMe-phenyl)-NH—,
(2,3-diCl-phenyl)-NH—, (2,4-diCl-phenyl)-NH—,
(2,5-diCl-phenyl)-NH—, (2,6-diCl-phenyl)-NH—,
(3,4-diCl-phenyl)-NH—, (3,5-diCl-phenyl)-NH—,
(2,3-diF-phenyl)-NH—, (2,4-diF-phenyl)-NH—,
(2,5-diF-phenyl)-NH—, (2,6-diF-phenyl)-NH—,
(3,4-diF-phenyl)-NH—, (3,5-diF-phenyl)-NH—,
(2,3-diCH$_3$-phenyl)-NH—, (2,4-diCH$_3$-phenyl)-NH—,
(2,5-diCH$_3$-phenyl)-NH—, (2,6-diCH$_3$-phenyl)-NH—,
(3,4-diCH$_3$-phenyl)-NH—, (3,5-diCH$_3$-phenyl)-NH—,
(2,3-diCF$_3$-phenyl)-NH—, (2,4-diCF$_3$-phenyl)-NH—,
(2,5-diCF$_3$-phenyl)-NH—, (2,6-diCF$_3$-phenyl)-NH—,
(3,4-diCF$_3$-phenyl)-NH—, (3,5-diCF$_3$-phenyl)-NH—,
(2,3-dioMe-phenyl)-NH—, (2,4-dioMe-phenyl)-NH—,
(2,5-dioMe-phenyl)-NH—, (2,6-dioMe-phenyl)-NH—,
(3,4-dioMe-phenyl)-NH—, (3,5-dioMe-phenyl)-NH—,
(2-F-3-Cl-phenyl)-NH—, (2-F-4-Cl-phenyl)-NH—,
(2-F-5-Cl-phenyl)-NH—, (2-F-6-Cl-phenyl)-NH—,
(2-F-3-CH$_3$-phenyl)-NH—, (2-F-4-CH$_3$-phenyl)-NH—,
(2-F-5-CH$_3$-phenyl)-NH—, (2-F-6-CH$_3$-phenyl)-NH—,
(2-F-3-CF$_3$-phenyl)-NH—, (2-F-4-CF$_3$-phenyl)-NH—,
(2-F-5-CF$_3$-phenyl)-NH—, (2-F-6-CF$_3$-phenyl)-NH—,
(2-F-3-OMe-phenyl)-NH—, (2-F-4-OMe-phenyl)-NH—,
(2-F-5-OMe-phenyl)-NH—, (2-F-6-OMe-phenyl)-NH—,
(2-Cl-3-F-phenyl)-NH—, (2-Cl-4-F-phenyl)-NH—,
(2-Cl-5-F-phenyl)-NH—, (2-Cl-6-F-phenyl)-NH—,
(2-Cl-3-CH$_3$-phenyl)-NH—, (2-Cl-4-CH$_3$-phenyl)-NH—,
(2-Cl-5-CH$_3$-phenyl)-NH—, (2-Cl-6-CH$_3$-phenyl)-NH—,
(2-Cl-3-CF$_3$-phenyl)-NH—, (2-Cl-4-CF$_3$-phenyl)-NH—,
(2-Cl-5-CF$_3$-phenyl)-NH—, (2-Cl-6-CF$_3$-phenyl)-NH—,
(2-Cl-3-OMe-phenyl)-NH—, (2-Cl-4-OMe-phenyl)-NH—,
(2-Cl-5-OMe-phenyl)-NH—, (2-Cl-6-OMe-phenyl)-NH—,
(2-CH$_3$-3-F-phenyl)-NH—, (2-CH$_3$-4-F-phenyl)-NH—,
(2-CH$_3$-5-F-phenyl)-NH—, (2-CH$_3$-6-F-phenyl)-NH—, (2-CH₃-3-Cl-phenyl)-NH—, (2-CH₃-4-Cl-phenyl)-NH—,
(2-CH₃-5-Cl-phenyl)-NH—, (2-CH₃-6-Cl-phenyl)-NH—,
(2-CH₃-3-CF₃-phenyl)-NH—, (2-CH₃-4-CF₃-phenyl)-NH—,
(2-CH₃-5-CF₃-phenyl)-NH—, (2-CH₃-6-CF₃-phenyl)-NH—,
(2-CH₃-3-OMe-phenyl)-NH—, (2-CH₃-4-OMe-phenyl)-NH—,
(2-CH₃-5-OMe-phenyl)-NH—, (2-CH₃-6-OMe-phenyl)-NH—,
(2-CF₃-3-F-phenyl)-NH—, (2-CF₃-4-F-phenyl)-NH—,
(2-CF₃-5-F-phenyl)-NH—, (2-CF₃-6-F-phenyl)-NH—,
(2-CF₃-3-Cl-phenyl)-NH—, (2-CF₃-4-Cl-phenyl)-NH—,
(2-CF₃-5-Cl-phenyl)-NH—, (2-CF₃-6-Cl-phenyl)-NH—,
(2-CF₃-3-CH₃-phenyl)-NH—, (2-CF₃-4-CH₃-phenyl)-NH—,
(2-CH₃-5-CF₃-phenyl)-NH—, (2-CF₃-6-CH₃-phenyl)-NH—,
(2-CF₃-3-OMe-phenyl)-NH—, (2-CF₃-4-OMe-phenyl)-N—,
(2-CF₃-5-OMe-phenyl)-NH—, (2-CF₃-6-OMe-phenyl)-NH—,
(2-OMe-3-F-phenyl)-NH—, (2-OMe-4-F-phenyl)-NH—,
(2-OMe-5-F-phenyl)-NH—, (2-OMe-6-F-phenyl)-NH—,
(2-OMe-3-Cl-phenyl)-NH—, (2-OMe-4-Cl-phenyl)-NH—,
(2-OMe-5-Cl-phenyl)-NH—, (2-OMe-6-Cl-phenyl)-NH—,
(2-OMe-3-CH₃-phenyl)-NH—, (2-OMe-4-CH₃-phenyl)-NH—,
(2-OMe-5-CH₃-phenyl)-NH—, (2-OMe-6-CH₃-phenyl)-NH—,
(2-OMe-3-CF₃-phenyl)-NH—, (2-OMe-4-CF₃-phenyl)-NH—,
(2-OMe-5-CF₃-phenyl)-NH—, (2-OMe-6-CF₃-phenyl)-NH—
(3-CF₃-4-Cl-phenyl)-NH—, (3-CF₃-4-C(O)CH₃-phenyl)-NH—,
(2,3,5-triCl-phenyl)-NH—, (3-CH₃-4-CO₂Me-phenyl)-NH—, and
(3-CHO-4-OMe-phenyl)-NH—.

[11] In another embodiment, the present invention provides a novel compound of Formula (I):

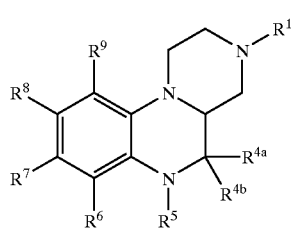

(I)

or a stereoisomer or a pharmaceutically acceptable salt form thereof, wherein:

R¹ is selected from
C₁₋₆ alkyl substituted with Z,
C₂₋₆ alkenyl substituted with Z,
C₂₋₆ alkynyl substituted with Z,
C₃₋₆ cycloalkyl substituted with Z,
aryl substituted with Z,
5–6 membered heterocyclic ring system containing at least one heteroatom selected from the group consisting of N, O, and S, said heterocyclic ring system substituted with Z;
C₁₋₆ alkyl substituted with 0–2 R²,
C₂₋₆ alkenyl substituted with 0–2 R²,
C₂₋₆ alkynyl substituted with 0–2 R²,
aryl substituted with 0–2 R², and
5–6 membered heterocyclic ring system containing at least one heteroatom selected from the group consisting of N, O, and S, said heterocyclic ring system substituted with 0–2 R²;

Z is selected from H,
—CH(OH)R²,
—C(ethylenedioxy)R²,
—OR²,
—SR²,
—NR²R³,
—C(O) R²,
—C(O)NR²R³,
—NR³C(O)R²,
—C(O)OR²,
—OC(O)R²,
—CH(=NR⁴)NR²R³,
—NHC(=NR⁴)NR²R³,
—S(O) R²,
—S(O)₂R²,
—S(O)₂NR²R³, and —NR³S(O)₂R²;

R², at each occurrence, is independently selected from
C₁₋₄ alkyl,
C₂₋₄ alkenyl,
C₂₋₄ alkynyl,
C₃₋₆ cycloalkyl,
aryl substituted with 0–5 R⁴²;
C₃₋₁₀ carbocyclic residue substituted with 0–3 R⁴¹, and
5–10 membered heterocyclic ring system containing from 1–4 heteroatoms selected from the group consisting of N, O, and S substituted with 0–3 R⁴¹;

R³, at each occurrence, is independently selected from H, C₁₋₄ alkyl, C₂₋₄ alkenyl, C₂₋₄ alkynyl, and C₁₋₄ alkoxy; alternatively, R² and R³ join to form a 5- or 6-membered ring optionally substituted with —O— or —N(R⁴)—;

R⁴, at each occurrence, is independently selected from H, methyl, ethyl, propyl, and butyl;

R⁴ᵃ is H or C₁₋₄ alkyl;

R⁴ᵇ is H;

alternatively, R⁴ᵃ and R⁴ᵇ are taken together to form =O or =S;

R⁵ is H or C₁₋₄ alkyl;

R⁶ is H or C₁₋₄ alkyl;

alternatively, R⁵ and R⁶ are taken together to form a fused heterocyclic ring of formula:

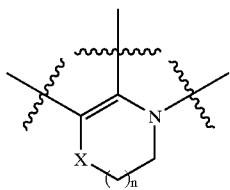

wherein:

X is a bond, —CH$_2$—, —O—, —S—, —S(=O)—, —S(=O)$_2$—, —NR$^{10}$—, —CH$_2$CH$_2$—, —OCH$_2$—, —SCH$_2$—, —CH$_2$O—, —CH$_2$S—, —CH$_2$NR$^{10}$—, —NR$^{10}$OCH$_2$—, —NHC(=O)—, or —C(=O)NH—; and n is 1 or 2;

R$^7$, R$^8$, and R$^9$, at each occurrence, are independently selected from

H, halo, —CF$_3$, —OCF$_3$, —OH, —CN, —NO$_2$, —NR$^{46}$R$^{47}$,

C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy, C$_{1-4}$ alkyl substituted with 0–2 R$^{11}$, C$_{3-10}$ carbocyclic residue substituted with 0–3 R$^{33}$, aryl substituted with 0–5 R$^{33}$, 5–10 membered heterocyclic ring system containing from 1–4 heteroatoms selected from the group consisting of N, O, and S substituted with 0–3 R$^{31}$;

OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$,

S(O)NR$^{12}$R$^{13}$, S(O)$_2$NR$^{12}$R$^{13}$, NR$^{14}$S(O)R$^{12}$, NR$^{14}$S(O)$_2$R$^{12}$,

NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{10}$ is selected from H, C$_{1-4}$ alkyl, C$_{2-4}$ alkenyl, C$_{2-4}$ alkynyl, and C$_{1-4}$ alkoxy;

R$^{11}$ is selected from

H, halo, —CF$_3$, —CN, —NO$_2$,

C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl, C$_{3-10}$ carbocyclic reside substituted with 0–3 R$^{33}$, aryl substituted with 0–5 R$^{33}$, 5–10 membered heterocyclic ring system containing from 1–4 heteroatoms selected from the group consisting of N, O, and S substituted with 0–3 R$^{31}$;

OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, and NR$^{14}$S(O)$_2$R$^{12}$;

R$^{12}$, at each occurrence, is independently selected from

C$_{1-4}$ alkyl,

C$_{2-4}$ alkenyl,

C$_{2-4}$ alkynyl,

C$_{3-6}$ cycloalkyl, aryl substituted with 0–5 R$^{33}$;

C$_{3-10}$ carbocyclic residue substituted with 0–3 R$^{33}$, and

5–10 membered heterocyclic ring system containing from 1–4 heteroatoms selected from the group consisting of N, O, and S substituted with 0–3 R$^{31}$;

R$^{13}$, at each occurrence, is independently selected from H, C$_{1-4}$ alkyl, C$_{2-4}$ alkenyl, and C$_{2-4}$ alkynyl;

alternatively, R$^{12}$ and R$^{13}$ join to form a 5- or 6-membered ring optionally substituted with —O— or —N(R$^{14}$)—;

R$^{14}$, at each occurrence, is independently selected from H and C$_{1-4}$ alkyl;

R$^{31}$, at each occurrence, is independently selected from

H, OH, halo, CF$_3$, SO$_2$R$^{45}$, NR$^{46}$R$^{47}$, methyl, ethyl, and propyl;

R$^{33}$, at each occurrence, is independently selected from

H, OH, halo, CN, NO$_2$, CF$_3$, SO$_2$R$^{45}$, NR$^{46}$R$^{47}$,

C$_{1-3}$ alkyl, C$_{2-3}$ alkenyl, C$_{2-3}$ alkynyl, C$_{3-5}$ cycloalkyl, C$_{1-3}$ haloalkyl, C$_{1-3}$ haloalkyl-oxy-, C$_{1-3}$ alkyloxy-, C$_{1-3}$ alkylthio-, C$_{1-3}$ alkyl-C(=O)—, and C$_{1-3}$ alkyl-C(=O)NH—;

R$^{41}$, at each occurrence, is independently selected from

H, CF$_3$, halo, OH, CO$_2$H, SO$_2$R$^{45}$, NR$^{46}$R$^{47}$, NO$_2$, CN, =O, C$_{2-8}$ alkenyl, C$_{2-8}$ alkynyl, C$_{1-4}$ alkoxy, C$_{1-4}$ haloalkyl C$_{1-4}$ alkyl substituted with 0–1 R$^{43}$, aryl substituted with 0–3 R$^{42}$, and 5–10 membered heterocyclic ring system containing from 1–4 heteroatoms selected from the group consisting of N, O, and S substituted with 0–3 R$^{44}$;

R$^{42}$, at each occurrence, is independently selected from

H, CF$_3$, halo, OH, CO$_2$H, SO$_2$R$^{45}$, SR$^{45}$, NR$^{46}$R$^{47}$, OR$^{48}$, NO$_2$, CN, CH(=NH)NH$_2$, NHC(=NH)NH$_2$, C$_{2-6}$ alkenyl, C$_{2-6}$ alkynyl, C$_{1-4}$ alkoxy, C$_{1-4}$ haloalkyl, C$_{3-6}$ cycloalkyl, C$_{1-4}$ alkyl substituted with 0–1 R$^{43}$, aryl substituted with 0–3 R$^{44}$, and 5–10 membered heterocyclic ring system containing from 1–4 heteroatoms selected from the group consisting of N, O, and S substituted with 0–3 R$^{44}$.

R$^{43}$ is C$_{3-6}$ cycloalkyl or aryl substituted with 0–3 R$^{44}$;

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, C$_{1-4}$ alkyl, and C$_{1-4}$ alkoxy;

R$^{45}$ is C$_{1-4}$ alkyl;

R$^{46}$, at each occurrence, is independently selected from H and C$_{1-4}$ alkyl;

R$^{47}$, at each occurrence, is independently selected from H, C$_{1-4}$ alkyl, —C(=O)NH(C$_{1-4}$ alkyl), —SO$_2$(C$_{1-4}$ alkyl), —SO$_2$(phenyl), —C(=O)O(C$_{1-4}$ alkyl), —C(=O) (C$_{1-4}$ alkyl), and —C(=O)H; and R$^{48}$, at each occurrence, is independently selected from H, C$_{1-4}$ alkyl, —C(=O)NH(C$_{1-4}$ alkyl), —C(=O)O(C$_{1-4}$ alkyl), —C(=O) (C$_{1-4}$ alkyl), and —C(=O)H;

provided when R$^5$ is H or C$_{1-4}$ alkyl; and R$^6$ is H or C$_{1-4}$ alkyl; then R$^1$ is not C$_{1-6}$ alkyl.

[12] In another embodiment, the present invention provides a novel compound of Formula (I):

R1 is selected from ethyl substituted with Z, propyl substituted with Z, butyl substituted with Z, propenyl substituted with Z, butenyl substituted with Z, ethyl substituted with R$^2$, propyl substituted with R$^2$, butyl substituted with R$^2$, propenyl substituted with R$^2$, and butenyl substituted with R$^2$;

Z is selected from H,
—CH(OH)R$^2$,
—OR$^2$,
—SR$^2$,
—NR$^2$R$^3$,
—C(O)R$^2$,
—C(O)NR$^2$R$^3$,
—NR$^3$C(O)R$^2$,
—C(O)OR$^2$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
phenyl substituted with 0–3 R$^{42}$;
naphthyl substituted with 0–3 R$^{42}$;
cyclopropyl substituted with 0–3 R$^{41}$;
cyclobutyl substituted with 0–3 R$^{41}$;
cyclopentyl substituted with 0–3 R$^{41}$;
cyclohexyl substituted with 0–3 R$^{41}$;
pyridyl substituted with 0–3 R$^{41}$;
indolyl substituted with 0–3 R$^{41}$;
indolinyl substituted with 0–3 R$^{41}$;
benzimidazolyl substituted with 0–3 R$^{41}$;
benzotriazolyl substituted with 0–3 R$^{41}$;
benzothienyl substituted with 0–3 R$^{41}$;
benzofuranyl substituted with 0–3 R$^{41}$;
phthalimid-1-yl substituted with 0–3 R$^{41}$;
inden-2-yl substituted with 0–3 R$^{41}$;
2,3-dihydro-1H-inden-2-yl substituted with 0–3 R$^{41}$;
indazolyl substituted with 0–3 R$^{41}$;
tetrahydroquinolinyl substituted with 0–3 R$^{41}$; and
tetrahydro-isoquinolinyl substituted with 0–3 R$^{41}$;

R$^3$, at each occurrence, is independently selected from H, methyl, and ethyl;
R$^{4a}$ is H or C$_{1-4}$ alkyl;
R$^{4b}$ is H;
alternatively, R$^{4a}$ and R$^{4b}$ are taken together to form =O;
R$^5$ is H or C$_{1-4}$ alkyl;
R$^6$ is H or C$_{1-4}$ alkyl;
alternatively, R$^5$ and R$^6$ are taken together to form a fused heterocyclic ring of formula:

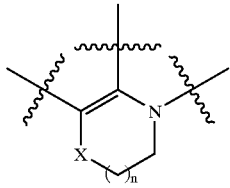

wherein:
X is —CH$_2$—, —O—, or —S—; and
n is 1;
R$^7$, R$^8$, and R$^9$, at each occurrence, are independently selected from H, F, Cl, methyl, ethyl, methoxy, —CF$_3$, and —OCF$_3$;
R$^{41}$, at each occurrence, is independently selected from H, F, Cl, Br, OH, CF$_3$, NO$_2$, CN, =O, methyl, ethyl, propyl, butyl, methoxy, and ethoxy;
R$^{42}$, at each occurrence, is independently selected from H, F, Cl, Br, OH, CF$_3$, SO$_2$R$^{45}$, SR$^{45}$, NR$^{46}$R$^{47}$, OR$^{48}$, NO$_2$, CN, =O, methyl, ethyl, propyl, butyl, methoxy, and ethoxy;

R$^{45}$ is methyl, ethyl, propyl, or butyl;
R$^{46}$, at each occurrence, is independently selected from H, methyl, ethyl, propyl, and butyl;
R$^{47}$, at each occurrence, is independently selected from H, methyl, ethyl, n-propyl, i-propyl, n-butyl, i-butyl, —C(=O)NH(methyl), —C(=O)NH(ethyl), —SO$_2$(methyl), —SO$_2$(ethyl), —SO$_2$(phenyl), —C(=O)O(methyl), —C(=O)O(ethyl), —C(=O)(methyl), —C(=O)(ethyl), and —C(=O)H;
R$^{48}$, at each occurrence, is independently selected from H, methyl, ethyl, n-propyl, i-propyl, —C(=O)NH(methyl), —C(=O)NH(ethyl), —C(=O)O(methyl), —C(=O)O (ethyl), —C(=O) (methyl), —C(=O) (ethyl), and —C(=O)H.

[13] In another embodiment, the present invention provides a novel compound of Formula (I):
R$^1$ is selected from
—(CH$_2$)$_3$C(=O) (4-fluoro-phenyl),
—(CH$_2$)$_3$C(=O) (4-bromo-phenyl),
—(CH$_2$)$_3$C(=O) (4-methyl-phenyl),
—(CH$_2$)$_3$C(=O) (4-methoxy-phenyl),
—(CH$_2$)$_3$C(=O) (4-(3,4-dichloro-phenyl)phenyl),
—(CH$_2$)$_3$C(=O) (3-methyl-4-fluoro-phenyl),
—(CH$_2$)$_3$C(=O) (2,3-dimethoxy-phenyl),
—(CH$_2$)$_3$C(=O) (phenyl),
—(CH$_2$)$_3$C(=O) (4-chloro-phenyl),
—(CH$_2$)$_3$C(=O) (3-methyl-phenyl),
—(CH$_2$)$_3$C(=O) (4-t-butyl-phenyl),
—(CH$_2$)$_3$C(=O) (3,4-difluoro-phenyl),
—(CH$_2$)$_3$C(=O) (2-methoxy-5-fluoro-phenyl),
—(CH$_2$)$_3$C(=O) (4-fluoro-1-naphthyl),
—(CH$_2$)$_3$C(=O) (benzyl),
—(CH$_2$)$_3$C(=O) (4-pyridyl),
—(CH$_2$)$_3$C(=O) (3-pyridyl),
—(CH$_2$)$_3$CH (OH) (4-fluoro-phenyl),
—(CH$_2$)$_3$CH (OH) (4-pyridyl),
—(CH$_2$)$_3$CH (OH) (2,3-dimethoxy-phenyl),
—(CH$_2$)$_3$S(3-fluoro-phenyl),
—(CH$_2$)$_3$S(4-fluoro-phenyl),
—(CH$_2$)$_3$S(=O) (4-fluoro-phenyl),
—(CH$_2$)$_3$SO$_2$(3-fluoro-phenyl),
—(CH$_2$)$_3$SO$_2$(4-fluoro-phenyl),
—(CH$_2$)$_3$O(4-fluoro-phenyl),
—(CH$_2$)$_3$O(phenyl),
—(CH$_2$)$_3$O(3-pyridyl),
—(CH$_2$)$_3$O(4-pyridyl),
—(CH$_2$)$_3$O(2-NH$_2$-phenyl),
—(CH$_2$)$_3$O(2-NH$_2$-5-F-phenyl),
—(CH$_2$)$_3$O(2-NH$_2$-4-F-phenyl)
—(CH$_2$)$_3$O(2-NH$_2$-3-F-phenyl)
—(CH$_2$)$_3$O(2-NH$_2$-4-Cl-phenyl),
—(CH$_2$)$_3$O(2-NH$_2$-4-OH-phenyl),
—(CH$_2$)$_3$O(2-NH$_2$-4-Br-phenyl),
—(CH$_2$)$_3$O(2-NHC(=)Me-4-F-phenyl),
—(CH$_2$)$_3$O(2-NHC (=O) Me-phenyl),
—(CH$_2$)$_3$NH(4-fluoro-phenyl),
—(CH$_2$)$_3$N(methyl) (4-fluoro-phenyl),
—(CH$_2$)$_3$CO$_2$(ethyl),
—(CH$_2$)$_3$C(=O)N(methyl) (methoxy), —(CH₂)₃C(=O)NH(4-fluoro-phenyl),
—(CH₂)₂NHC(=O) (phenyl),
—(CH₂)₂NMeC(=O) (phenyl),
—(CH₂)₂NHC(=O) (2-fluoro-phenyl),
—(CH₂)₂NMeC(=O) (2-fluoro-phenyl),
—(CH₂)₂NHC(=O) (4-fluoro-phenyl),
—(CH₂)₂NMeC(=O) (4-fluoro-phenyl),
—(CH₂)₂NHC(=O) (2,4-difluoro-phenyl),
—(CH₂)₂NMeC(=O) (2,4-difluoro-phenyl),
—(CH₂)₃(3-indolyl),
—(CH₂)₃(1-methyl-3-indolyl),
—(CH₂)₃(1-indolyl),
—(CH₂)₃(1-indolinyl),
—(CH₂)₃(1-benzimidazolyl),
—(CH₂)₃(1H-1,2,3-benzotriazol-1-yl),
—(CH₂)₃(1H-1,2,3-benzotriazol-2-yl),
—(CH₂)₃(1H-1,2,3-benzotriazol-1-yl),
—(CH₂)₃(1H-1,2,3-benzotriazol-2-yl),
—(CH₂)₃(3,4 dihydro-1(2H)-quinolinyl),
—(CH₂)₂C(=O) (4-fluoro-phenyl),
—(CH₂)₂C(=O)NH(4-fluoro-phenyl),
—CH₂CH₂(3-indolyl),
—CH₂CH₂(1-phthalimidyl),
—(CH₂)₄C(=O)N(methyl) (methoxy),
—(CH₂)₄CO₂(ethyl),
—(CH₂)₄C(=O) (phenyl),
—(CH₂)₄ (cyclohexyl),
—(CH₂)₃CH(phenyl)₂,
—CH₂CH₂CH=C(phenyl)₂,
—CH₂CH₂CH=CMe(4-F-phenyl),
—(CH₂)₃CH(4-fluoro-phenyl)₂,
—CH₂CH₂CH=C(4-fluoro-phenyl)₂,
—(CH₂)₂(2,3-dihydro-1H-inden-2-yl),
—(CH₂)₃C(=O) (2-NH₂-phenyl),
—(CH₂)₃C(=O)(2-NH₂-5-F-phenyl),
—(CH₂)₃C(=O) (2-NH₂-4-F-phenyl),
—(CH₂)₃C(=O) (2-NH₂-3-F-phenyl),
—(CH₂)₃C(=O) (2-NH₂-4-Cl-phenyl),
—(CH₂)₃C(=O) (2-NH₂-4-OH-phenyl),
—(CH₂)₃C(=O) (2-NH₂-4-Br-phenyl),
—(CH₂)₃(1H-indazol-3-yl),
—(CH₂)₃(5-F-1H-indazol-3-yl),
—(CH₂)₃(7-F-1H-indazol-3-yl),
—(CH₂)₃(6-Cl-1H-indazol-3-yl),
—(CH₂)₃(6-Br-1H-indazol-3-yl)
—(CH₂)₃C(=O) (2-NHMe-phenyl),
—(CH₂)₃(1-benzothien-3-yl),
—(CH₂)₃(6-F-1H-indol-1-yl),
—(CH₂)₃(5-F-1H-indol-1-yl),
—(CH₂)₃(6-F-2,3-dihydro-1H-indol-1-yl),
—(CH₂)₃(5-F-2,3-dihydro-1H-indol-1-yl),
—(CH₂)₃(6-F-1H-indol-3-yl),
—(CH₂)₃(5-F-1H-indol-3-yl),
—(CH₂)₃(5-F-1H-indol-3-yl),
—(CH₂)₃(9H-purin-9-yl),
—(CH₂)₃(7H-purin-7-yl),
—(CH₂)₃(6-F-1H-indazol-3-yl),
—(CH₂)₃C(=O) (2-NHSO₂Me-4-F-phenyl),
—(CH₂)₃C(=O) (2-NHC(=O)Me-4-F-phenyl),
—(CH₂)₃C(=O) (2-NHC(=O)Me-phenyl),
—(CH₂)₃C(=O) (2-NHCO₂Et-4-F-phenyl),
—(CH₂)₃C(=O) (2-NHC(=O)NHEt-4-F-phenyl),
—(CH₂)₃C(=O) (2-NHCHO-4-F-phenyl),
—(CH₂)₃C(=O) (2-OH-4-F-phenyl),
—(CH₂)₃C(=O) (2-MeS-4-F-phenyl),
—(CH₂)₃C(=O) (2-NHSO₂Me-4-F-phenyl),
—(CH₂)₂C(Me)CO₂Me,
—(CH₂)₂C(Me)CH(OH) (4-F-phenyl)₂,
—(CH₂)₂C(Me)CH(OH) (4-Cl-phenyl)₂,
—(CH₂)₂C(Me)C(=O) (4-F-phenyl),
—(CH₂)₂C(Me)C(=O) (2-MeO-4-F-phenyl),
—(CH₂)₂C(Me)C(=O) (3-Me-4-F-phenyl),
—(CH₂)₂C(Me)C(=O) (2-Me-phenyl),
—(CH₂)₂C(Me)C(=O)phenyl,

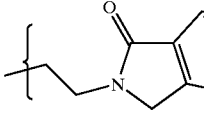, 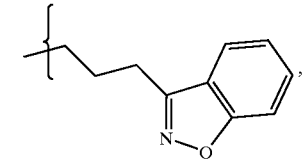,

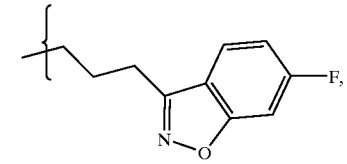

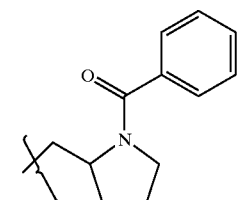, 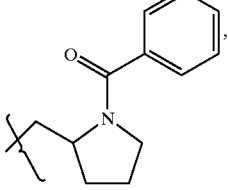,

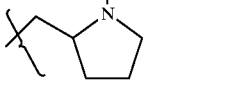

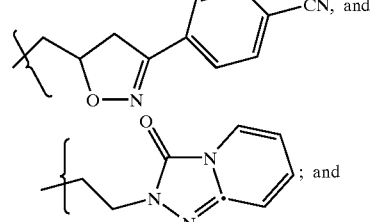; and

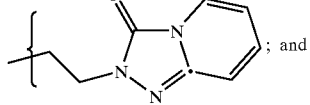

$R^{4a}$ is H;

$R^{4b}$ is H;

alternatively, $R^{4a}$ and $R^{4b}$ are taken together to form =O;

$R^5$ is H, methyl, ethyl, propyl, or butyl;

$R^6$ is H, methyl, ethyl, propyl, or butyl;

alternatively, $R^5$ and R6 are taken together to form a fused heterocyclic ring of formula:

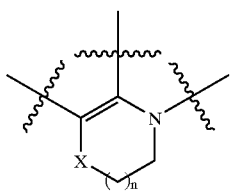

wherein:

X is —CH₂—, —O—, or —S—; and n is 1;

R⁷, R⁸, and R⁹, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, benzyl, HC(=O)—, methylC(=O)—, ethylC(=O)—, propylC(=O)—, isopropylC(=O)—, n-butylC(=O)—, isobutylC(=O)—, secbutylC(=O)—, tertbutylC(=O)—, phenylC(=O)—, methylC(=O)NH—, ethylC(=O)NH—, propylC(=O)NH—, isopropylC(=O)NH—, n-butylC(=O)NH—, isobutylC(=O)NH—, secbutylC(=O)NH—, tertbutylC(=O)NH—, phenylC(=O)NH—, methylamino-, ethylamino-, propylamino-, isopropylamino-, n-butylamino-, isobutylamino-, secbutylamino-, tertbutylamino-, phenylamino-, provided that two of substituents R⁷, R⁸, and R⁹, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy.

In an even further more preferred embodiment of the present invention, are compounds of Formula (I) selected from disclosed Examples 1–8.

In a second embodiment, the present invention provides a pharmaceutical composition comprising a compound of Formula (I) and a pharmaceutically acceptable carrier.

In a third embodiment, the present invention provides a method for the treatment a central nervous system disorder comprising administering to a host in need of such treatment a therapeutically effective amount of a compound of Formula (I), or a pharmaceutically acceptable salt thereof, wherein the compound is a 5HT2a antagonist or a 5HT2c agonist.

In a preferred embodiment the compound is a 5HT2a antagonist.

In another preferred embodiment the compound is a 5HT2c agonist.

In a more preferred embodiment the present invention provides a method for the treatment central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility comprising administering to a host in need of such treatment a therapeutically effective amount of a compound of Formula (I).

In a further preferred embodiment the central nervous system disorder comprises obesity.

In another further preferred embodiment the central nervous system disorder comprises schizophrenia.

In another further preferred embodiment the central nervous system disorder comprises depression.

In another further preferred embodiment the central nervous system disorder comprises anxiety.

In a fourth embodiment the present invention provides novel compounds of Formula (I) or pharmaceutically acceptable salt forms thereof for use in therapy.

In a fifth embodiment the present invention provides the use of novel compounds of Formula (I) or pharmaceutically acceptable salt forms thereof for the manufacture of a medicament for the treatment of central nervous system disorders including obesity, anxiety, depression, psychosis, schizophrenia, sleep disorders, sexual disorders, migraine, conditions associated with cephalic pain, social phobias, and gastrointestinal disorders.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g. $R^2$, $R^{11}$, $R^{33}$, $R^{41}$, $R^{42}$ etc.) occurs more than one time in any constituent or formula for a compound, its definition at each occurrence is independent of its definition at every other occurrence. Thus, for example, if a group is shown to be substituted with 0–2 $R^2$, then said group may optionally be substituted with up to two $R^2$ groups and $R^2$ at each occurrence is selected independently from the definition of $R^2$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" or "$C_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms, for example "$C_{2-6}$ alkenyl", and one or more unsaturated carbon—carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration, having the specified number of carbon atoms, for example "$C_{2-6}$ alkynyl", and one or more carbon—carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" is represents an alkyl group as defined above with the indicated number of carbon atoms attached through a sulpher bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic ring" or "heterocyclic ring system" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles.

As used herein, the term "bicyclic heterocyclic ring system" is intended to mean a stable 9- to 10-membered bicyclic heterocyclic ring formed from the substituent $NR^{12}R^{13}$, which is partially unsaturated or unsaturated (aromatic), and which consists of carbon atoms, a nitrogen atom, and 1 or 2 additional heteroatoms independently selected from the group consisting of N, O and S. The additional nitrogen or sulfur heteroatoms may optionally be oxidized. The heterocyclic ring is attached to its pendant group by the nitrogen atom of the group $NR^{12}R^{13}$ and for which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. The term "bicyclic heterocyclic ring system" is intended to be a subset of the term "heterocyclic ring system". Preferred examples of a 9- to 10-membered bicyclic heterocyclic ring system are benzimidazolyl, benzimidazolinyl, benzoxazolinyl, dihydrobenzthiazolyl, dihydrodioxobenzthiazolyl, benzisoxazolinyl, 1H-indazolyl, indolyl, indolinyl, isoindolinyl, tetrahydro-isoquinolinyl, tetrahydro-quinolinyl, and benzotriazolyl.

Additionally, a subclass of preferred heterocycles are heterocycles which function as an isostere of a cyclic but non-heterocyclic substitutent such as $-CH_2-C(=O)$-phenyl. Preferred examples of such heterocycles include, but are not limited to, benzimidazolyl, benzofuranyl, benzothiophenyl, benzoxazolyl, benzthiazolyl, benzisoxazolyl, furanyl, imidazolinyl, 1H-indazolyl, indolinyl, isoindolinyl, isoquinolinyl, oxazolyl, piperidinyl, pyrazinyl, pyridinyl, pyrimidinyl, quinolinyl, thiazolyl, thiophenyl, and 1,2,3-triazolyl.

As used herein, the term "aryl", or aromatic residue, is intended to mean an aromatic moiety containing six to ten carbon atoms, such as phenyl, pyridinyl and naphthyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like. "Stable compound" and "stable structure" are meant to indicate a compound that is sufficiently robust to survive isolation to a useful degree of purity from a reaction mixture, and formulation into an efficacious therapeutic agent.

SYNTHESIS

Throughout the details of the invention, the following abbreviations are used with the following meanings:

| Reagents: | |
|---|---|
| MCPBA | m-chloroperoxybenzoic acid |
| DIBAL | diisobutyl aluminum hydride |
| $Et_3N$ | triethylamine |
| TFA | trifluoroacetic acid |
| LAH | lithium aluminum hydride |
| NBS | N-bromo succinimide |
| Red-Al | Sodium bis (2-methoxyethoxy) aluminum hydride |
| $Pd_2dba_3$ | Tris (dibenzylideneacetone)dipalladium(0) |
| ACE-Cl | 2-chloroethylchloroformate |
| Solvents: | |
| THF | tetrahydrofuran |
| MeOH | methanol |
| EtOH | ethanol |
| EtOAc | ethyl acetate |
| HOAc | acetic acid |
| DMF | dimethyl formamide |
| DMSO | dimethyl sulfoxide |
| DME | dimethoxyethane |
| $Et_2O$ | diethylether |
| iPrOH | isopropanol |
| Others: | |
| Ar | aryl |
| Ph | phenyl |
| Me | methyl |
| Et | ethyl |
| NMR | nuclear magnetic resonance |
| MHz | megahertz |
| BOC | tert-butoxycarbonyl |
| CBZ | benzyloxycarbonyl |
| Bn | benzyl |
| Bu | butyl |
| Pr | propyl |
| cat. | catalytic |
| mL | milliliter |
| nM | nanometer |
| ppm | part per million |

| | |
|---|---|
| mmol | millimole |
| mg | milligram |
| g | gram |
| kg | kilogram |
| TLC | thin layer chromatography |
| HPLC | high pressure liquid chromatography |
| rt | room temperature |
| aq. | aqueous |
| sat. | saturated |

The preparation of compounds of Formula (I) and (I-a) of the present invention may be carried out in a convergent or sequential synthetic manner. Detailed synthetic preparations of the compounds of Formula (I) and (I-a) are shown in the following reaction schemes. The skills required in preparation and purification of the compounds of Formula (I) and (I-a) and the intermediates leading to these compounds are known to those skilled in the art. Purification procedures include, but are not limited to, normal or reverse phase chromatography, crystallization, and distillation.

Preferred methods for the preparation of the compounds of the present invention include, but are not limited to, those shown in the schemes and examples below. The substitutions are as described and defined in the claims. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of Formula (I) of this invention may be prepared as shown in Scheme 1. Thus, preparation of nitroaryl derivative (V) is accomplished by treatment of the protected ($R^1$=CBz) piperidine carboxylic acid (IV) and the nitrophenyl compound (III), where Z=Cl, Br, or F, with a suitable base, such as triethylamine, in an inert solvent, such as DMSO, at elevated temperatures (60–150° C.) Reduction of the nitro group is accomplished by a variety of methods, for example with Iron in acetic acid (see Hudlicky, M., "Reductions in Organic Chemistry", Ellis Horwood, Ltd., Chichester, UK, 1984). Subsequent heating at elevated temperatures effects cyclization to derivatives of type (VI). This lactam can be alkylated by treatment with a suitable base, such as sodium hydride, followed by addition of an alkyl halide, such as methyl iodide to afford derivatives of type (VII). Further elaboration of the aromatic ring can be accomplished by the following procedures. When R7=H, these derivatives (VI) or (VII) can be selectively brominated with NBS in DMF at 0° C. to afford bromoaryl derivatives of type (VIII). Those skilled in the art will recognize the utility of aryl bromides of type (VIII) in allowing for the coupling of this moiety with an arylboronic acid to afford biaryl derivatives of type (IX). This transformation, commonly known as a Suzuki coupling is utilized to afford many types of functionalized derivatives. For a review and leading references of palladium catalyzed cross coupling reactions, see Miyaura, N., Suzuki, A., Chem. Rev., 1995, 2457. One such procedure entails treatment of the aryl bromide (VIII) with a functionalized aryl boronic acid in the presence of a catalytic Pd(0) species, such as $Pd(PPh_3)_4$, $Pd(PPh_3)_2Cl_2$, $Pd(OAc)_2$, $Pd_2(dba)_3$ and a suitable ligand such as $PPh_3$, $AsPh_3$, etc., or other such Pd(O) catalyst, and a base such as $Na_2CO_3$ or $Et_3N$ in a suitable solvent such as DMF, toluene, THF, DME or the like, to afford the coupled derivative (IX). Alternately, reduction of the lactam carbonyl of (VIII) with a reducing agent such as Dibal or $BH_3$, followed by Suzuki coupling affords derivatives of type (X). In addition, formation of the aryl boronic acid from the bromine derivative (VIII) (i.e. (I, $R^7=B(OH)_2$)) would allow for greater diversity in the subsequent coupling of this aryl boronic acid with commercially available haloaromatic derivatives in a similar Suzuki coupling strategy as described above to afford the derivatives of type (IX) and (X).

SCHEME 1

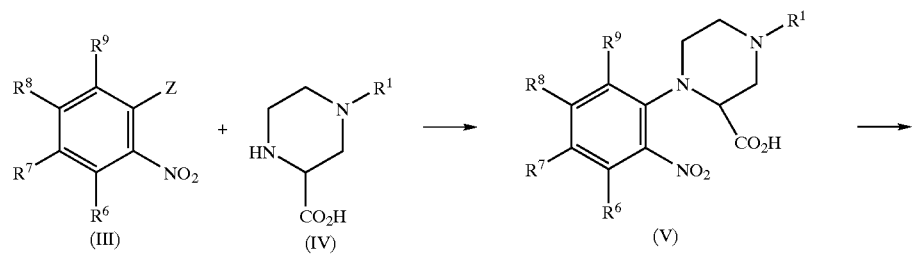

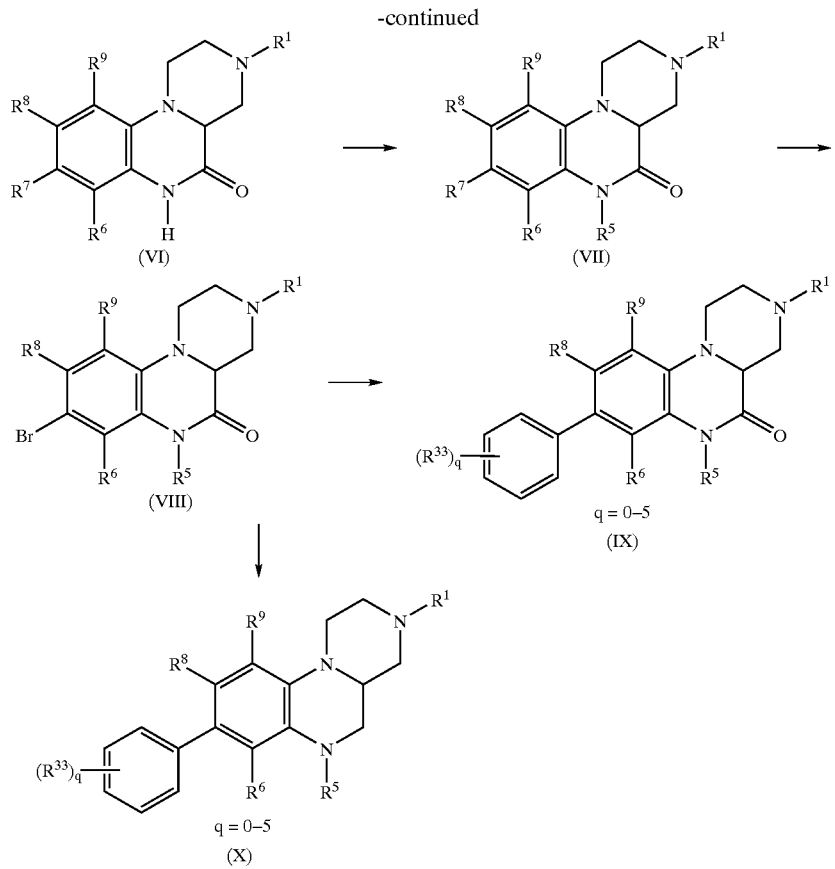

Formation of nitrogen linked biaryl derivatives is described in Scheme 2. Treatment of arylbromide derivatives of type (VIII) with diphenylmethylimine under $Pd_2(dba)_3$, BINAP catalyzed conditions followed by basic hydrolysis ($NH_2OH$—HCl, NaOAc, MeOH) of the imine affords the primary aniline derivative (XI). Coupling of these anilines with various arylbromides under Pd(0) catalyzed conditions affords the amine linked biaryl derivatives of type (XII) (see A. S. Guram, R. A. Rennels and S. L. Buchwald, *Angew. Chem. Int. Ed. Engl.*, 1995,34,1348). These lactam derivatives can also be alkylated and subsequently reduced to the amine, as previously described, then coupled to afford derivatives of type (XIII).

SCHEME 2

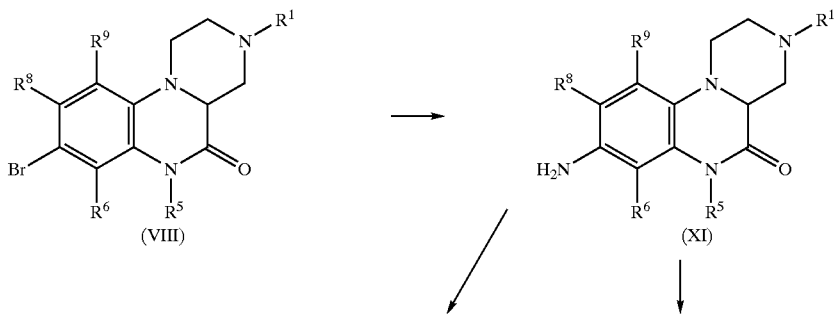

-continued

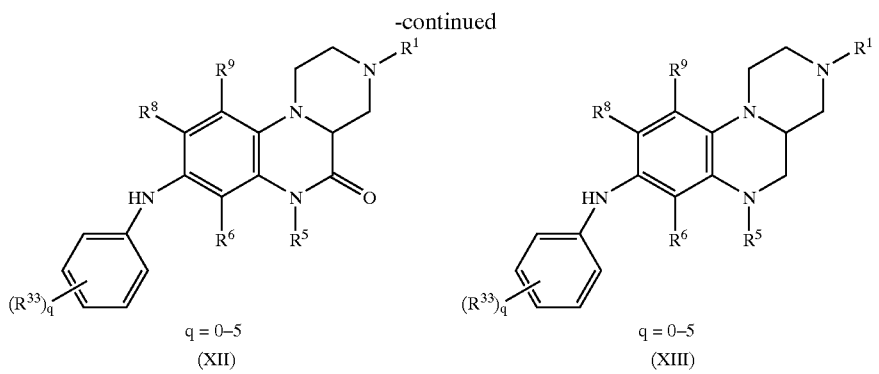

q = 0–5
(XII)

q = 0–5
(XIII)

Selective bromination of the alternate sites ($R^6$, $R^8$, and $R^9$) of derivatives of type (VII) (Scheme 1) is not possible under the current protocol. Initiating the synthesis in Scheme 1 of derivatives of type (VIII) with a halogen or nitro group at $R^6$, $R^8$, or $R^9$, allows for preparation of $R^6$, $R^8$, and $R^9$ biaryl or N-aryl derivatives. Use of an arylnitro group to effect this coupling either directly via the diazonium salt derivative or indirectly through transformatin of the diazonium salt to an aryl bromide via Sandoz reaction conditions (see Larock, R. C., *Comprehensive Organic Transformations*, VCH Publishers, New York, 1989) is an alternate route to these $R^6$, $R^8$, and $R^9$ substituted derivatives. Scheme 3 illustrates an example of this approach ($R^8$=Br) to aryl and N-aryl derivatives of type (XIV) via the protocol described above for Schemes 1 and 2.

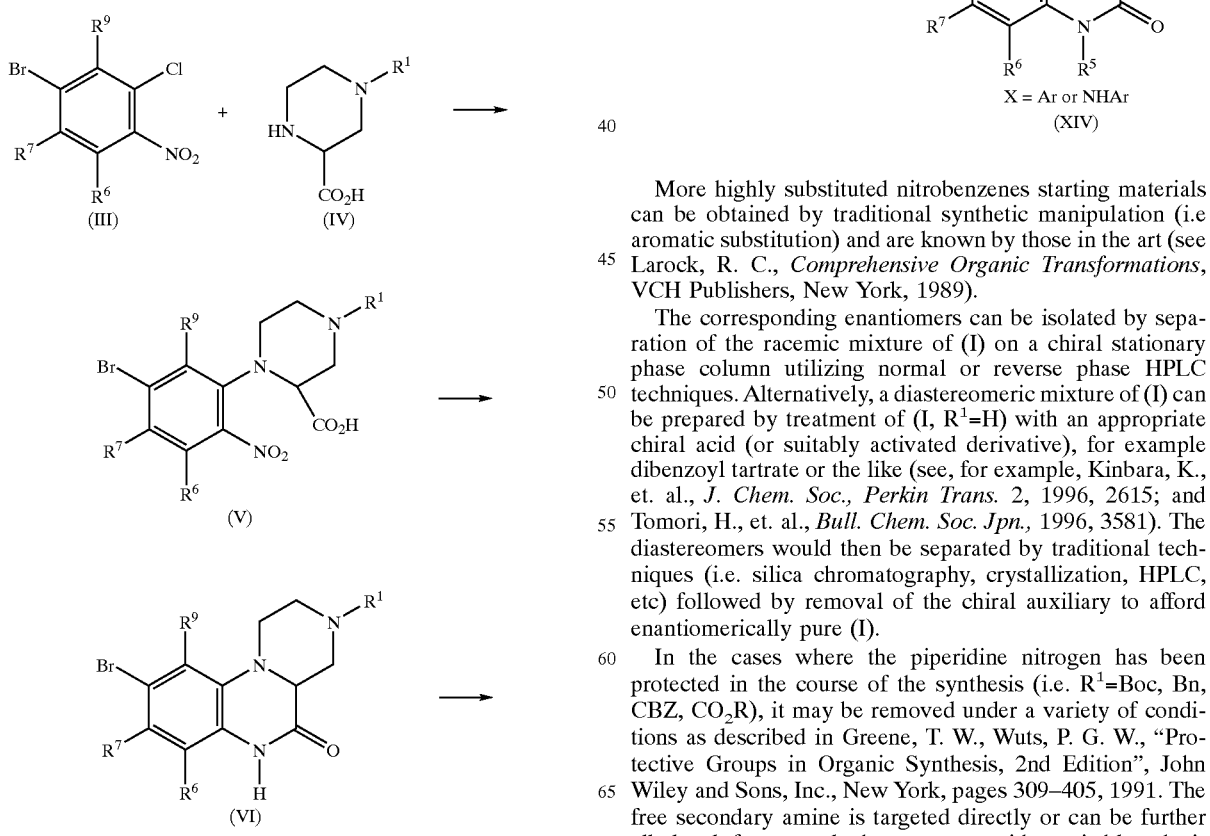

More highly substituted nitrobenzenes starting materials can be obtained by traditional synthetic manipulation (i.e aromatic substitution) and are known by those in the art (see Larock, R. C., *Comprehensive Organic Transformations*, VCH Publishers, New York, 1989).

The corresponding enantiomers can be isolated by separation of the racemic mixture of (I) on a chiral stationary phase column utilizing normal or reverse phase HPLC techniques. Alternatively, a diastereomeric mixture of (I) can be prepared by treatment of (I, $R^1$=H) with an appropriate chiral acid (or suitably activated derivative), for example dibenzoyl tartrate or the like (see, for example, Kinbara, K., et. al., *J. Chem. Soc., Perkin Trans.* 2, 1996, 2615; and Tomori, H., et. al., *Bull. Chem. Soc. Jpn.*, 1996, 3581). The diastereomers would then be separated by traditional techniques (i.e. silica chromatography, crystallization, HPLC, etc) followed by removal of the chiral auxiliary to afford enantiomerically pure (I).

In the cases where the piperidine nitrogen has been protected in the course of the synthesis (i.e. $R^1$=Boc, Bn, CBZ, $CO_2R$), it may be removed under a variety of conditions as described in Greene, T. W., Wuts, P. G. W., "Protective Groups in Organic Synthesis, 2nd Edition", John Wiley and Sons, Inc., New York, pages 309–405, 1991. The free secondary amine is targeted directly or can be further alkylated, for example, by treatment with a suitably substituted alkyl halide (R¹Cl, or R¹I) and a base, such as NaH or KH, to afford additional compounds of type (I), as described, for example, by Glennon, R. A., et. al., *Med. Chem. Res.*, 1996, 197.

An additional preparation of biaryl and/or NH-aryl linked compounds of type (IX), (X), etc. can be accomplished by preparation of the starting chloronitrophenyl compound with the required aryl substitution in place. For instance, initiating the synthesis with a derivative of type (III) where $R^6$, $R^7$, $R^8$, or $R^9$ is an aryl or NH-aryl substituent. Some of the methods for preparation of these starting materials has been described here and are known by those skilled in the art.

The preparation of the more highly substituted compounds of type (I-a) is shown in Scheme 4. A more detailed description of the variety of ring systems utilized and the methods to prepare them are detailed in DM 7014. These methods are amenable to the preparation of derivatives of type (I-a) described herein. Towards that end, alkylation of a dichloronitrophenyl derivative of type (XV) with a nucleophilic alkyl halide (X=OH, SH, NHR) (as described by Kharasch, N., Langford, R. B., *J. Org. Chem.*, 1963, 1903) and a suitable base affords the nitroaryl derivative (XVI). Elaboration of these functionalized derivatives is carried out as before (see Scheme 1). Addition of the piperidine carboxylic acid to afford derivatives of type (XVII) followed by reduction of the nitro functionality to give the cyclized derivatives (XVIII). The cyclization of the final ring can be accomplished on either the lactam (XVIII) to afford the tetracycle of type (XIX) or prior reduction of the amide moiety of (XVIII) followed by base catalyzed cyclization to afford the tetracyclic amine derivatives (XX). Likewise, reduction of the lactam moiety of (XIX) with a suitable reducing agent, such as DIBAL or $BH_3$, yields the amine derivatives (XX). Subsequent incorporation of the aryl and NH-aryl functionalities on the aromatic ring is performed as described previously. In addition, these more highly functionalized, novel tetracyclic ring systems can be derivatized on the aryl ring by a number of similar methods. There exists a wide range of procedures and protocols for functionalizing haloaromatics, aryldiazonium and aryltriflate compounds. These procedures are well known by those in the art and described, for example, by Stanforth, S. P., *Tetrahedron*, 1998, 263; Buchwald, S. L., et. al., *J. Am. Chem. Soc.*, 1998, 9722; Stille, J. K., et. al., *J. Am. Chem. Soc.*, 1984, 7500. Among these procedures are biaryl couplings, alkylations, acylations, aminations, and amidations. The power of palladium catalyzed functionalization of aromatic cores has been explored in depth in the last decade. An excellent review of this field can be found in J. Tsuji, "Palladium Reagents and Catalysts, Innovations in Organic Synthesis", J. Wiley and Sons, New York, 1995.

SCHEME 4

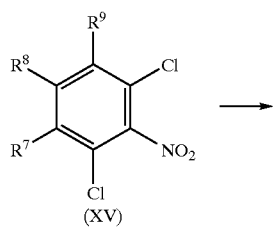

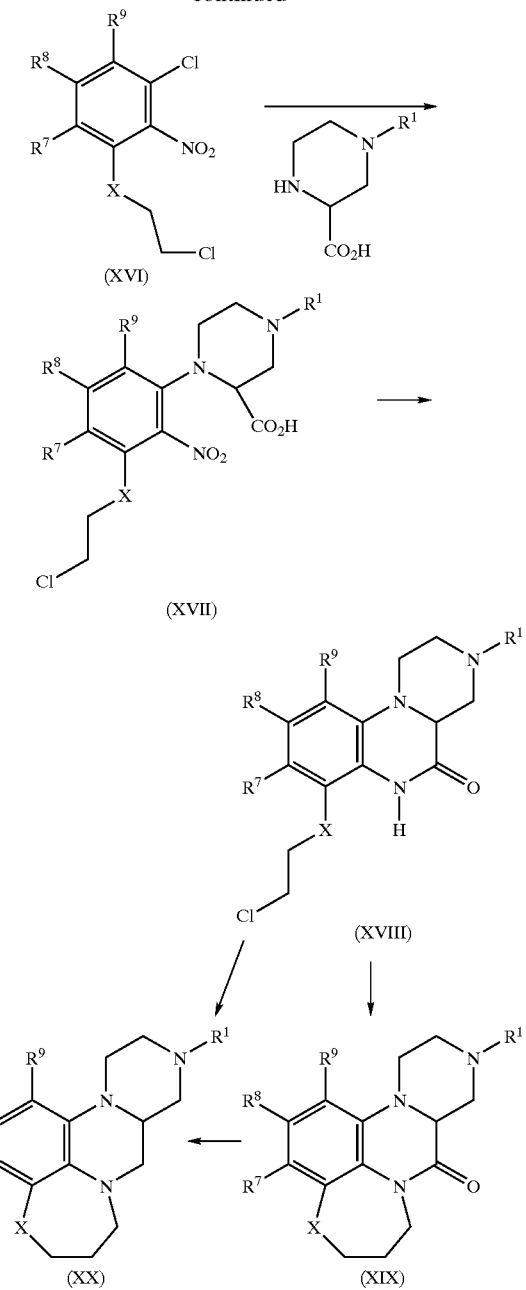

An alternate approach to the substituted fused anilines (I-a) is shown in Scheme 5. Using derivatives of type (VI) with $R^6$=H, the lactam can be reduced to the corresponding amine with DIBAL or the like. Subsequent base treatment, with for example NaH, and alkylation of the amine with, for example, a haloalkyl carboxylic acid (or equivalent activated haloalkylcarboxylic acid, (i.e. acid halide, mixed anhydride, acrylic acid, acryloyl chloride, etc.)), affords the derivative (XXI) which when treated under Friedel-Crafts acylation conditions (see Ed. G. A. Olah, "Friedel-Crafts and Related Reactions", J. Wiley and Sons, New York, 1964, Vol 3, Pts 1 and 2 or Chem. Rev., 1955, 229, or Olah, G. A., "Friedel-Crafts Chemistry", Wiley Interscience, New York, 1973, for varying conditions and protocols), i.e. strong Lewis acids ($AlCl_3$, $FeCl_3$, etc.), affords the cyclic alkylphenones (XXII). Elaboration of this derivative by reduction of the ketone with a suitable reducing agent or Wittig olefination of the ketone by standard conditions should allow for extensive diversity in preparing compounds of type (XXIII). These and other conditions for these transformations are known by those skilled in the art and examples of these may be found in Larock, R. C., *Comprehensive Organic Transformations*, VCH Publishers, New York, 1989.

Incorporation of nitrogen functionality into derivatives of type (XXII) can be accomplished in several ways. For example, Schmidt rearrangement (as described by Smith, P. A. S., *J. Am. Chem. Soc.*, 1948, 320) is effected by treatment of the carbonyl derivative (XXII) with NaN$_3$ and methanesulfonic acid to afford the bicyclic lactam (XXIV). Alternatively, this transformation may be carried out under Hoffmann rearrangement protocol (see, for example, Dike, S. Y., et. al., *Bioorg. Med. Chem. Lett.*, 1991, 383), by initial formation of the oxime derivative of (XXII) by treatment with hydroxylamine hydrochloride. Subsequent rearrangement to the lactam is efficiently accomplished by heating in polyphosphoric acid to afford the lactam (XXIV). Reduction of the lactam (XXIV) can be accomplished with a variety of reducing agents, for example, DIBAL, Red-Al and the like to afford the aniline (XXV). Alternatively, treatment of the lactam with dimethyltitanocene (Petasis, N., et.al.) followed by Pd/C catalyzed hydrogenation should afford the amine derivative (XXV) where $R^{11}$=Me. Standard conditions may be used for alkylation of the amine or lactam ($R^{10}$) to afford more highly substituted derivatives of type (XXIV) and (XXV).

SCHEME 5

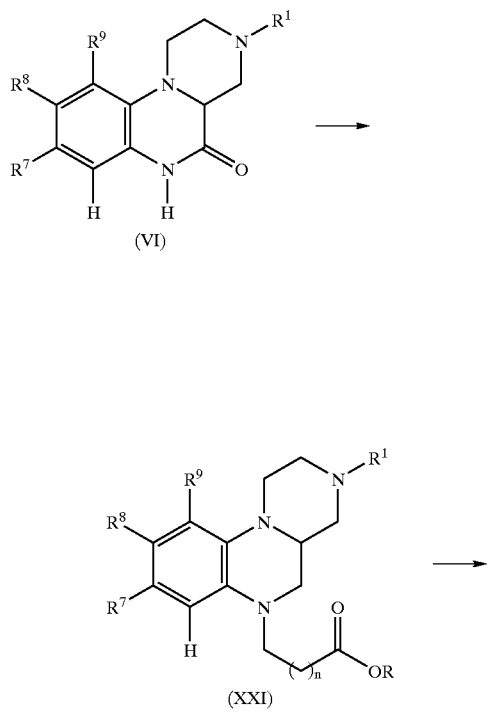

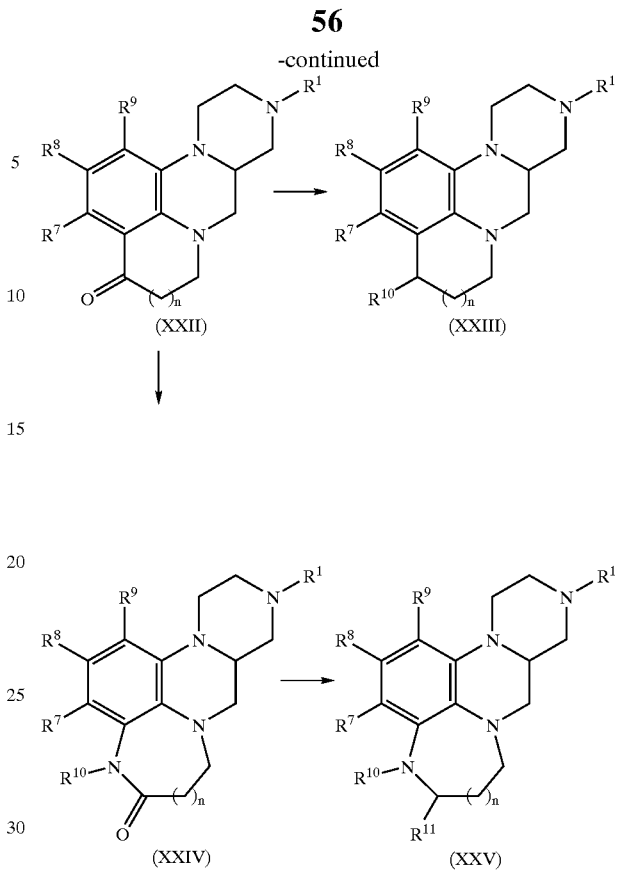

As was described previously, installation of an aryl or NH-aryl moiety on the aromatic ring of derivatives of type (XXII)-(XXV) can be accomplished in a variety of ways, dependant upon the substitution of the aromatic ring.

Furthermore and as an extension of this approach to a rapid preparation of a large array of biaryl, NH-aryl and aryl substituted derivatives, these various bromide derivatives (i.e.VII and VIII and related teracyclic brominated derivatives) can be bound to a solid support. Suzuki couplings can then be carried out on solid support as illustrated in Scheme 6. As an example of this approach, treatment of an aryl bromide of derivatives of type (XXVI, $R^1$=CBz) with H$_2$ and Pd/C, to remove the CBz protecting group, followed by extraction from aqueous base provides the free amine (XXVI, $R^1$=H). The free amine can be loaded onto a suitable solid support such as (XXVII) using conditions well known to those skilled in the art. Thus, p-nitrophenylchloroformate Wang resin (XXVII) which can be obtained commercially from sources such as Novabiochem, Inc. is swollen in a suitable solvent such as N-methyl pyrrolidinone and treated with 1.5 equiv. of amine to afford the functionalized resin (XXVIII). Suzuki couplings are then carried out in array format by treatment of resins (XXVIII) with a suitable palladium source such as Pd(PPh$_3$)$_4$ or Pd(dppf)Cl$_2$ and a suitable base such as 2M aqueous K$_2$CO$_3$ or Na$_2$CO$_3$ or triethylamine with an excess (typically 5 equivalents) of an aryl boronic acid (procedures for solid-phase Suzuki and other palladium couplings are well-known by those in the art, see for instance L. A. Thompson and J. A. Ellman, *Chem. Rev.* 1996, 96, (1), 555–600). The coupling may be repeated to ensure complete conversion to the desired coupled product. Cleavage from the solid support by treatment with TFA affords the corresponding functionalized derivatives (XXIX) as their TFA salts.

SCHEME 6

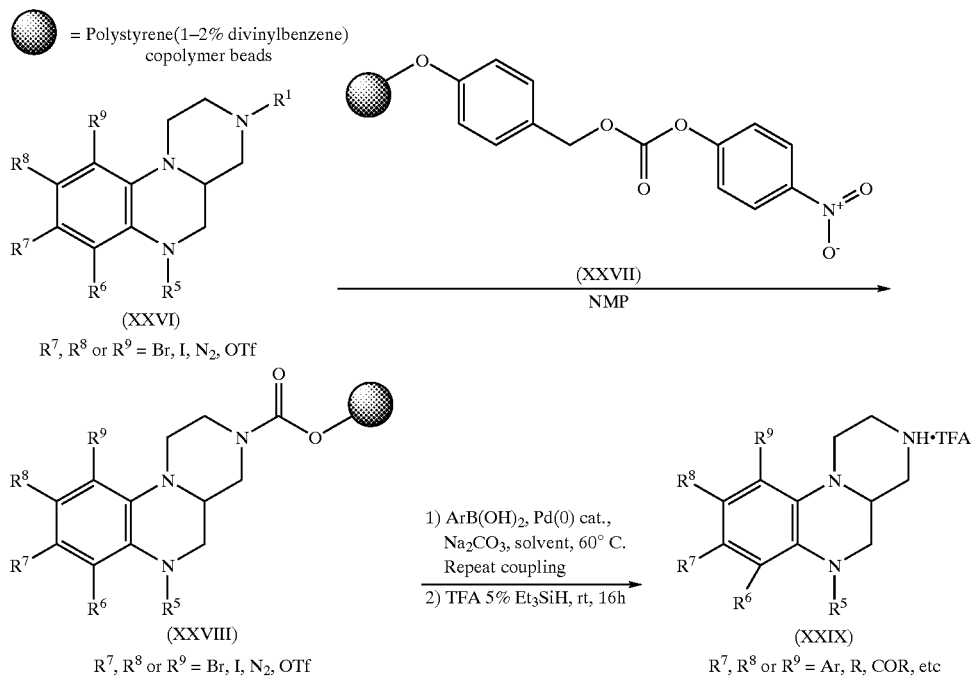

One such method to prepare compounds of Formula (I) and (I-a) with substituted $R^1$ sidechains in a more direct manner is illustrated in Scheme 7. Alkylation of the piperidine nitrogen (I or II, $R^1$=H) with a haloalkyl ester, such as $ClCH_2(CH_2)_pCO_2Me$, in the presence of NaI or KI and a base such as $K_2CO_3$, $Na_2CO_3$ or the like, in dioxane or THF or other such solvent while heating (see Glennon, R. A., et. al., *Med. Chem. Res.*, 1996, 197) affords the $R^1$ alkylated esters. Subsequent formation of the activated amides (XXX) is accomplished by treatment of the ester with N,O-dimethylhydroxylamine hydrochloride and a Lewis acid such as trimethylaluminum or triethylaluminum in toluene (see, for example, Golec, J. M. C., et. al., *Tetrahedron*, 1994, 809) at 0° C. Treatment of the amide (XXX) with a variety of organometallic agents, such as Grignard reagents $R^2MgBr$, alkyl and aryl lithium reagents etc. (see Sibi, M. P., et. al., *Tetrahedron Lett.*, 1992, 1941; and more generally House, H. O., *Modern Synthetic Reactions*, W. A. Benjamin, Inc., Menlo Park, Calif., 1972), in a suitable solvent such as THF, ether, etc. at low temperatures affords the substituted ketones (XXXI).

SCHEME 7

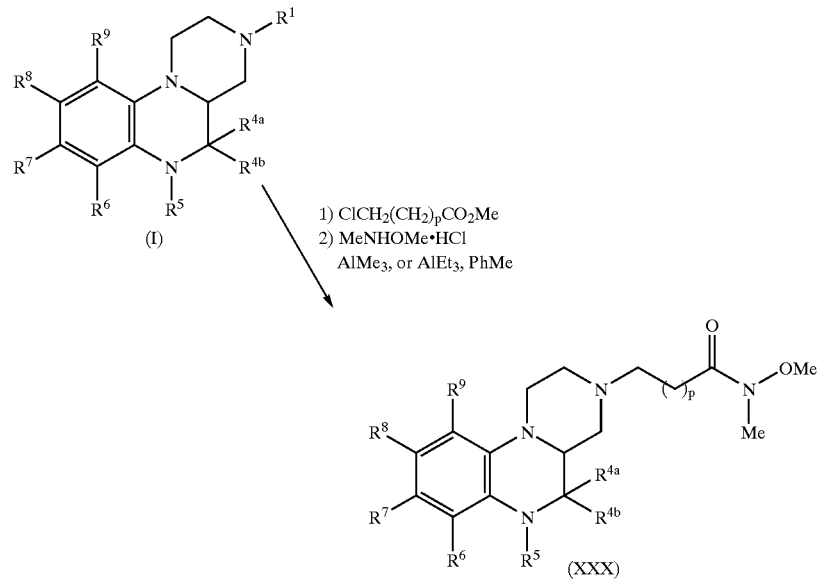

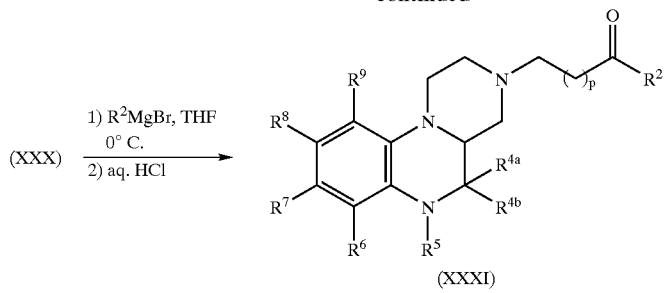

It is understood that for substituents R⁷, R⁸, R⁹, and R¹, the compounds of the present invention can be prepared in a number of ways well known to one skilled in the art of organic synthesis. The compounds of the present invention can be synthesized using the methods described herein, together with synthetic methods known in the art of synthetic organic chemistry, or variations thereon as appreciated by those skilled in the art. Additional methods include, but are not limited to, those described in U.S. Ser. No. 09/594,954 (filed Jun. 15, 2000); U.S. Ser. No. 09/595,250 (filed Jun. 15, 2000); and U.S. Ser. No. 09/594,008 (filed Jun. 15, 2000); wherein all three references are hereby incorporated in their entirety herein by reference.

It is also understood that for substituents in positions $R^1$, $R^{4a}$, $R^{4b}$, $R^5$, $R^6$, $R^7$, $R^8$, $R^9$, n, and X, the compounds of the present invention can be synthesized using additional methods described in DuPont Pharmaceuticals U.S. Provisional Patent Applications U.S. Ser. No. 60/256,745 (filed Dec. 20, 2000) and U.S. Ser. No. 60/256,740 (filed Dec. 20, 2000), hereby incorporated in their entirety herein by reference, together with synthetic methods known in the art of synthetic organic chemistry, or variations thereon as appreciated by those skilled in the art.

EXPERIMENTALS

Example 1

Preparation of 8-(4-Methoxy-2-methylphenyl)-2,3,4,4a-tetrahydro-1H-pyrazino[1,2-a]quinoxalin-5(6H)-one.

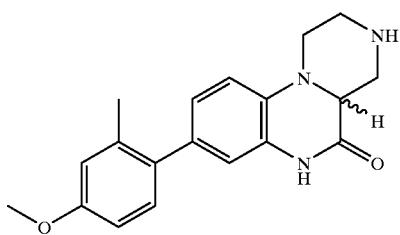

Step A. To a solution of piperazine-2-carboxylic acid dihydrochloride (10 g, 49 mmol) in 40 ml water was added an aqueous solution of sodium hydroxide (39 ml, 2.5 M). A solution of copper (II) sulfate pentahydrate (6.5 g, 26 mmol) in 80 ml water was added, and the deep blue solution was cooled to 5° C. Sodium bicarbonate (5 g, 59 mmol) was added in one portion, followed by the dropwise addition of benzylchloroformate (7.7 ml, 54 mmol) in 40 ml dioxane over 10 minutes. Sodium bicarbonate was added as needed to maintain a basic solution. The reaction was allowed to warm to rt and was stirred for 16 h. The precipitate was filtered and dried to afford 4-carbobenzyloxypiperazine-2-carboxylic acid, copper chelate used directly in the next step.

Step B. To a solution of 4-carbobenzyloxypiperazine-2-carboxylic acid, copper chelate in 750 ml water was added ethylenediaminetetracetic acid, disodium salt, dihydrate (7.9 g, 21 mmol). The mixture was heated to 80° C. for 3 h. The reaction mixture was then cooled to rt and concentrated to dryness. The residue was dissolved in 100 ml DMSO. 2-Fluoronitrobenzene (4.9 g, 35 mmol) and triethyl amine (20 ml, 143 mmol) were added and the solution was heated to 60° C. for 16 h. The dark reaction mixture was cooled to rt. Concentrated HCl was added to bring the pH to 3. The solution was then diluted with 500 ml water and the aqueous layer was extracted with ethyl acetate. The combined organics were washed with water, dried over MgSO₄ and concentrated to afford 4-carbobenzyloxy-1-(2-nitrophenyl)piperazine-2-carboxylic acid used directly in the next step.

Step C. To a solution of the above 4-carbobenzyloxy-1-(2-nitrophenyl)piperazine-2-carboxylic acid in 200 ml glacial acetic acid warmed to 60° C. was added iron powder (16 g) in portions. The reaction was heated at 60° C. for 3 h. The reaction was cooled to rt and 1N HCl was added. The resulting precipitate was filtered and dried. The crude material was dissolved in methylene chloride and passed through a plug of silica gel, eluting with 40% ethyl acetate/hexanes. The filtrate was concentrated to afford 3-carbobenzyloxy-2,3,4,4a-tetrahydro-1H-pyrazino[1,2-a]-quinoxalin-5(6H)-one as a white solid (7.98 g, 68% over 3 steps). ¹H NMR (CDCl₃, 300 MHz) δ7.32–7.38 (m, 5H), 7.00–7.06 (m, 1H), 6.86–6.91 (m, 1H), 6.78–6.80 (m, 2H), 5.18–5.19 (m, 2H), 4.75 (m, 1H), 4.31 (m, 1H), 3.59–3.63 (m, 1H), 3.50 (dd, J=11.1, 3.6 Hz, 1H), 3.06–3.14 (m, 2H), 2.72–2.81 (m, 1H), 1.65 (s, 1H) ppm. MS (ESI) m/z=338 [M+H].

Step D. To a solution of 3-carbobenzyloxy-2,3,4,4a-tetrahydro-1H-pyrazino[1,2-a]-quinoxaline-5(6H)-one (4.0 g, 11.9 mmol) in 30 ml DMF cooled to 0° C. was added a solution of N-bromosuccinimide in 30 ml DMF over 20 minutes. The orange reaction was stirred at 0° C. for an additional 1.5 h. Water was added and the aqueous layer was extracted with ethyl acetate. The combined organics were washed with water, dried over MgSO₄, and concentrated to a yellow solid. The crude material was recrystallized from hot ethyl acetate to give 8-bromo-3-carbobenzyloxy-2,3,4,4a-tetrahydro-1H-pyrazino[1, 2-a]-quinoxalin-5(6H)-one as a white solid (3.84 g, 78% recrystallized yield). ¹H NMR (CDCl₃, 300 MHz) δ7.32–7.38 (m, 5H), 7.12 (dd, J=8.8, 2.2 Hz, 1H), 6.92 (d, J=2.1, 1H), 6.62–6.65 (m, 1H), 5.18 (m, 2H), 4.74 (m, 1H), 4.31 (m, 1H), 3.47–3.57 (m, 2H), 3.06–3.13 (m, 2H), 2.73–2.96 (m, 1H), 1.61 (s, 1H) ppm. MS (ESI) m/z=416 [M+H]+.

Step E: Coupling procedure: To a solution of 8-bromo-3-carbobenzyloxy-2,3,4,4a-tetrahydro-1H-pyrazino [1,2-a]-quinoxalin-5(6H)-one (415 mg, 1 mmol) in benzene (10 ml) was added 2-methyl-4-methoxybenzene boronic acid (332 mg, 2 mmol), 2M Na₂CO₃ (2 ml), and dichlorobis (triphenylphosphine)palladium(II) (35 mg, 0.05 mmol). The reaction mixture was degassed and heated to reflux for 16 h. The reaction mixture was cooled to rt and concentrated to a black residue. The residue was taken up in ethyl acetate and filtered to afford 3-carbobenzyloxy-8-(4-methoxy-2-methylphenyl)-2,3,4,4a-tetrahydro-1H-pyrazino [1,2a] quinoxalin-5(6H) -one (297 mg, 65%).

Step F: Deprotection procedure: To a solution of 3-carbobenzyloxy-8-(4-methoxy-2-methylpheny)-2,3,4, 4a-tetrahydro-1H-pyrazino [1,2-a]quinoxalin-5(6H) -one (0.38 mmol) in 6 ml absolute ethanol was added 10% Pd/C (150 mg) and excess cyclohexene (3 ml). The black reaction mixture was heated to reflux. After 5 h, the mixture was cooled to rt and filtered through a pad of celite, washing heavily with methanol. The filtrate was concentrated to a colorless residue. The crude material was purified by radial PLC (1 mm plate, load and elute with methanol) to give the title compound as a colorless oil (30 mg, 24%). $^1$H NMR (CDCl$_3$, 300 MHz) δ7.12 (d, J=8.1 Hz, 1H), 6.95 (dd, J=8.5, 1.9 Hz, 1H), 6.76–6.82 (m, 3H), 6.67 (d, J=1.8 Hz, 1H), 3.83 (s, 3H), 3.53–3.67 (m, 3H), 3.18 (m, 1H), 2.79–3.01 (m, 3H), 2.26 (s, 3H) ppm. MS (ESI) m/z=324.2 [M+H]$^+$.

Example 2

Preparation of 8-(4-Methoxy-2-methylphenyl)-2,3,4,4a,5,6-hexahydro-1H-pyrazino [1,2-a]quinoxaline.

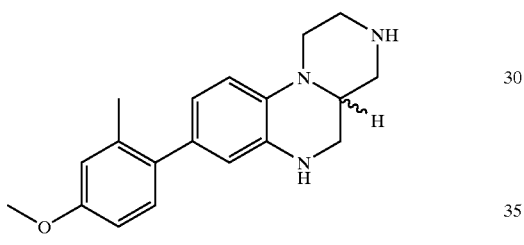

Step A: To a solution of 8-bromo-3-carbobenzyloxy-2,3, 4,4a-tetrahydro-1H-pyrazino [1, 2-a]-quinoxalin-5(6 H-)-one (2.15 g, 5.2 mmol) in 30 ml THF cooled to 0° C. was added a solution of BH$_3$-THF complex (16.25 ml, 16.25 mmol, 1M in THF). The reaction was allowed to slowly warm to rt over 25 minutes and was heated to ref lux. After 1.5 h, the reaction was cooled to rt. Methanol was added and the mixture was concentrated to a yellow residue. This was repeated. The crude material was purified by column chromatography using a Biotage© Flash 40i (4.0×15.0 cm column, load and elute with methylene chloride) to give 8-bromo-3-carbobenzyloxy-2,3,4,4a,5,6-hexahydro-1H-pryazino [1,2-a]quinoxaline as a white solid (1.26 g, 60%). $^1$H NMR (CDCl$_3$, 300 MHz) δ7.34–7.38 (m, 5H), 6.72–6.75 (dd, J=8.8, 2.2 Hz, 1H)), 6.53–6.59 (m, 2H), 5.16 (s, 2H), 4.19 (m, 2H), 3.77 (bs, 1H), 3.63 (m, 1H), 3.35 (m, 1H), 3.19–3.25 (m, 1H), 3.00–3.08 (m, 1H), 2.68–2.75 (m, 2H), 1.58 (s, 1H) ppm. MS (ESI) m/z=402 [M+H]$^+$.

Step B: General Coupling procedure: To a solution of 8-bromo-3-carbobenzyloxy-2,3,4,4a5,6-hexahydro-1H-pryazino [1,2-a]quinoxaline (0.5 mmol) in 5 ml benzene was added boronic acid (1.0 mmol), 2 M aqueous solution of Na$_2$CO$_3$ (1 ml), and dichlorobis (triphenylphosphine) palladium(II) (0.025 mmol). The reaction mixture was degassed thoroughly and heated to reflux for 16 h. The black reaction mixture was then cooled to rt and concentrated to a black residue. This was dissolved in methylene chloride and passed through a plug of silica gel, eluting with 40% ethyl acetate/hexanes. The filtrate was concentrated to a residue. The crude material was purified by radial PLC (1 mm plate, load and elute with 20% ethyl acetate/hexanes) to give the coupled product as a white foam.

Step C: General Deprotection procedure: To a solution of the CBz protected coupled product (0.21 mmol) in 4 ml absolute ethanol was added 10% Pd/C and excess cyclohexene (2 ml). The black reaction mixture was heated to reflux. After 4 h, the mixture was cooled to rt and filtered through a pad of celite, washing heavily with methanol. The filtrate was concentrated to a colorless residue. The crude material was purified by radial PLC (1 mm plate, load and elute with methanol) to give the secondary amine as a white foam.

The title compound was prepared from 8-bromo-3-carbobenzyloxy-2,3,4,5,6-hexahydro-1H-pyrazino [1,2-a] quinoxaline and the required boronic acid by the general procedure of steps B and C given above in 35% overall yield. $^1$H NMR (CDCl$_3$, 300 MHz) δ7.12–7.15 (m, 1H), 6.72–6.78 (m, 3H), 6.60 (dd, J=8.1, 2.1 Hz, 1H), 6.43 (d, J=2.1 Hz, 1H), 3.81 (s, 3H), 3.66–3.74 (m, 2H), 3.29–3.31 (m, 2H), 3.15–3.19 (m, 1H), 2.93–3.11 (m, 3H), 2.69–2.76 (m, 1H), 2.52–2.59 (m, 1H), 2.27 (s, 3H) ppm. MS (ESI) m/z=310 [M+H]$^+$.

Example 3

Preparation of 8-[4-Methoxy-2-(trifluoromethyl) phenyl]-2,3,4,4a, 5,6-hexahydro-1H-pyrazino [1,2-a]quinoxaline.

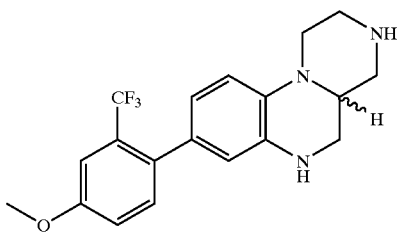

The title compound was prepared from 8-bromo-3-carbobenzyloxy-2,3,4,4a-5,6-hexahydro-1H-pyrazino [1,2-a]quinoxaline and the required boronic acid by the general procedure of Example 2, Steps B and C in 27% overall yield. $^1$H NMR (CDCl$_3$, 300 MHz) δ7.20–7.25 (m, 2H), 7.02 (dd, J=8.7, 2.7 Hz, 1H), 6.71 (d, J=8.4 Hz, 1H), 6.60 (dd, J=8.1, 1.5 Hz, 1H), 6.44 (d, J=1.5 Hz, 1H), 3.861 (s, 3H), 3.67–3.71 (m, 2H), 3.29–3.31 (m, 2H), 2.97–3.20 (m, 4H), 2.70–2.77 (m, 1H), 2.55 (m, 1H) ppm. MS (ESI) m/z=364 [M+H]$^+$.

Example 4

Preparation of 8-(2-Methylphenyl)-2,3,4,4a,5,6-hexahydro-1H-pyrazino [1,2-a]quinoxaline.

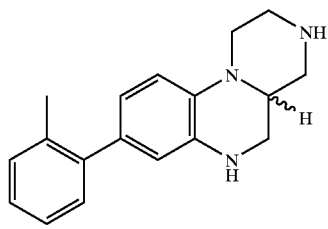

The title compound was prepared from 8-bromo-3-carbobenzyloxy-2,3,4,4a,5,6-hexahydro-1H-pyrazino [1,2-a]quinoxaline and the required boronic acid by the general procedure of Example 2, Steps B and C in 24% overall yield.

$^1$H NMR (CDCl$_3$, 300 MHz) δ7.19–7.26 (m, 4H), 6.55 (dd, J=8.2, 1.9 Hz, 1H), 6.46 (d, J=1.8 Hz, 1H), 3.69–3.73 (m, 1H), 2.94–3.32 (m, 6H), 2.76–2.80 (m, 1H), 2.58 (m, 1H), 2.29 (s, 3H) ppm. MS (ESI) m/z=280 [M+H]$^+$.

Example 5

Preparation of 8-(3-Methylphenyl)-2,3,4,4a,5,6-hexahydro-1H-pyrazino [1,2-a]quinoxaline.

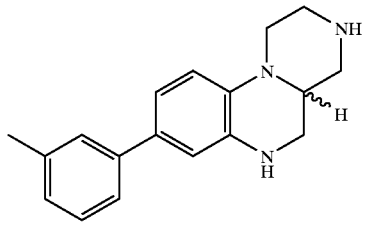

The title compound was prepared from 8-bromo-3-carbobenzyloxy-2,3,4,4a,5,6-hexahydro-1H-pyrazino [1,2-a]quinoxaline and the required boronic acid by the general procedure of Example 2, Steps B and C in 12% overall yield. $^1$H NMR (CDCl$_3$, 300 MHz) δ7.28–7.33 (m, 3H), 7.06–7.08 (m, 1H), 6.91 (dd, J=8.4, 1.8, 1 H), 6.73–6.78 (m, 2H), 3.68–3.72 (m, 1H), 3.27–3.48 (m, 2H), 3.15–3.19 (m, 1H), 2.93–3.07 (m, 3H), 2.70–2.77 (m, 1H), 2.53–2.61 (m, 1H), 2.38 (s, 3H) ppm. MS (ESI) m/z=280 [M+H]$^+$.

Example 6

Preparation of 8-(4-Methylphenyl)-2,3,4,4a,5,6-hexahydro-1H-pyrazino[1,2-a]quinoxaline.

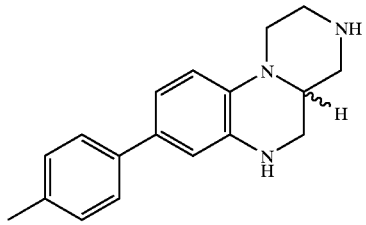

The title compound was prepared from 8-bromo-3-carbobenzyloxy-2,3,4,4a,5,6-hexahydro-1H-pyrazino [1,2-a]quinoxaline and the required boronic acid by the general procedure of Example 2, Steps B and C in 10% overall yield. $^1$H NMR (CDCl$_3$, 300 MHz) δ7.41 (d, J=8.4, 1H), 7.18 (d, J=8.1, 1H), 6.91 (dd, J=8.1, 2.1 Hz, 1H), 6.77 (d, J=8.4 Hz, 1H), 6.72 (d, J=2.1, 1H), 3.78 (m, 1H), 3.67–3.71 (m, 1H), 3.29–3.32 (m, 2H), 3.15–3.19 (m, 1H), 2.92–3.10 (m, 3H, 2.67–2.76 (m, 1H), 2.52–2.62 (m, 1H), 2.36 (s, 3H) ppm. MS (ESI) m/z=280 [M+H]$^+$.

Example 7

Preparation of 8-[4-Fluoro-2-(trifluoromethyl) phenyl]-2,3,4,4a,5,6-hexahydro-1H-pyrazino [1,2-a] quinoxaline.

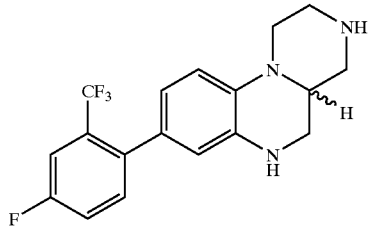

The title compound was prepared from 8-bromo-3-carbobenzyloxy-2,3,4,4a,5,6-hexahydro-1H-pyrazino [1,2-a]quinoxaline and the required boronic acid by the general procedure of Example 2, Steps B and C in 5% overall yield. $^1$H NMR (CDCl$_3$, 300 MHz) δ7.69–7.72 (m, 1H), 7.64 (m, 1H), 7.18 (m, 1H), 6.85 (dd, J=8.5, 2.2, 1H), 6.77 (d, J=8.4, 2.1 Hz, 1H), 6.66 (d, J=2.1 Hz, 1H), 3.83 (m, 1H), 3.68–3.71 (m, 1H), 2.98–3.36 (m, 6H), 2.70–2.79 (m, 1H), 2.57–2.61 (m, 1H) ppm. MS (ESI) m/z=352 [M+H]$^+$.

Example 8

Preparation of 9-(4-Methylphenyl) -2,3,4,4a,5,6-hexahydro-1H-pyrazino [1,2-a]quinoxaline.

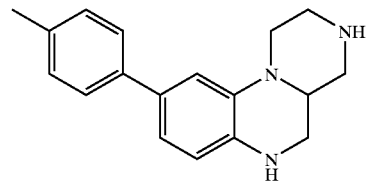

Step A. To a solution of piperazine-2-carboxylic acid dihydrochloride (10 g, 49 mmol) in 40 ml water was added an aqueous solution of sodium hydroxide (39 ml, 2.5 N). A solution of copper (II) sulfate (6.5 g, 26 mmol) in 80 ml water was added, and the deep blue solution was cooled to 5° C. Sodium bicarbonate (5 g, 59 mmol) was added in one portion, followed by the dropwise addition of benzylchloroformate (7.7 ml, 54 mmol) in 40 ml dioxane over 10 minutes. Sodium bicarbonate was added as needed to maintain a basic solution. The reaction was allowed to warm to rt and was stirred for 16 h. The precipitate was filtered and dried to afford 4-carbobenzyloxypiperazine-2-carboxylic acid, copper chelate residue used directly in the next step.

Step B. To a solution of 4-carbobenzyloxypiperazine-2-carboxylic acid, copper chelate in 750 ml water was added ethylenediaminetetracetic acid, disodium salt, dihydrate (7.9 g, 21 mmol) and the blue mixture was heated to 80° C. for 3 h. The reaction mixture was cooled to rt and concentrated to dryness. The blue residue was dissolved in 100 ml DMSO. 2,4-dichloronitrobenzene (6.66 g, 35 mmol) and triethyl amine (20 ml, 143 mmol) were added and the solution was heated to 60° C. for 16 h. The dark reaction mixture was cooled to rt. Concentrated HCl was added to pH=3. The solution was then diluted with 500 ml water and the aqueous layer was extracted with ethyl acetate. The combined organics were washed with water, dried over MgSO$_4$ and concentrated to afford 4-carbobenzyloxy-1-(4- chloro-2-nitrophenyl)piperazine-2-carboxylic acid as a yellow residue used directly in the next step.

Step C. To a solution of the above residue 4-carbobenzyloxy-1-(4-chloro-2-nitrophenyl)piperazine-2-carboxylic acid in 200 ml glacial acetic acid warmed to 60° C. was added iron powder (14 g) in portions. The reaction was heated at 60° C. for 3 h. The reaction was cooled to rt and 1N HCl was added. The resulting precipitate was filtered and dried. The crude material was dissolved in methylene chloride and passed through a plug of celite. The filtrate was concentrated to a dark red residue. This was purified by the Biotage 40i (4.0×15.0 cm column, load methylene chloride, elute 30–50% ethyl acetate/hexanes) to give 9-chloro-3-carbobenzyloxy-2,3,4,4a-tetrahydro-1H-pyrazino[1,2-a]-quinoxalin-5(6H)-one as an off-white solid (4.8 g, 37% yield over 3 steps). $^1$H NMR (CDCl$_3$, 300 MHz) δ7.32–7.37 (m, 5H), 6.82–6.85 (m, 1H), 6.68–6.75 (m, 2H), 5.18 (m, 2H), 4.73 (m, 1H), 4.31 (m, 1H), 3.49–3.54 (m, 2H), 3.07 (m, 2H), 2.74–2.81 (m, 1H) ppm. MS (ESI) m/z=372 [M+H]$^+$.

Step D. To a solution of 9-chloro-3-carbobenzyloxy-2,3,4,4a-tetrahydro-1H-pyrazino[1,2-a]-quinoxalin-5(6H)-one (1.45 g, 3.9 mmol) in 50 ml THF was added a solution of borane-THF complex (1M in THF, 12.2 ml, 12.2 mmol). After 15 min, the reaction was heated to reflux. After MS showed the absence of starting material, the reaction mixture was cooled to rt. Methanol was added and the solution concentrated to a yellow residue. This was repeated and the crude material was purified by column chromatography using a Biotage© Flash 40i (4.0×15.0 cm column, load with methylene chloride, elute with 25–30% ethyl acetate/hexanes) to give 9-Chloro-3-carbobenzyloxy-2,3,4,4a,5,6-hexahydro-1H-pyrazino[1,2-a]quinoxaline as an off-white solid (898.3 mg, 65%). $^1$H NMR (CDCl$_3$, 300 MHz) δ7.32–7.38 (m, 5H), 6.56–6.66 (m, 2H), 6.37–6.40 (m, 1H), 5.16 (s, 2H), 4.19 (m, 2H), 3.61–3.71 (m, 2H), 3.33–3.36 (m, 1H), 3.05–3.23 (m, 2H), 2.72–2.79 (m, 2H) ppm. MS (ESI) m/z=358 [M+H]$^+$.

Step E. To a two-necked round bottom flask charged with argon was added palladium (II) acetate (4 mg, 0.0195 mmol), 2-dicyclohexylphosphino-2'-(N,N-dimethylamino) biphenyl (10 mg, 0.02925 mmol), p-tolylboronic acid (80 mg, 0.59 mmol), potassium fluoride (68 mg, 1.17 mmol), and 9-Chloro-3-carbobenzyloxy-2,3,4,4a,5,6-hexahydro-1H-pyrazino[1,2-a]quinoxaline (140 mg, 0.39 mmol). 1 ml of degassed 1,4-dioxane was added and the reaction was degassed and heated to 100° C. for 20 h. The reaction mixture was cooled to rt and diluted with ether. 1N NaOH was added and the aqueous layer was extracted with ethyl acetate. The combined organics were washed with brine, dried over MgSO$_4$, and concentrated to a yellow residue. The crude material was purified by radial PLC (1 mm plate, load with methylene chloride, elute with 20–40% ethyl acetate/hexanes) to give 9-(4-methylphenyl)-2,3,4,4a,5,6-hexahydro-1H-pyrazino[1,2-a]quinoxaline as a yellow foam (0.23 mmol, 60%).

Step F. To a solution of the 9-(4-methylphenyl)-2,3,4,4a,5,6-hexahydro-1H-pyrazino[1,2-a]quinoxaline (96 mg, 0.23 mmol) in 4 ml absolute ethanol was added 10% Pd/C (95 mg) and excess cyclohexene (2 ml). The black reaction mixture was heated to reflux. After 6 h, the mixture was cooled to rt and filtered through a pad of celite, washing heavily with methanol. The filtrate was concentrated to a yellow oil. This was purified by reverse phase HPLC to give the title compound as the di-TFA salt(30 mg, 26%). $^1$H NMR (CD$_3$OD, 300 MHz) δ6.87–7.44 (m, 7H), 3.24–3.43 (br m, 6 H), 2.95 (br m, 1H), 2.34–2.44 (br m, 2 H), 1.99 (s, 3H) ppm. MS (ESI) m/z=280.3 [M+H]$^+$.

UTILITY

The compounds of the present invention have therapeutic utility for illnesses or disorders involving the neurotransmitter serotonin (5-hydroxy tryptamine or 5-HT) and either agonism or antagonism of 5-HT2 receptors, as demonstrated by the assays described below. Therapeutic utility for these illnesses or disorders could involve numerous biological processes affected by serotonin including, but not limited to, appetite, mood, sleep, sexual activity, and arterial constriction. These biological processes may also be important to numerous central nervous system (CNS) disorders including those related to the affective disorders of depression, anxiety, psychosis, and schizophrenia, as well as, disorders of food intake such as anorexia, bulemia, and obesity. The compounds of the present invention potentially have therapeutic utility in other conditions in which serotonin has been implicated, such as migraine, attention deficit disorder or attention deficit hyperactivity disorder, addictive behavior, and obsessive-compulsive disorder, as well as, conditions associated with cephalic pain, social phobias, and gastrointestinal disorders such as dysfunction of the gastrointestinal tract motility. Lastly, compounds of the present invention potentially have therapeutic utility in neurodegenerative diseases and traumatic conditions represented by the examples of Alzheimer's disease and brain/spinal cord trauma.

The pharmacological analysis of each compound for either antagonism or agonism of at 5-HT2A and 5-HT2C receptors consisted of in vitro and in vivo studies. In vitro analyses included K$_i$ determinations at 5-HT2A and 5-HT2C receptors and an assessment of functional (i.e., agonism or antagonism) activity at each receptor class by IP3 hydrolysis assays. Additional receptor assays were conducted to evaluate receptor specificity of 5-HT2A and 5-HT2C receptors over monoamine and nuisance receptors (e.g. histamine, dopamine, and muscarinic). A compound is considered active as a 5-HT2A antagonist or a 5-HT2C agonist if it has an IC$_{50}$ value or a K$_i$ value of less than about 50 micromolar; preferably less than about 0.1 micromolar; more preferably less than about 0.01 micromolar. Using the assays disclosed herein, compounds of the present invention have been shown to have an IC$_{50}$ value of less than about 50 micromolar for 5-HT2A antagonism or 5-HT2C agonism.

In vivo assays assessed compound activity in a variety of behavioral paradigms including quipazine head twitch, acute and chronic feeding models, anxiety and depression models (learned-helplessness, elevated plus maze, Geller-Siefter, conditioned taste aversion, taste reactivity, satiety sequence). In aggregate, these models reflect activity as a 5-HT2A antagonist (quipazine head twitch, depression models) or 5-HT2C agonist (feeding models, anxiety models, depression models) and provide some indication as to bioavailability, metabolism and pharmacokinetics.

Radioligand binding experiments were conducted on recombinant human 5-HT2A and 5-HT2C receptors expressed in HEK293E cells. The affinities of compounds of the present invention to bind at these receptors is determined by their capacity to compete for [$^{125}$I]-1-(2,5-dimethoxy-4-iodophenyl)-2-amino-propane (DOI) binding at the 5-HT2A or 5-HT2C. General references for binding assays include 1) Lucaites V L, Nelson D L, Wainscott D B, Baez M (1996) Receptor subtype and density determine the coupling repertoire of the 5-HT2 receptor subfamily. Life Sci., 59(13) :1081–95. J Med Chem 1988 Jan;31(1):5–7; 2) Glennon R A, Seggel M R, Soine W H, Herrick-Davis K, Lyon R A, Titeler M (1988) [125I]-1-(2,5-dimethoxy-4-iodophenyl)-2- amino-propane: an iodinated radioligand that specifically labels the agonist high-affinity state of 5-HT2 serotonin receptors. J Med. Chem. 31(1):5–7 and 3) Leonhardt S, Gorospe E, Hoffman B J, Teitler M (1992) Molecular pharmacological differences in the interaction of serotonin with 5-hydroxytryptamine1C and 5-hydroxytryptamine2 receptors. Mol Pharmacol., 42(2):328–35.

The functional properties of compounds (efficacy and potency) were determined in whole cells expressing 5-HT2A or 5-HT2C receptors by assessing their ability to stimulate or inhibit receptor-mediated phosphoinositol hydrolysis. The procedures used are described below.

In Vitro Binding Assays

Stable expression of 5-HT2A and 5-HT2C receptors in HEK293E cells.

Stable cell lines were generated by transfecting 293EBNA cells with plasmids containing human 5-HT2A, 5-HT2B, or 5-HT2C (VNV edited isoform) cDNA using calcium phosphate. These plasmids also contained the cytomegalovirus (CMV) immediate early promoter to drive receptor expression and EBV oriP for their maintenance as an extrachromosomal element, and the hph gene from *E. Coli* to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% $CO_2$) for 10 days. The 5-HT2A cells were adapted to spinner culture for bulk processing whereas it was necessary to maintain the other lines as adherent cultures. On the day of harvest, cells were washed in phosphate-buffered saline (PBS), counted, and stored at −80° C.

Membrane Preparation

On the day of assay, pellets of whole cells (containing approximately $1\times10^8$ cells) expressing the 5-HT2A or 5-HT2C receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., Ill.) using bovine serum albumin as the standard.

Radioligand binding assays for the 5-HT2A, and 5-HT2C receptors.

Radioligand binding studies were conducted to determine the binding affinities (KI values) of compounds for the human recombinant 5-HT2A, 5-HT2B, and 5-HT2C receptors (Fitzgerald et al., 1999). Assays were conducted in disposable polypropylene 96-well plates (Costar Corp., Cambridge, Mass.) and were initiated by the addition of 5-HT2A, 5-HT2B, or 5-HT2C membrane homogenate in tissue buffer (10–30 (g/well) to assay buffer (50 mM Tris HCl, 0.5 mM EDTA, 10 mM pargyline, 10 mM $MgSO_4$, 0.05% ascorbic acid, pH 7.5) containing [$^{125}$I]DOI for the 5-HT2A and 5-HT2C receptors (0.3–0.5 nM, final) or [$^3$H] LSD (2–2.5 nM, final) for the 5-HT2B receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (cell harvester; Inotech Biosystems Inc., Lansing, Mich.) over GFF glass-fiber filters that had been pre-soaked in 0.3% polyethyleneimine. Filters were washed in ice-cold 50 mM Tris HCl buffer (pH 7.5) and then counted in a gamma counter for the 5-HT2A and 5-HT2C assays, or by liquid scintillation spectroscopy for the 5-HT2B assay.

Phosphoinositide hydrolysis studies.

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT2A, 5-HT2B, or 5-HT2C receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 (g/ml hygromycin B, and 250(g/ml G418. Following a 24–48 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H]inositol for 16–18 hr. Following this incubation, the cells were washed with DMEM (without serum or inositol) containing 10 mM LiCl and 10 (M pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AGI-X8 resin), and counted by liquid scintillation spectroscopy as described previously (Egan et al., 1998).

Data analyses

The equilibrium apparent dissociation constants (Ki's) from the competition experiments were calculated using an iterative nonlinear regression curve-fitting program (GraphPad Prism; San Diego, Calif.). For the PI hydrolysis experiments, EC50's were calculated using a one-site 'pseudo' Hill model: $y=((R_{max}-R_{min})/(1+R/EC50)nH))+R_{max}$ where R=response (DeltaGraph, Monterey, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

In Vivo Experiments for Serotonergic Ligands.

Preclinical Efficacy, Potency, and Side Effect Liability.

a) Anti-Serotonin Efficacy.

Antagonism of Quipazine-Induced Head Twitch in Rat. Quipazine, an agonist at 5-HT receptors, produces a characteristic head twitch response in rats. 5-HT receptor antagonists effectively antagonize this 5-HT agonist-induced behavioral effect (Lucki et al., 1984). Accordingly, the quipazine-induced head twitch model in rat can function as an in vivo behavioral correlate to 5-HT receptor binding. Compounds are administered 30 minutes before behavioral testing (and 25 minutes before quipazine), and a dose-related antagonism of the quipazine response is determined.

b) Antipsychotic Efficacy.

Inhibition of the Conditioned Avoidance Response (CAR) in Rat. Rats are trained to consistently avoid (by climbing onto a pole suspended from the ceiling of the test chamber) an electric foot shock (0.75 mA) delivered to the grid floor of the testing chamber. All antipsychotic drugs effectively inhibit this conditioned avoidance response (Arnt, 1982). The ability of a compound to inhibit this response is used to determine the antipsychotic efficacy of potential drug candidates.

c) Extrapyramidal Side Effect Liability.

Induction of Catalepsy in Rat. Typical antipsychotic drugs produce extrapyramidal side effects (EPS) at clinically effective doses. The most widely accepted preclinical indicator of EPS liability in humans is a drug-induced catalepsy syndrome in rat (Costall and Naylor, 1975), a condition whereby the animal will remain immobile in an externally imposed posture (analogous to a catatonic stupor in humans). Rats are tested for induction of catalepsy in a dose-response test after oral administration of compounds.

d) CNS penetration; In vivo brain receptor occupancy.

In Vivo Binding. To determine the level of in vivo receptor occupancy, an in vivo receptor binding protocol is used. This procedure uses an appropriate radioligand to label the receptor of interest. For example, to measure both Dopamine D2 and 5-HT2A receptors in vivo, one can use $^3$H—N-methyl spiperone ($^3$H -NMSP), (Frost, et. al. 1987) The procedure uses rats (or mice) fasted overnight. To measure the effects of compounds on the receptors of interest, compounds are dosed, usually p.o. for example in 2 microliters/gram body weight in 0.25% Methocel suspension. The radiolabeled compound (in this example, $^3$H-NMSP) is administered by i.v. tail vein injection (10 microcuries label/200 gram rat). Time course experiments are used to determine the optimal time of binding for both the radiolabeled and unlabeled compound. These optimal time frames are used for all subsequent dose-response experiments. After the appropriate time frame of compound/radioligand exposure, the animals are sacrificed and the relevant brain regions dissected (frontal cortex for 5-HT2A and striatum for D2 receptors) and examined for their content of radioactivity. The level of non-specific binding is determined by examining a brain region known not to contain the receptor of interest (in this case the cerebellum) or by administering an excess of compound known pharmacologically to interact with the receptor.

REFERENCES

Arnt, J. Acta Pharmacol. et Toxicol. 1982: 51, 321–329.

Berridge M. J., Downes P. C. , Hanley M. R. (1982) Lithium amplifies agonist-dependent phosphotidyinositol response in brain and salivary glands. Biochem. J., 206, 587–595.

Costall, B and Naylor, R J. Psychopharmacology. 1975: 43, 69–74.

Egan C. T., Herrick-Davis K., Miller K., Glennon R. A., and Teitler M. (1998) Agonist activity of LSD and lisuride at cloned 5-HT2A and 5-HT2C receptors. Psychopharmacology, 136, 409–414.

Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin 5-HT2A and 5-HT2C receptors: evidence favoring the ternary complex and two-state models of agonist action. J. Neurochem., 72, 2127–2134.

Frost, J. J., Smith, A. C., Kuhar, M. J., Dannals, R. F., Wagner, H. N., 1987, In Vivo Binding of 3H-N-Methylspiperone to Dopamine and Serotonin Receptors. Life Sciences, 40:987–995.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9, 301–308.

Lucki, I, Nobler, M. S., Frazer, A., 1984, Differential actions of serotonin antagonists on two behavioral models of serotonin receptor activation in the rat. J. Pharmacol. Exp. Ther. 228(1):133–139.

Dosage and Formulation

The serotonin agonist and serotonin antagonist compounds of this invention can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.1 to about 30 mg/kg. Advantageously, compounds of the present invention may be administered in a single daily dose, or the total daily dosage may be administered in divided doses of two, three, or four times daily.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

What is claimed is:
1. A compound of formula (I):

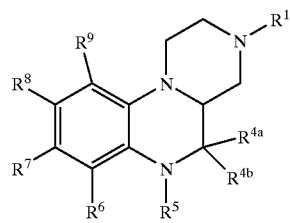

or a stereoisomer or a pharmaceutically acceptable salt form thereof, wherein:

$R^1$ is selected from
H,
$C(=O)R^2$,
$C(=O)OR^2$,
$C_{1-8}$ alkyl,
$C_{2-8}$ alkenyl,
$C_{2-8}$ alkynyl,
$C_{3-7}$ cycloalkyl,
$C_{1-6}$ alkyl substituted with Z,
$C_{2-6}$ alkenyl substituted with Z,
$C_{2-6}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{1-3}$ alkyl substituted with Y,
$C_{2-3}$ alkenyl substituted with Y,
$C_{2-3}$ alkynyl substituted with Y,
$C_{1-6}$ alkyl substituted with 0–2 $R^2$,
$C_{2-6}$ alkenyl substituted with 0–2 $R^2$,
$C_{2-6}$ alkynyl substituted with 0–2 $R^2$,
aryl substituted with 0–2 $R^2$, and
5–6 membered heterocyclic ring system containing at least one heteroatom selected from the group consisting of N, O, and S, said heterocyclic ring system substituted with 0–2 $R^2$;

Y is selected from
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_3$–6 cycloalkyl substituted with —($C_{1-3}$ alkyl)—Z,
aryl substituted with —($C_{1-3}$ alkyl)-Z, and
5–6 membered heterocyclic ring system containing at least one heteroatom selected from the group consisting of N, O, and S, said heterocyclic ring system substituted with —($C_{1-3}$ alkyl)-Z;

Z is selected from H,
—CH(OH)$R^2$,
—C(ethylenedioxy)$R^2$,
—O$R^2$,
—S$R^2$,
—N$R^2R^3$,
—C(O) $R^2$,
—C(O)N$R^2R^3$,
—N$R^3$C(O)$R^2$,
—C(O)O$R^2$,
—OC(O)$R^2$,
—CH(=N$R^4$)N$R^2R^3$, —NHC(=NR$^4$)NR$^2$R$^3$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
halo,
C$_{1-3}$ haloalkyl,
C$_{1-4}$ alkyl,
C$_{2-4}$ alkenyl,
C$_{2-4}$ alkynyl,
C$_{3-6}$ cycloalkyl,
aryl substituted with 0–5 R$^{42}$;
C$_{3-10}$ carbocyclic residue substituted with 0–3 R$^{41}$, and
5–10 membered heterocyclic ring system containing from 1–4 heteroatoms selected from the group consisting of N, O, and S substituted with 0–3 R$^{41}$;

R$^3$, at each occurrence, is independently selected from H, C$_{1-4}$ alkyl, C$_{2-4}$ alkenyl, C$_{2-4}$ alkynyl, and C$_{1-4}$ alkoxy;

alternatively, R$^2$ and R$^3$ join to form a 5- or 6-membered ring optionally substituted with —O— or —N(R$^4$)—;

R$^4$, at each occurrence, is independently selected from H and C$_{1-4}$ alkyl;

R$^{4a}$ is H or C$_{1-4}$ alkyl;

R$^{4b}$ is H;

alternatively, R$^{4a}$ and R$^{4b}$ are taken together to form =O or =S;

R$^5$ is H or C$_{1-4}$ alkyl;

R$^6$ is H or C$_{1-4}$ alkyl;

alternatively, R$^5$ and R$^6$ are taken together to form a fused heterocyclic ring of formula:

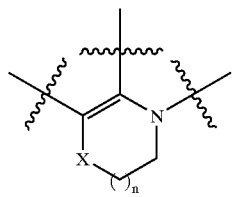

wherein:
X is a bond, —CH$_2$—, —O—, —S—, —S(=O)—, —S(=O)$_2$—, —NR$^{10}$—, —CH$_2$CH$_2$—, —OCH$_2$—, —SCH$_2$—, —CH$_2$O—, —CH$_2$S—, —CH$_2$NR$^{10}$—, —NR$^{10}$CH$_2$—, —NHC(=O)—, or —C(=O)NH—; and
n is 1 or 2;

R$^7$ and R$^9$, at each occurrence, are independently selected from
H, halo, —CF$_3$, —OCF$_3$, —OH, —CN, —NO$_2$, —NR$^{46}$R$^{47}$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{3-10}$ cycloalkyl substituted with 0–2 R$^{33}$,
C$_{1-4}$ alkyl substituted with 0–2 R$^{11}$,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^8$ is selected from
H, halo, —CF$_3$, —OCF$_3$, —OH, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{3-10}$ cycloalkyl substituted with 0–2 R$^{33}$,
C$_{1-4}$ alkyl substituted with 0–2 R$^{11}$,
C$_{2-4}$ alkenyl substituted with 0–2 R$^{11}$,
C$_{2-4}$ alkynyl substituted with 0–1 R$^{11}$,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{10}$ is selected from H,
C$_{1-4}$ alkyl substituted with 0–2 R$^{10A}$,
C$_{2-4}$ alkenyl substituted with 0–2 R$^{10A}$,
C$_{2-4}$ alkynyl substituted with 0–1 R$^{10A}$, and
C$_{1-4}$ alkoxy;

R$^{10A}$ is selected from
C$_{1-4}$ alkoxy,
C$_{3-6}$ carbocyclic residue substituted with 0–3 R$^{33}$,
phenyl substituted with 0–3 R$^{33}$, and
5–6 membered heterocyclic ring system containing 1, 2, or 3 heteroatoms selected from the group consisting of N, O, and S; substituted with 0–2 R$^{44}$;

R$^{11}$ is selected from
H, halo, —CF$_3$, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$,
NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$,
S(O)NR$^{12}$R$^{13}$, S(O)$_2$NR$^{12}$R$^{13}$, NR$^{14}$S(O)R$^{12}$, NR$^{14}$S(O)$_2$R$^{12}$,
NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{12}$, at each occurrence, is independently selected from
C$_{1-4}$ alkyl substituted with 0–1 R$^{12a}$,
C$_{2-4}$ alkenyl substituted with 0–1 R$^{12a}$,
C$_{2-4}$ alkynyl substituted with 0–1 R$^{12a}$,
C$_{3-6}$ cycloalkyl substituted with 0–3 R$^{33}$,
aryl substituted with 0–5 R$^{33}$;
C$_{3-10}$ carbocyclic residue substituted with 0–3 R$^{33}$, and
5–10 membered heterocyclic ring system containing from 1–4 heteroatoms selected from the group consisting of N, O, and S substituted with 0–3 R$^{31}$;

R$^{12a}$, at each occurrence, is independently selected from
phenyl substituted with 0–5 R$^{33}$;
C$_{3-10}$ carbocyclic residue substituted with 0–3 R$^{33}$, and
5–10 membered heterocyclic ring system containing from 1–4 heteroatoms selected from the group consisting of N, O, and S substituted with 0–3 R$^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$, $SO_2R^{45}$, $NR^{46}R^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{31}$, at each occurrence, is independently selected from H, OH, halo, $CF_3$, $SO_2R^{45}$, $NR^{46}R^{47}$, and $C_{1-4}$ alkyl;

$R^{33}$, at each occurrence, is independently selected from
H, OH, halo, CN, $NO_2$, $CF_3$, $SO_2R^{45}$, $NR^{46}R^{47}$, —C(=O)H,
phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl—C(=O)—, $C_{1-4}$ alkyl—C(=O)NH—, $C_{1-4}$ alkyl-OC(=O)—, $C_{1-4}$ alkyl—C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and
$C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{41}$, at each occurrence, is independently selected from
H, $CF_3$, halo, OH, $CO_2H$, $SO_2R^{45}$, $NR^{46}R^{47}$, $NO_2$, CN, =O;
$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$ and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl; and $R^{47}$, at each occurrence, is independently selected from H, $C_{1-4}$ alkyl, —C(=O)NH($C_{1-4}$ alkyl), —$SO_2$($C_{1-4}$ alkyl), —C(=O)O($C_{1-4}$ alkyl), —C(=O) ($C_{1-4}$ alkyl), and —C(=O)H;

provided when $R^5$ is H or $C_{1-4}$ alkyl; and $R^6$ is H or $C_{1-4}$ alkyl; then at least one of $R^7$, $R^8$ and $R^9$ must be either 1) an aryl group substituted with 1–5 $R^{33}$; 2) an arylmethyl-group substituted with 1–5 $R^{33}$; or 3) —$NR^{12}R^{13}$ wherein $R^{12}$ is an aryl group substituted with 1–5 $R^{33}$.

2. A compound of claim 1 of formula (I), wherein:

$R^1$ is selected from
H,
C(=O) $R^2$,
C(=O) $OR^2$,
$C_{1-8}$ alkyl,
$C_{2-8}$ alkenyl,
$C_{2-8}$ alkynyl,
$C_{3-7}$ cycloalkyl,
$C_{1-6}$ alkyl substituted with 0–2 $R^2$,
$C_{2-6}$ alkenyl substituted with 0–2 $R^2$,
$C_{2-6}$ alkynyl substituted with 0–2 $R^2$,
aryl substituted with 0–2 $R^2$, and
5–6 membered heterocyclic ring system containing at least one heteroatom selected from the group consisting of N, O, and S, said heterocyclic ring system substituted with 0–2 $R^2$;

$R^2$, at each occurrence, is independently selected from
F, Cl, $CH_2F$, $CHF_2$, $CF_3$,
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^{4a}$ is H or $C_{1-4}$ alkyl;

$R^{4b}$ is H;

alternatively, $R^{4a}$ and $R^{4b}$ are taken together to form =O or =S;

$R^5$ is H or $C_{1-4}$ alkyl;

$R^6$ is H or $C_{1-4}$ alkyl;

$R^7$ is selected from
H, F, Cl, —$CF_3$, —$OCF_3$, —OH, —CN, —$NO_2$, $NR^{12}R^{13}$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
methyl substituted with $R^{11}$;
$C_{3-6}$ carbocyclic residue substituted with 0–3 $R^{33}$; and
aryl substituted with 0–5 $R^{33}$;

$R^8$ is selected from
H, F, Cl —$CF_3$, —$OCF_3$, —OH, —CN, —$NO_2$, $NR^{12}R^{13}$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
methyl substituted with $R^{11}$;
$C_{3-6}$ carbocyclic residue substituted with 0–3 $R^{33}$; and
aryl substituted with 0–5 $R^{33}$;

$R^9$ is selected from
H, F, Cl, —$CF_3$, —$OCF_3$, —OH, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, and ($C_{1-4}$ haloalkyl)oxy;

$R^{11}$ is aryl substituted with 0–5 $R^{33}$, $R^{12}$ is aryl substituted with 0–5 $R^{33}$, $R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{16}$, at each occurrence, is independently selected from H, OH, halo, CN, $NO_2$, $CF_3$, $SO_2R^{45}$, $NR^{46}R^{47}$, —C(=O) H, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{33}$, at each occurrence, is independently selected from
H, OH, halo, CN, $NO_2$, $CF_3$, $SO_2R^{45}$, $NR^{46}R^{47}$, —C(=O)H,
phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl—C(=O)—, $C_{1-4}$ alkyl—C(=O)NH—, $C_{1-4}$ alkyl—OC(=O)—, $C_{1-4}$ alkyl—C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, butoxy, —$SO_2R^{45}$, —$NR^{46}R^{47}$, $NR^{46}R^{47}C$(=O)—, or ($C_{1-4}$ alkyl)$CO_2$—; and
$C_{2-6}$ alkenyl substituted with OH, methoxy, ethoxy, propoxy, butoxy, —$SO_2R^{45}$, —$NR^{46}R^{47}$, $NR^{46}R^{47}C$(=O)—, or ($C_{1-4}$ alkyl)$CO_2$—;

$R^{41}$, at each occurrence, is independently selected from
H, $CF_3$, halo, OH, $CO_2H$, $SO_2R^{45}$, $NR^{46}R^{47}$, $NO_2$, CN, =O;
$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, CH(=NH)$NH_2$, NHC(=NH) $NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R_{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl; and $R^{47}$, at each occurrence, is independently selected from H, $C_{1-4}$alkyl, —C(=O)NH($C_{1-4}$ alkyl), —$SO_2$($C_{1-4}$ alkyl), —C(=O)O($C_{1-4}$ alkyl), —C(=O)($C_{1-4}$ alkyl), and —C(=O)H;

provided at least one of $R^7$ or $R^8$ must be either 1) an aryl group substituted with 1–5 $R^{33}$; 2) an arylmethyl-group substituted with 1–5 $R^{33}$; or 3) —$NR^{12}R^{13}$ wherein $R^{12}$ is an aryl group substituted with 1–5 $R^{33}$.

3. A compound of claim 2 of formula (I), wherein:
$R^1$ is selected from H,
$C_{1-5}$ alkyl substituted with 0–1 $R^2$,
$C_{2-5}$ alkenyl substituted with 0–1 $R^2$, and
$C_{2-3}$ alkynyl substituted with 0–1 $R^2$;
$R^2$ is $C_{3-6}$ cycloalkyl;
$R^{4a}$ is H;
$R^{4b}$ is H;
$R^7$ is selected from
H, F, Cl, —$CH_3$, —$OCH_3$, —$CF_3$, —$OCF_3$, —CN, —$NO_2$, $NR^{12}R^{13}$, $R^{11}$;
methyl substituted with $R^{11}$; and
phenyl substituted with 0–2 $R^{33}$;
$R^8$ is selected from
H, F, Cl, —$CH_3$, —$OCH_3$, —$CF_3$, —$OCF_3$, —CN, —$NO_2$, $NR^{12}R^{13}$, $R^{11}$;
methyl substituted with $R^{11}$; and
phenyl substituted with 0–2 $R^{33}$;
$R^9$ is selected from H, F, Cl, —$CH_3$, —$OCH_3$, —$CF_3$, —$OCF_3$, —CN, and —$NO_2$;
$R^{11}$ is selected from
phenyl-substituted with 0–5 fluoro;
naphthyl-substituted with 0–3 $R^{33}$;
2-($H_3CCH_2C$(=O))-phenyl-substituted with $R^{33}$;
2-($H_3CC$(=O))-phenyl-substituted with $R^{33}$;
2-(HC(=O))-phenyl-substituted with $R^{33}$;
2-($H_3CCH$(OH))-phenyl-substituted with $R^{33}$;
2-($H_3CCH_2CH$(OH))-phenyl-substituted with $R^{33}$;
2-(HOCH$_2$)-phenyl-substituted with $R^{33}$;
2-(HOCH$_2$CH$_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH$(OMe))-phenyl-substituted with $R^{33}$;
2-($H_3COC$(=O))-phenyl-substituted with $R^{33}$;
2-(HOCH$_2$CH=CH)-phenyl-substituted with $R^{33}$;
2-((MeOC=O)CH=CH)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-($H_3CO$)-phenyl-substituted with $R^{33}$;
3-(fluoro)-phenyl-substituted with $R^{33}$;
3-(chloro)-phenyl-substituted with $R^{33}$;
4-(NC)-phenyl-substituted with $R^{33}$;
4-(fluoro)-phenyl-substituted with $R^{33}$;
4-(chloro)-phenyl-substituted with $R^{33}$;
4-($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C$(=O)) -phenyl-substituted with $R^{33}$;
4-(($H_3C)_2$CHC(=O)) -phenyl-substituted with $R^{33}$;
4-($H_3CCH_2C$(=O))-phenyl-substituted with $R^{33}$;
4-($H_3CC$(=O))-phenyl-substituted with $R^{33}$;
4-($H_3CCH_2CH_2CH$(OH))-phenyl-substituted with $R^{33}$;
4-(($H_3C)_2$CHCH(OH))-phenyl-substituted with $R^{33}$;
4-($H_3CCH_2CH$ (OH))-phenyl-substituted with $R^{33}$;
4-($H_3CCH$(OH))-phenyl-substituted with $R^{33}$;
4-(cyclopropyloxy)-phenyl-substituted with $R^{33}$;

4-(cyclobutyloxy)-phenyl-substituted with $R^{33}$; and
4-(cyclopentyloxy)-phenyl-substituted with $R^{33}$;

$R^{12}$ is selected from
phenyl-substituted with 0–5 fluoro;
naphthyl-substituted with 0–3 $R^{33}$;
2-($H_3CCH_2C(=O)$)-phenyl-substituted with $R^{33}$;
2-($H_3CC(=O)$)-phenyl-substituted with $R^{33}$;
2-($HC(=O)$)-phenyl-substituted with $R^{33}$;
2-($H_3CCH(OH)$)-phenyl-substituted with $R^{33}$;
2-($H_3CCH_2CH(OH)$)-phenyl-substituted with $R^{33}$;
2-($HOCH_2$)-phenyl-substituted with $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$) -phenyl-substituted with $R^{33}$;
2-($H_3CCH(OMe)$)-phenyl-substituted with $R^{33}$;
2-($H_3COC(=O)$)-phenyl-substituted with $R^{33}$;
2-($HOCH_2CH=CH$)-phenyl-substituted with $R^{33}$;
2-(($MeOC=O)CH=CH$)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-($H_3CO$)-phenyl-substituted with $R^{33}$;
3-(fluoro)-phenyl-substituted with $R^{33}$;
3-(chloro)-phenyl-substituted with $R^{33}$;
4-(NC)-phenyl-substituted with $R^{33}$;
4-(fluoro)-phenyl-substituted with $R^{33}$;
4-(chloro)-phenyl-substituted with $R^{33}$;
4-($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C(=O)$)-phenyl-substituted with $R^{33}$;
4-(($H_3C)_2CHC(=O)$) -phenyl-substituted with $R^{33}$;
4-($H_3CCH_2C(=O)$) -phenyl-substituted with $R^{33}$;
4-($H_3CC(=O)$)-phenyl-substituted with $R^{33}$;
4-($H_3CCH_2CH_2CH(OH)$)-phenyl-substituted with $R^{33}$;
4-(($H_3C)_2CHCH(OH)$) -phenyl-substituted with $R^{33}$;
4-($H_3CCH_2CH(OH)$)-phenyl-substituted with $R^{33}$;
4-($H_3CCH(OH)$)-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy; and $R^{33}$, at each occurrence, is independently selected from H, F, Cl, —$CH_3$, —$OCH_3$, —$CF_3$, —$OCF_3$, —CN, and —$NO_2$;

provided at least one of $R^7$ or $R^8$ must be either 1) an aryl group substituted with 1–5 $R^{33}$; 2) an arylmethyl-group substituted with 1–5 $R^{33}$; or 3) —$NR^{12}R^{13}$ wherein $R^{12}$ is an aryl group substituted with 1–5 $R^{33}$.

4. A compound of claim 2 of Formula (I) wherein:

$R^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, —$CH=CH_2$, —$CH_2$—$CH=CH_2$, —$CH=CH$—$CH_3$, —$C\equiv$—CH, —$C\equiv C$—$CH_3$, and —$CH_2$—$C\equiv$—CH;

$R^{4a}$ is H;

$R^{4b}$ is H;

alternatively, $R^{4a}$ and $R^{4b}$ are taken together to form =O;

$R^7$ is selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;

$R^8$ is selected from
2-chlorophenyl, 2-fluorophenyl, 2-bromophenyl, 2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl,
3-cyanophenyl, 3-methylphenyl, 3-ethylphenyl,
3-propylphenyl, 3-isopropylphenyl, 3-butylphenyl,
3-trifluoromethylphenyl, 3-methoxyphenyl,
3-isopropoxyphenyl, 3-trifluoromethoxyphenyl,
3-thiomethoxyphenyl,
4-chlorophenyl, 4-fluorophenyl, 4-bromophenyl,
4-cyanophenyl, 4-methylphenyl, 4-ethylphenyl,
4-propylphenyl, 4-isopropylphenyl, 4-butylphenyl,
4-trifluoromethylphenyl, 4-methoxyphenyl,
4-isopropoxyphenyl, 4-trifluoromethoxyphenyl,
4-thiomethoxyphenyl,
2,3-dichlorophenyl, 2,3-difluorophenyl,
2,3-dimethylphenyl, 2,3-ditrifluoromethylphenyl,
2,3-dimethoxyphenyl, 2,3-ditrifluoromethoxyphenyl,
2,4-dichlorophenyl, 2,4-difluorophenyl,
2,4-dimethylphenyl, 2,4-ditrifluoromethylphenyl,
2,4-dimethoxyphenyl, 2,4-ditrifluoromethoxyphenyl,
2,5-dichlorophenyl, 2,5-difluorophenyl,
2,5-dimethylphenyl, 2,5-ditrifluoromethylphenyl,
2,5-dimethoxyphenyl, 2,5-ditrifluoromethoxyphenyl,
2,6-dichlorophenyl, 2,6-difluorophenyl,
2,6-dimethylphenyl, 2,6-ditrifluoromethylphenyl,
2,6-dimethoxyphenyl, 2,6-ditrifluoromethoxyphenyl,
3,4-dichlorophenyl, 3,4-difluorophenyl,
3,4-dimethylphenyl, 3,4-ditrifluoromethylphenyl,
3,4-dimethoxyphenyl, 3,4-ditrifluoromethoxyphenyl,
2,4,6-trichlorophenyl, 2,4,6-trifluorophenyl,
2,4,6-trimethylphenyl, 2,4,6-tritrfluoromethylphenyl,
2,4,6-trimethoxyphenyl, 2,4,6-tritrifluoromethoxyphenyl, 2-chloro-4-CF₃-phenyl, 2-fluoro-3-chloro-phenyl,
2-chloro-4-CF₃-phenyl, 2-chloro-4-methoxy-phenyl,
2-methoxy-4-isopropyl-phenyl, 2-CF₃-4-methoxy-phenyl,
2-methyl-4-methoxy-5-fluoro-phenyl,
2-methyl-4-methoxy-phenyl, 2-chloro-4-CF₃O-phenyl,
2,4,5-trimethyl-phenyl, 2-methyl-4-chloro-phenyl,
4-acetylphenyl, 3-acetamidophenyl, 2-naphthyl;
2-Me-5-F-phenyl, 2-F-5-Me-phenyl, 2-MeO-5-F-phenyl,
2-Me-3-Cl-phenyl, 3-NO₂-phenyl, 2-NO₂-phenyl,
2-Cl-3-Me-phenyl, 2-Me-4-EtO-phenyl, 2-Me-4-F-phenyl,
2-Cl-6-F-phenyl, 2-Cl-4-(CHF₂)O-phenyl,
2,4-diMeO-6-F-phenyl, 2-CF₃-6-F-phenyl,
2-MeS-phenyl, 2,6-diCl-4-MeO-phenyl,
2,3,4-triF-phenyl, 2,6-diF-4-Cl-phenyl,
2,3,4-tetraF-phenyl, 2,3,4,5,6-pentaF-phenyl,
2-CF₃-4-EtO-phenyl, 2-CF₃-4-iPrO-phenyl,
2-CF₃-4-Cl-phenyl, 2-CF₃-4-F-phenyl, 2-Cl-4-EtO-phenyl,
2-Cl-4-iPrO-phenyl, 2-Et-4-MeO-phenyl,
2-CHO-4-MeO-phenyl, 2-CH₃CH(OH)-4-MeO-phenyl,
2-CH₃CH(OH)-4-F-phenyl, 2-CH₃CH(OH)-4-Cl-phenyl,
2-CH₃CH(OH)-4-Me-phenyl, 2-CH₃CH(OMe)-4-MeO-phenyl,
2-CH₃C(=O)-4-MeO-phenyl, 2-CH₃C(=O)-4-F-phenyl,
2-CH₃C(=O)-4-Cl-phenyl, 2-CH₃C(=O)-4-Me-phenyl,
2-H₂C(OH)-4-MeO-phenyl, 2-H₂C(OMe)-4-MeO-phenyl,
2-H₃CCH₂CH(OH)-4-MeO-phenyl, 2-H₃CCH₂C(=O)-4-MeO-phenyl,
2-CH₃CO₂CH₂CH₂-4-MeO-phenyl,
(Z)-2-HOCH₂CH=CH-4-MeO-phenyl,
(E)-2-HOCH₂CH=CH-4-MeO-phenyl,
(Z)-2-CH₃CO₂CH=CH-4-MeO-phenyl,
(E)-2-CH₃CO₂CH=CH-4-MeO-phenyl,
2-CH₃OCH₂CH₂-4-MeO-phenyl,
2-F-4-MeO-phenyl, 2-Cl-4-F-phenyl,
cyclohexyl, cyclopentyl, cyclohexylmethyl,
benzyl, 2-F-benzyl, 3-F-benzyl, 4-F-benzyl,
3-MeO-benzyl, 3-OH-benzyl, 2-MeO-benzyl,
2-OH-benzyl, 2-MeOC(=O)-3-MeO-phenyl,
2-Me-4-CN-phenyl, 2-Me-3-CN-phenyl,
2-Me-4-MeS-phenyl, 2-CF₃-4-CN-phenyl,
2-CHO-phenyl, 3-CHO-phenyl, 2-HOCH₂-phenyl,
3-HOCH₂-phenyl, 3-Me OCH₂-phenyl,
3-Me₂NCH₂-phenyl, 3-CN-4-F-phenyl,
2-Me-4-H₂NCO-phenyl, 2-Me-4-MeOC(=O)-phenyl,
3-H₂NCO-4-F-phenyl, 2-Me₂NCH₂-4-MeO-phenyl-,
2-Me-4-CH₃C(=O)-phenyl,
phenyl—NH—, (1-naphthyl)-NH—,
(2-naphthyl)-NH—, (2-[1,1'-biphenyl])-NH—,
(3-[1,1'-biphenyl])-NH—, (4-[1,1'-biphenyl])-NH—,
(2-F-phenyl)-NH—, (2-Cl-phenyl)-NH—,
(2-CF₃-phenyl)-NH—, (2-CH₃-phenyl)-NH—,
(2-OMe-phenyl)-NH—, (2-CN-phenyl)-NH—,
(2-OCF₃-phenyl)-NH—, (2-SMe-phenyl)-NH—,
(3-F-phenyl)-NH—, (3-Cl-phenyl)-NH—,
(3-CF₃-phenyl)-NH—, (3-CH₃-phenyl)-NH—,
(3-OMe-phenyl)-NH—, (3-CN-phenyl)-NH—,
(3-OCF₃-phenyl)-NH—, (3-SMe-phenyl)-NH—,
(4-F-phenyl)-NH—, (4-Cl-phenyl)-NH—,
(4-CF₃-phenyl)-NH—, (4-CH₃-phenyl)-NH—,
(4-OMe-phenyl)-NH—, (4-CN-phenyl)-NH—,
(4-OCF₃-phenyl)-NH—, (4-SMe-phenyl)-NH—,
(2,3-diCl-phenyl)-NH—, (2,4-diCl-phenyl)-NH—,
(2,5-diCl-phenyl)-NH—, (2,6-diCl-phenyl)-NH—,
(3,4-diCl-phenyl)-NH—, (3,5-diCl-phenyl)-NH—,
(2,3-diF-phenyl)—NH—, (2,4-diF-phenyl)-NH—,
(2,5-diF-phenyl)-NH—, (2,6-diF-phenyl)-NH—,
(3,4-diF-phenyl)-NH—, (3,5-diF-phenyl)-NH—,
(2,3-diCH₃-phenyl)-NH—, (2,4-diCH₃-phenyl)-NH—,
(2,5-diCH₃-phenyl)-NH—, (2,6-diCH₃-phenyl)-NH—,
(3,4-diCH₃-phenyl)-NH—, (3,5-diCH₃-phenyl)-NH—,
(2,3-diCF₃-phenyl)-NH—, (2,4-diCF₃-phenyl)-NH—,
(2,5-diCF₃-phenyl)-NH—, (2,6-diCF₃-phenyl)-NH—,
(3,4-diCF₃-phenyl)-NH—, (3,5-diCF₃-phenyl)-NH-,
(2,3-diOMe-phenyl)-NH—, (2,4-diOMe-phenyl)-NH—,
(2,5-diOMe-phenyl)-NH—, (2,6-dioMe-phenyl)-NH—,
(3,4-dioMe-phenyl)-NH—, (3,5-dioMe-phenyl)-NH—,
(2-F-3-Cl-phenyl)-NH—, (2-F-4-Cl-phenyl)-NH—,
(2-F-5-Cl-phenyl)-NH—, (2-F-6-Cl-phenyl)-NH—,
(2-F-3-CH₃-phenyl)-NH—, (2-F-4-CH₃-phenyl)-NH—,
(2-F-5-CH₃-phenyl)-NH—, (2-F-6-CH₃-phenyl)-NH—,
(2-F-3-CF₃-phenyl)-NH—, (2-F-4-CF₃-phenyl)-NH—,
(2-F-5-CF₃-phenyl)-NH—, (2-F-6-CF₃-phenyl)-NH—,
(2-F-3-OMe-phenyl)-NH—, (2-F-4-OMe-phenyl)-NH—,
(2-F-5-OMe-phenyl)-NH—, (2-F-6-OMe-phenyl)-NH—,
(2-Cl-3-F-phenyl)-NH—, (2-Cl-4-F-phenyl)-NH—,
(2-Cl-5-F-phenyl)-NH—, (2-Cl-6-F-phenyl)-NH—,
(2-Cl-3-CH₃-phenyl)-NH—, (2-Cl-4-CH₃-phenyl)-NH—,
(2-Cl-5-CH₃-phenyl)-NH—, (2-Cl-6-CH₃-phenyl)-NH—,
(2-Cl-3-CF₃-phenyl)-NH—, (2-Cl-4-CF₃-phenyl)-NH—,
(2-Cl-5-CF₃-phenyl)-NH—, (2-Cl-6-CF₃-phenyl)-NH—,
(2-Cl-3-OMe-phenyl)-NH—, (2-Cl-4-OMe-phenyl)-NH—,
(2-Cl-5-OMe-phenyl)-NH—, (2-Cl-6-OMe-phenyl)-NH—,
(2-CH₃-3-F-phenyl)-NH—, (2-CH₃-4-F-phenyl)-NH—,
(2-CH₃-5-F-phenyl)-NH—, (2-CH₃-6-F-phenyl)-NH—,
(2-CH₃-3-Cl-phenyl)-NH—, (2-CH₃-4-Cl-phenyl)-NH—,
(2-CH₃-5-Cl-phenyl)-NH—, (2-CH₃-6-Cl-phenyl)-NH—,
(2-CH₃-3-CF₃-phenyl)-NH—, (2-CH₃-4-CF₃-phenyl)-NH—,
(2-CH₃-5-CF₃-phenyl)-NH—, (2-CH₃-6-CF₃-phenyl)-NH—,
(2-CH₃-3-OMe-phenyl)-NH—, (2-CH₃-4-OMe-phenyl)-NH—,
(2-CH₃-5-OMe-phenyl)-NH—, (2-CH₃-6-OMe-phenyl)-NH—,
(2-CF₃-3-F-phenyl)-NH—, (2-CF₃-4-F-phenyl)-NH—, (2-CF$_3$-5-F-phenyl)-NH—, (2-CF$_3$-6-F-phenyl)-NH—,
(2-CF$_3$-3-Cl-phenyl)-NH—, (2-CF$_3$-4-Cl-phenyl)-NH—,
(2-CF$_3$-5-Cl-phenyl)-NH—, (2-CF$_3$-6-Cl-phenyl)-NH—,
(2-CF$_3$-3-CH$_3$-phenyl)-NH—, (2-CF$_3$-4-CH$_3$-phenyl)-NH—,
(2-CH$_3$-5-CF$_3$-phenyl)-NH—, (2-CF$_3$-6-CH$_3$-phenyl)-NH—,
(2-CF$_3$-3-OMe-phenyl)-NH—, (2-CF$_3$-4-OMe-phenyl)-NH—,
(2-CF$_3$-5-OMe-phenyl)-NH—, (2-CF$_3$-6-OMe-phenyl)-NH—,
(2-OMe-3-F-phenyl)-NH—, (2-OMe-4-F-phenyl)-NH—,
(2-OMe-5-F-phenyl)-NH—, (2-OMe-6-F-phenyl)-NH—,
(2-OMe-3-Cl-phenyl)-NH—, (2-OMe-4-Cl-phenyl)-NH—,
(2-OMe-5-Cl-phenyl)-NH—, (2-OMe-6-Cl-phenyl)-NH—,
(2-OMe-3-CH$_3$-phenyl)-NH—, (2-OMe-4-CH$_3$-phenyl)-NH—,
(2-OMe-5-CH$_3$-phenyl)-NH—, (2-OMe-6-CH$_3$-phenyl)-NH—,
(2-OMe-3-CF$_3$-phenyl)-NH—, (2-OMe-4-CF$_3$-phenyl)-NH—,
(2-OMe-5-CF$_3$-phenyl)-NH—, (2-OMe-6-CF$_3$-phenyl)-NH—
(3-CF$_3$-4-Cl-phenyl)-NH—, (3-CF$_3$-4-C(O)CH$_3$-phenyl)-NH—,
(2,3,5-triCl-phenyl)-NH—, (3-CH$_3$-4-CO$_2$Me-phenyl)-NH—, and
(3-CHO-4-OMe-phenyl)-NH—; and
R$^9$ is selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy.

5. A compound of claim 1 of formula (I-a)

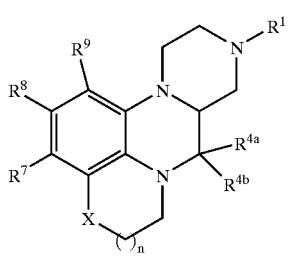

(I-a)

wherein:
X is a bond —CH$_2$—, —O—, —S—, —S(=O)—, —S(=O)$_2$—, —NR$^{10}$—, —CH$_2$CH$_2$—, —OCH$_2$—, —SCH$_2$—, —CH$_2$O—, —CH$_2$S—, —NR$^{10}$CH$_2$—, or —CH$_2$NR$^{10}$—;
n is 1 or 2;
R$^1$ is selected from
H,
C(=O)R$^2$,
C(=O)OR$^2$,
C$_{1-8}$ alkyl,
C$_{2-8}$ alkenyl,
C$_{2-8}$ alkynyl,
C$_{3-7}$ cycloalkyl,
C$_{1-6}$ alkyl substituted with 0–2 R$^2$,
C$_{2-6}$ alkenyl substituted with 0–2 R$^2$,
C$_{2-6}$ alkynyl substituted with 0–2 R$^2$,
aryl substituted with 0–2 R$^2$, and
5–6 membered heterocyclic ring system containing at least one heteroatom selected from the group consisting of N, O, and S, said heterocyclic ring system substituted with 0–2 R$^2$;
R$^2$, at each occurrence, is independently selected from
F, Cl, CH$_2$F, CHF$_2$, CF$_3$,
C$_{1-4}$ alkyl,
C$_{2-4}$ alkenyl,
C$_{2-4}$ alkynyl,
C$_{3-6}$ cycloalkyl,
phenyl substituted with 0–5 R$^{42}$;
C$_{3-10}$ carbocyclic residue substituted with 0–3 R$^{41}$, and
5–10 membered heterocyclic ring system containing from 1–4 heteroatoms selected from the group consisting of N, O, and S substituted with 0–3 R$^{41}$;
R$^{4a}$ is H or C$_{1-4}$ alkyl;
R$^{4b}$ is H;
alternatively, R$^{4a}$ and R$^{4b}$ are taken together to form =O or =S;
R$^7$ and R$^9$, at each occurrence, are independently selected from
H, halo, —CF$_3$, —OCF$_3$, —OH, —CN, —NO$_2$, —NR$^{46}$R$^{47}$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{3-10}$ cycloalkyl substituted with 0–2 R$^{33}$,
C$_{1-4}$ alkyl substituted with 0–2 R$^{11}$,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$,
NR$^{14}$C(O)R$^{12}$, C(O)OR$^{12}$, OC(O)R$^{12}$, OC(O)OR$^{12}$,
CH(=NR$^{14}$)NR$^{12}$R$^{13}$, NHC(=NR$^{14}$)NR$^{12}$R$^{13}$, S(O)R$^{12}$, S(O)$_2$R$^{12}$,
S(O)NR$^{12}$R$^{13}$, S(O)$_2$NR$^{12}$R$^{13}$, NR$^{14}$S(O)R$^{12}$, NR$^{14}$S(O)$_2$R$^{12}$,
NR$^{12}$C(O)R$^{15}$, NR$^{12}$C(O)OR$^{15}$, NR$^{12}$S(O)$_2$R$^{15}$, and NR$^{12}$C(O)NHR$^{15}$;
R$^8$ is selected from
H, halo, —CF$_3$, —OCF$_3$, —OH, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{3-10}$ cycloalkyl substituted with 0–2 R$^{33}$,
C$_{1-4}$ alkyl substituted with 0–2 R$^{11}$,
C$_{2-4}$ alkenyl substituted with 0–2 R$^{11}$,
C$_{2-4}$ alkynyl substituted with 0–1 R$^{11}$,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$,
NR$^{14}$C(O)R$^{12}$, C(O)OR$^{12}$, OC(O)R$^{12}$, OC(O)OR$^{12}$,
CH(=NR$^{14}$)NR$^{12}$R$^{13}$, NHC(=NR$^{14}$)NR$^{12}$R$^{13}$, S(O)R$_2$R$^{12}$,
S(O)NR$^{12}$R$^{13}$, S(O)$_2$NR$^{12}$R$^{13}$, NR$^{14}$S(O)R$^{12}$, NR$^{14}$S(O)$_2$R$^{12}$,
NR$^{12}$C(O)R$^{15}$, NR$^{12}$C(O)OR$^{15}$, NR$^{12}$S(O)$_2$R$^{15}$, and

NR$^{12}$C(O)NHR$^{15}$;

R$^{10}$ is selected from H, C$_{1-4}$ alkyl, C$_{2-4}$ alkenyl, C$_{2-4}$ alkynyl, and C$_{1-4}$ alkoxy;

R$^{11}$ is selected from
- H, halo, —CF$_3$, —CN, —NO$_2$,
- C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
- C$_{3-10}$ carbocyclic residue substituted with 0–3 R$^{33}$,
- aryl substituted with 0–5 R$^{33}$,
- 5–10 membered heterocyclic ring system containing from 1–4 heteroatoms selected from the group consisting of N, O, and S substituted with 0–3 R$^{31}$;
- OR$^{12}$, SR$^{12}$, NR$^{12}$R$^{13}$, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{13}$, S(O)$_2$R$^{12}$,
- S(O)NR$^{12}$R$^{13}$, S(O)$_2$NR$^{12}$R$^{13}$, NR$^{14}$S(O)R$^{12}$, NR$^{14}$S(O)$_2$R$^{12}$,
- NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{12}$, at each occurrence, is independently selected from
- C$_{1-4}$ alkyl substituted with 0–1 R$^{12a}$,
- C$_{2-4}$ alkenyl substituted with 0–1 R$^{12a}$,
- C$_{2-4}$ alkynyl substituted with 0–1 R$^{12a}$,
- C$_{3-6}$ cycloalkyl substituted with 0–3 R$^{33}$,
- aryl substituted with 0–5 R$^{33}$;
- C$_{3-10}$ carbocyclic residue substituted with 0–3 R$^{33}$, and
- 5–10 membered heterocyclic ring system containing from 1–4 heteroatoms selected from the group consisting of N, O, and S substituted with 0–3 R$^{31}$;

R$^{12a}$, at each occurrence, is independently selected from
- phenyl substituted with 0–5 R$^{33}$;
- C$_{3-10}$ carbocyclic residue substituted with 0–3 R$^{33}$, and
- 5–10 membered heterocyclic ring system containing from 1–4 heteroatoms selected from the group consisting of N, O, and S substituted with 0–3 R$^{31}$;

R$^{13}$, at each occurrence, is independently selected from H, C$_{1-4}$ alkyl, C$_{2-4}$ alkenyl, and C$_{2-4}$ alkynyl;

alternatively, R$^{12}$ and R$^{13}$ join to form a 5- or 6-membered ring optionally substituted with —O— or —N(R$^{14}$)—;

alternatively, R$^{12}$ and R$^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 R$^{16}$;

R$^{14}$, at each occurrence, is independently selected from H and C$_{1-4}$ alkyl;

R$^{15}$, at each occurrence, is independently selected from H, C$_{1-4}$ alkyl, C$_{2-4}$ alkenyl, and C$_{2-4}$ alkynyl;

R$^{16}$, at each occurrence, is independently selected from H, OH, halo, CN, NO$_2$, CF$_3$, SO$_2$R$^{45}$, NR$^{46}$R$^{47}$, —C(=O)H, C$_{1-4}$ alkyl, C$_{2-4}$ alkenyl, C$_{2-4}$ alkynyl, C$_{1-4}$ haloalkyl, C$_{1-3}$ haloalkyl-oxy-, and C$_{1-3}$ alkyloxy-;

R$^{31}$, at each occurrence, is independently selected from H, OH, halo, CF$_3$, SO$_2$R$^{45}$, NR$^{46}$R$^{47}$, and C$_{1-4}$ alkyl;

R$^{33}$, at each occurrence, is independently selected from H, OH, halo, CN, NO$_2$, CF$_3$, SO$_2$R$^{45}$, NR$^{46}$R$^{47}$, —C(=O)H,
- phenyl, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyl-oxy-, C$_{1-4}$ alkyloxy-, C$_{1-4}$ alkylthio-, C$_{1-4}$ alkyl-C(=O)—, C$_{1-4}$ alkyl-C(=O)NH—, C$_{1-4}$ alkyl-OC(=O)—, C$_{1-4}$ alkyl-C(=O)O—, C$_{3-6}$ cycloalkyl-oxy-, C$_{3-6}$ cycloalkylmethyl-oxy-;
- C$_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—; and
- C$_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—;

R$^{41}$, at each occurrence, is independently selected from H, CF$_3$, halo, OH, CO$_2$H, SO$_2$R$^{45}$, NR$^{46}$R$^{47}$, NO$_2$, CN;
- C$_{2-8}$ alkenyl, C$_{2-8}$ alkynyl, C$_{1-4}$ alkoxy, C$_{1-4}$ haloalkyl
- C$_{1-4}$ alkyl substituted with 0–1 R$^{43}$,
- aryl substituted with 0–3 R$^{42}$, and
- 5–10 membered heterocyclic ring system containing from 1–4 heteroatoms selected from the group consisting of N, O, and S substituted with 0–3 R$^{44}$;

R$^{42}$, at each occurrence, is independently selected from H, CF$_3$, halo, OH, CO$_2$H, SO$_2$R$^{45}$, NR$^{46}$R$^{47}$, NO$_2$, CN, CH(=NH)NH$_2$, NHC(=NH)NH$_2$,
- C$_{2-6}$ alkenyl, C$_{2-6}$ alkynyl, C$_{1-4}$ alkoxy, C$_{1-4}$ haloalkyl, C$_{3-6}$ cycloalkyl,
- C$_{1-4}$ alkyl substituted with 0–1 R$^{43}$,
- aryl substituted with 0–3 R$^{44}$, and
- 5–10 membered heterocyclic ring system containing from 1–4 heteroatoms selected from the group consisting of N, O, and S substituted with 0–3 R$^{44}$;

R$^{43}$ is C$_{3-6}$ cycloalkyl or aryl substituted with 0–3 R$^{44}$;

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, C$_{1-4}$ alkyl, and C$_{1-4}$ alkoxy;

R$^{45}$ is C$_{1-4}$ alkyl;

R$^{46}$, at each occurrence, is independently selected from H and C$_{1-4}$ alkyl; and R$^{47}$, at each occurrence, is independently selected from H and C$_{1-4}$ alkyl.

6. A compound of claim 5 of formula (I-b)

(I-b)

wherein:
X is —CH$_2$—, —O—, —S—, —CH$_2$CH$_2$—, —OCH$_2$—, —SCH$_2$—, —CH$_2$O—, or —CH$_2$S—;

R$^1$ is selected from
- H,
- C(=O)R$^2$,
- C(=O)OR$^2$,
- C$_{1-6}$ alkyl,
- C$_{2-6}$ alkenyl,
- C$_{2-6}$ alkynyl,
- C$_{3-6}$ cycloalkyl,
- C$_{1-4}$ alkyl substituted with 0–2 R$^2$,
- C$_{2-4}$ alkenyl substituted with 0–2 R$^2$, and
- C$_{2-4}$ alkynyl substituted with 0–2 R$^2$;

R$^2$, at each occurrence, is independently selected from
- C$_{1-4}$ alkyl,
- C$_{2-4}$ alkenyl,
- C$_{2-4}$ alkynyl,
- C$_{3-6}$ cycloalkyl, phenyl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^{4a}$ is H or $C_{1-4}$ alkyl;

$R^{4b}$ is H;

alternatively, $R^{4a}$ and $R^{4b}$ are taken together to form =O or =S;

$R^7$ and $R^9$, at each occurrence, are independently selected from
H, halo, —$CF_3$, —$OCF_3$, —OH, —CN, —$NO_2$, —$NR^{46}R^{47}$,
$C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, and $NR^{14}$S(O)$_2R^{12}$;

$R^8$ is selected from
H, halo, —$CF_3$, —$OCF_3$, —OH, —CN, —$NO_2$,
$C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$ $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$,
S(O)$NR^{12}R^{13}$, S(O)$_2NR^{12}R^{13}$, $NR^{14}$S(O)$R^{12}$, $NR^{14}$S(O)$_2R^{12}$,
$NR^{12}$C(O)$R^{15}$, $NR^{12}$C(O)$OR^{15}$, $NR^{12}$S(O)$_2Rl^{15}$, and $NR^{12}$C(O)$NHR^{15}$;

$R^{11}$ is selected from
H, halo, —$CF_3$, —CN, —$NO_2$, $C_{1-6}$ alkyl,
$C_{2-6}$ alkenyl, $C_{2-6}$ alkynyl, $C_{1-4}$ haloalkyl, $C_{1-6}$ alkoxy, $C_{3-10}$ cycloalkyl,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, and $NR^{14}$S(O)$_2R^{12}$;

$R^{12}$, at each occurrence, is independently selected from
$C_{14}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$ and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H, methyl, ethyl, propyl, and butyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, F, Cl, CN, $NO_2$, $CF_3$, $SO_2R^{45}$, $NR^{46}R^{47}$, —C(=O)H, methyl, ethyl, methoxy, ethoxy, trifluoromethyl, and trifluoromethoxy;

$R^{31}$, at each occurrence, is independently selected from H, OH, halo, $CF_3$, $SO_2R^{45}$, $NR^{46}R^{47}$, and $C_{1-4}$ alkyl;

$R^{33}$, at each occurrence, is independently selected from
H, OH, halo, CN, $N_2$, $CF_3$, $SO_2R^{45}$, $NR^{46}R^{47}$, —C(=O)H,
phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl—OC(=O)—, $C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl) $CO_2$—; and
$C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C^{1-4}$ alkyl)$CO_2$—;

$R^{41}$, at each occurrence, is independently selected from H, $CF_3$, halo, OH, $CO_2$H, $SO_2R^{45}$, $NR^{46}R^{47}$, $NO_2$, CN, $C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2$H, $SO_2R^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl; and $R^{47}$, at each occurrence, is independently selected from H and $C_{1-4}$ alkyl.

7. A compound of claim 5 of formula (I-b):

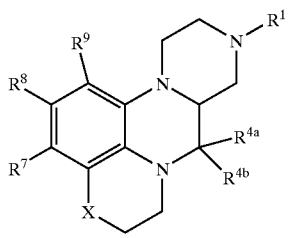

(I-b)

wherein:

X is —$CH_2$—, —O—, —S—, —$CH_2CH_2$—, —$OCH_2$—, or —$SCH_2$—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic residue substituted with 0–3 $R^{41}$, and
5–6 membered heterocyclic ring system containing 1, 2, or 3 heteroatoms selected from the group consisting of N, O, and S substituted with 0–3 $R^{41}$;

$R^{4a}$ is H, methyl, ethyl, propyl, or butyl;

$R^{4b}$ is H;

palternatively, $R^{4a}$ and $R^{4b}$ are taken together to form =O or =S;

$R^7$ and $R^{9,}$ at each occurrence, are independently selected from
H, halo, —$CF_3$, —$OCF_3$, —OH, —CN, —$NO_2$, —$NR^{46}R^{47}$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{33}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^8$ is selected from
H, halo, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R_{13}$ $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from H, OH, halo, CN, $NO_2$, $CF_3$, $SO_2R^{45}$, $NR^{46}R^{47}$, —C(=O)H,
phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—; and $C_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—;

R$^{41}$, at each occurrence, is independently selected from H, CF$_3$, halo, OH, CO$_2$H, SO$_2$R$^{45}$, NR$^{46}$R$^{47}$, NO$_2$, CN, $C_{2-4}$ alkenyl, $C_{2-4}$ alkynyl, $C_{1-3}$ alkoxy, $C_{1-3}$ haloalkyl, and $C_{1-3}$ alkyl;

R$^{42}$, at each occurrence, is independently selected from H, CF$_3$, halo, OH, CO$_2$H, SO$_2$R$^{45}$, NR$^{46}$R$^{47}$, NO$_2$, CN, CH(=NH)NH$_2$, NHC(=NH)NH$_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

R$^{43}$ is cyclopropyl, cyclobutyl, cyclopentyl, cyclohexyl, phenyl, or pyridyl, each substituted with 0–3 R$^{44}$;

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, methyl, ethyl, propyl, butyl, methoxy, ethoxy, propoxy, and butoxy;

R$^{45}$ is methyl, ethyl, propyl, or butyl;

R$^{46}$, at each occurrence, is independently selected from H, methyl, ethyl, propyl, and butyl; and R$^{47}$, at each occurrence, is independently selected from from H, methyl, ethyl, propyl, and butyl.

8. A compound of claim 7 wherein:

X is —CH$_2$—, —O— or —S—;

R$^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 R$^2$,
$C_{2-3}$ alkenyl substituted with 0–1 R$^2$, and
$C_{2-3}$ alkynyl substituted with 0–1 R$^2$;

R$^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 R$^{42}$;
$C_{3-6}$ carbocyclic residue substituted with 0–3 R$^{41}$, and
5–6 membered heterocyclic ring system containing 1, 2, or 3 heteroatoms selected from the group consisting of N, O, and S substituted with 0–3 R$^{41}$;

R$^{4a}$ is H;

R$^{4b}$ is H;

alternatively, R$^{4a}$ and R$^{4b}$ are taken together to form =O;

R$^7$ and R$^9$, at each occurrence, are independently selected from
H, F, Cl, —CH$_3$, —OCH$_3$, —CF$_3$, —OCF$_3$, —CN, and —NO$_2$, R$^8$ is selected from
H, F, Cl, Br, —CF$_3$, —OCF$_3$, —OH, —CN, —NO$_2$, $C_{1-4}$ alkyl, $C_{2-4}$ alkenyl, $C_{2-4}$ alkynyl, $C_{1-4}$ haloalkyl, $C_{1-4}$ alkoxy, (C$_{1-4}$ haloalkyl)oxy,
$C_{3-10}$ cycloalkyl substituted with 0–2 R$^{33}$,
$C_{1-4}$ alkyl substituted with 0–2 R$^{11}$,
$C_{2-4}$ alkenyl substituted with 0–2 R$^{11}$,
$C_{2-4}$ alkynyl substituted with 0–1 R$^{11}$,
$C_{3-10}$ carbocyclic residue substituted with 0–3 R$^{33}$,
aryl substituted with 0–5 R$^{33}$,
5–6 membered heterocyclic ring system containing 1, 2, or 3 heteroatoms selected from the group consisting of N, O, and S substituted with 0–3 R$^{31}$;
OR$^{12}$, SR$^{12}$, NR$^{12}$R$^{13}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{11}$ is selected from
H, halo, —CF$_3$, —CN, —NO$_2$,
$C_{1-4}$ alkyl, $C_{2-4}$ alkenyl, $C_{2-4}$ alkynyl, $C_{1-4}$ haloalkyl, $C_{1-4}$ alkoxy, (C$_{1-4}$ haloalkyl)oxy,
$C_{3-10}$ cycloalkyl substituted with 0–2 R$^{33}$,
$C_{3-10}$ carbocyclic residue substituted with 0–3 R$^{33}$,
aryl substituted with 0–5 R$^{33}$, and
5–6 membered heterocyclic ring system containing 1, 2, or 3 heteroatoms selected from the group consisting of N, O, and S substituted with 0–3 R$^{31}$;

R$^{12}$, at each occurrence, is independently selected from
$C_{1-4}$ alkyl substituted with 0–1 R$^{12a}$,
$C_{2-4}$ alkenyl substituted with 0–1 R$^{12a}$,
$C_{2-4}$ alkynyl substituted with 0–1 R$^{12a}$,
$C_{3-6}$ cycloalkyl substituted with 0–3 R$^{33}$,
aryl substituted with 0–5 R$^{33}$;
$C_{3-10}$ carbocyclic residue substituted with 0–3 R$^{33}$, and
5–10 membered heterocyclic ring system containing from 1–4 heteroatoms selected from the group consisting of N, O, and S substituted with 0–3 R$^{31}$;

R$^{12a}$, at each occurrence, is independently selected from
phenyl substituted with 0–5 R$^{33}$;
$C_{3-10}$ carbocyclic residue substituted with 0–3 R$^{33}$, and
5–10 membered heterocyclic ring system containing from 1–4 heteroatoms selected from the group consisting of N, O, and S substituted with 0–3 R$^{31}$;

R$^{13}$, at each occurrence, is independently selected from H, $C_{1-4}$ alkyl, $C_{2-4}$ alkenyl, and $C_{2-4}$ alkynyl;

alternatively, R$^{12}$ and R$^{13}$ join to form a 5- or 6-membered ring optionally substituted with —O— or —N(R$^{14}$)—;

alternatively, R$^{12}$ and R$^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 R$^{16}$;

R$^{14}$, at each occurrence, is independently selected from H, methyl, ethyl, propyl, and butyl;

R$^{15}$, at each occurrence, is independently selected from H, methyl, ethyl, propyl, and butyl;

R$^{16}$, at each occurrence, is independently selected from H, OH, F, Cl, CN, NO$_2$, methyl, ethyl, methoxy, ethoxy, trifluoromethyl, and trifluoromethoxy;

R$^{31}$, at each occurrence, is independently selected from H, OH, halo, CF$_3$, methyl, ethyl, and propyl;

R$^{33}$, at each occurrence, is independently selected from H, OH, halo, CN, NO$_2$, CF$_3$, SO$_2$R$^{45}$, NR$^{46}$R$^{47}$, —C(=O)H,
phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—; and $C_{2-6}$ alkenyl substituted with OH, methoxy, ethoxy, propoxy, butoxy, —$SO_2R^{45}$, —$NR^{46}R^{47}$, $NR^{46}R^{47}C$(=O)—, or ($C_{1-4}$ alkyl)$CO_2$—;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, $CF_3$, halo, OH, $CO_2H$, $SO_2R^{45}$, $NR^{46}R^{47}$, $NO_2$, CN, CH(=NH)$NH_2$, NHC(=NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl; and $R^{47}$, at each occurrence, is independently selected from from H, methyl, ethyl, propyl, and butyl.

9. A compound of claim 8 wherein:

X is —$CH_2$—, —O—, or —S—;

$R^1$ is selected from H,
 $C_{1-5}$ alkyl substituted with 0–1 $R^2$,
 $C_{2-5}$ alkenyl substituted with 0–1 $R^2$, and
 $C_{2-3}$ alkynyl substituted with 0–1 $R^2$;

$R^2$ is $C_{3-6}$ cycloalkyl;

$R^{4a}$ is H;

$R^{4b}$ is H;

$R^7$ and $R^9$, at each occurrence, are independently selected from H, F, Cl, —$CH_3$, —$OCH_3$, —$CF_3$, —$OCF_3$, —CN, and —$NO_2$;

$R^8$ is selected from $R^{11}$;
 methyl substituted with $R^{11}$;
 phenyl substituted with 0–2 $R^{33}$;
 $OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
 phenyl-substituted with 0–5 fluoro;
 naphthyl-substituted with 0–3 $R^{33}$;
 2-($H_3CCH_2C$(=O))-phenyl-substituted with $R^{33}$;
 2-($H_3CC$(=O))-phenyl-substituted with $R^{33}$;
 2-(HC(=O))-phenyl-substituted with $R^{33}$;
 2-($H_3CCH$(OH))-phenyl-substituted with $R^{33}$;
 2-($H_3CCH_2CH$(OH))-phenyl-substituted with $R^{33}$;
 2-($HOCH_2$)-phenyl-substituted with $R^{33}$;
 2-($HOCH_2CH_2$)-phenyl-substituted with $R^{33}$;
 2-($H_3COCH_2$)-phenyl-substituted with $R^{33}$;
 2-($H_3COCH_2CH_2$)-phenyl-substituted with $R^{33}$;
 2-($H_3CCH$(OMe))-phenyl-substituted with $R^{33}$;
 2-($H_3COC$(=O))-phenyl-substituted with $R^{33}$;
 2-($HOCH_2CH$=CH)-phenyl-substituted with $R^{33}$;
 2-((MeOC=O)CH=CH)-phenyl-substituted with $R^{33}$;
 2-(methyl)-phenyl-substituted with $R^{33}$;
 2-(ethyl)-phenyl-substituted with $R^{33}$;
 2-(i-propyl)-phenyl-substituted with $R^{33}$;
 2-($F_3C$)-phenyl-substituted with $R^{33}$;
 2-(NC)-phenyl-substituted with $R^{33}$;
 2-($H_3CO$)-phenyl-substituted with $R^{33}$;
 2-(fluoro)-phenyl-substituted with $R^{33}$;
 2-(chloro)-phenyl-substituted with $R^{33}$;
 3-(NC)-phenyl-substituted with $R^{33}$;
 3-($H_3CO$)-phenyl-substituted with $R^{33}$;
 3-(fluoro)-phenyl-substituted with $R^{33}$;
 3-(choro)-phenyl-substituted with $R^{33}$;
 4-(NC)-phenyl-substituted with $R^{33}$;
 4-(fluoro)-phenyl-substituted with $R^{33}$;
 4-(chloro)-phenyl-substituted with $R^{33}$;
 4-($H_3CS$)-phenyl-substituted with $R^{33}$;
 4-($H_3CO$)-phenyl-substituted with $R^{33}$;
 4-(ethoxy)-phenyl-substituted with $R^{33}$;
 4-(i-propoxy)-phenyl-substituted with $R^{33}$;
 4-(i-butoxy)-phenyl-substituted with $R^{33}$;
 4-($H_3CCH_2CH_2C$(=O))-phenyl-substituted with $R^{33}$;
 4-(($H_3C)_2CHC$(=O))-phenyl-substituted with $R^{33}$;
 4-($H_3CCH_2C$(=O))-phenyl-substituted with $R^{33}$;
 4-($H_3CC$(=O))-phenyl-substituted with $R^{33}$;
 4-($H_3CCH_2CH_2CH$(OH))-phenyl-substituted with $R^{33}$;
 4-(($H_3C)_2CHCH$(OH))-phenyl-substituted with $R^{33}$;
 4-($H_3CCH_2CH$(OH))-phenyl-substituted with $R^{33}$;
 4-($H_3CCH$(OH))-phenyl-substituted with $R^{33}$;
 4-(cyclopropyloxy)-phenyl-substituted with $R^{33}$;
 4-(cyclobutyloxy)-phenyl-substituted with $R^{33}$; and
 4-(cyclopentyloxy)-phenyl-substituted with $R^{33}$;

$R^{12}$ is selected from
 phenyl-substituted with 0–5 fluoro;
 naphthyl-substituted with 0–3 $R^{33}$;
 2-($H_3CCH_2C$(=O))-phenyl-substituted with $R^{33}$;
 2-($H_3CC$(=O))-phenyl-substituted with $R^{33}$;
 2-(HC(=O))-phenyl-substituted with $R^{33}$;
 2-($H_3CCH$(OH))-phenyl-substituted with $R^{33}$;
 2-($H_3CCH_2CH$(OH))-phenyl-substituted with $R^{33}$;
 2-($HOCH_2$)-phenyl-substituted with $R^{33}$;
 2-($HOCH_2CH_2$)-phenyl-substituted with $R^{33}$;
 2-($H_3COCH_2$)-phenyl-substituted with $R^{33}$;
 2-($H_3COCH_2CH_2$)-phenyl-substituted with $R^{33}$;
 2-($H_3CCH$(OMe))-phenyl-substituted with $R^{33}$;
 2-($H_3COC$(=O))-phenyl-substituted with $R^{33}$;
 2-($HOCH_2CH$=CH)-phenyl-substituted with $R^{33}$;
 2-((MeOC=O) CH=CH) -phenyl-substituted with R33;
 2-(methyl)-phenyl-substituted with $R^{33}$;
 2-(ethyl)-phenyl-substituted with $R^{33}$;
 2-(i-propyl)-phenyl-substituted with $R^{33}$;
 2-($F_3C$)-phenyl-substituted with $R^{33}$;
 2-(NC)-phenyl-substituted with $R^{33}$;
 2-($H_3CO$)-phenyl-substituted with $R^{33}$;
 2-(fluoro)-phenyl-substituted with $R^{33}$;
 2-(chloro)-phenyl-substituted with $R^{33}$;
 3-(NC)-phenyl-substituted with $R^{33}$;
 3-($H_3CO$)-phenyl-substituted with $R^{33}$;
 3-(fluoro)-phenyl-substituted with $R^{33}$;
 3-(chloro)-phenyl-substituted with $R^{33}$;
 4-(NC)-phenyl-substituted with $R^{33}$;
 4-(fluoro)-phenyl-substituted with $R^{33}$;
 4-(chloro)-phenyl-substituted with $R^{33}$;
 4-($H_3CS$)-phenyl-substituted with $R^{33}$;
 4-($H_3CO$)-phenyl-substituted with $R^{33}$;
 4-(ethoxy)-phenyl-substituted with $R^{33}$;
 4-(i-propoxy)-phenyl-substituted with $R^{33}$;
 4-(i-butoxy)-phenyl-substituted with $R^{33}$;
 4-($H_3CCH_2CH_2C$(=))-phenyl-substituted with $R^{33}$;
 4-(($H_3C)_2CHC$(=O))-phenyl -substituted with $R^{33}$;
 4-($H_3CCH_2C$)(=))-phenyl-substituted with $R^{33}$;
 4-($H_3CC$(=O))-phenyl-substituted with $R^{33}$;
 4-($H_3CCH_2CH_2CH$(OH))-phenyl-substituted with $R^{33}$;
 4-(($H_3C)_2CHCH$(OH))-phenyl-substituted with $R^{33}$;

4-($H_3CCH_2CH(OH)$))-phenyl-substituted with $R^{33}$;
4-($H_3CCH(OH)$)-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy; and $R^{33}$, at each occurrence, is independently selected from H, F, Cl, —$CH_3$, —$OCH_3$, —$CF_3$, —$OCF_3$, —CN, and —$NO_2$.

10. A compound of claim 5 of Formula (I-b):

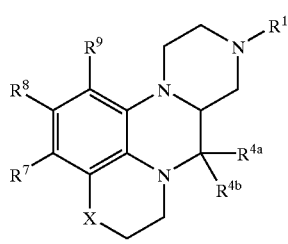

(I-b)

wherein:

$R^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, —CH=$CH_2$, —$CH_2$—CH=$CH_2$, —CH=CH—$CH_3$, —C≡CH, —C≡C—$CH_3$, and —$CH_2$—C≡CH;

$R^{4a}$ is H;

$R^{4b}$ is H;

alternatively, $R^{4a}$ and $R^{4b}$ are taken together to form =O;

$R^7$ and $R^9$, at each occurrence, are independently selected from hydrogen, fluoro, methyl, trifluoromethyl, and methoxy;

$R^8$ is selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl,
methylC(=O)—, ethylC(=O)—, propylC(=O)—, isopropylC(=O)—,
butylC(=O)—, phenylC(=O)—,
methyl$CO_2$—, ethyl$CO_2$—, propyl$CO_2$—, isopropyl$CO_2$—,
butyl$CO_2$—, phenyl$CO_2$—,
dimethylamino-S(=O)—, diethylamino-S(=O)—,
dipropylamino-S(=O)—, di-isopropylamino-S(=O)—,
dibutylamino-S(=O)—, diphenylamino-S(=O)—,
dimethylamino-$SO_2$—, diethylamino-$SO_2$—,
dipropylamino-$SO_2$—, di-isopropylamino-$SO_2$—,
dibutylamino-$SO_2$—, diphenylamino-$SO_2$—,
dimethylamino-C(=O)—, diethylamino-C(=O)—,
dipropylamino-C(=O)—, di-isopropylamino-C(=O)—,
dibutylamino-C(=O)—, diphenylamino-C(=O)—,
2-chlorophenyl, 2-fluorophenyl, 2-bromophenyl,
2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl,
3-cyanophenyl, 3-methylphenyl, 3-ethylphenyl,
3-propylphenyl, 3-isopropylphenyl, 3-butylphenyl,
3-trifluoromethylphenyl, 3-methoxyphenyl,
3-isopropoxyphenyl, 3-trifluoromethoxyphenyl,
3-thiomethoxyphenyl,
4-chlorophenyl, 4-fluorophenyl, 4-bromophenyl,
4-cyanophenyl, 4-methylphenyl, 4-ethylphenyl,
4-propylphenyl, 4-isopropylphenyl, 4-butylphenyl,
4-trifluoromethylphenyl, 4-methoxyphenyl,
4-isopropoxyphenyl, 4-trifluoromethoxyphenyl,
4-thiomethoxyphenyl,
2,3-dichlorophenyl, 2,3-difluorophenyl,
2,3-dimethylphenyl, 2,3-ditrifluoromethylphenyl,
2,3-dimethoxyphenyl, 2,3-ditrifluoromethoxyphenyl,
2,4-dichlorophenyl, 2,4-difluorophenyl,
2,4-dimethylphenyl, 2,4-ditrifluoromethylphenyl,
2,4-dimethoxyphenyl, 2,4-ditrifluoromethoxyphenyl,
2,5-dichlorophenyl, 2,5-difluorophenyl,
2,5-dimethylphenyl, 2,5-ditrifluoromethylphenyl,
2,5-dimethoxyphenyl, 2,5-ditrifluoromethoxyphenyl,
2,6-dichlorophenyl, 2,6-difluorophenyl,
2,6-dimethylphenyl, 2,6-ditrifluoromethylphenyl,
2,6-dimethoxyphenyl, 2,6-ditrifluoromethoxyphenyl,
3,4-dichlorophenyl, 3,4-difluorophenyl,
3,4-dimethylphenyl, 3,4-ditrifluoromethylphenyl,
3,4-dimethoxyphenyl, 3,4-ditrifluoromethoxyphenyl,
2,4,6-trichlorophenyl, 2,4,6-trifluorophenyl,
2,4,6-trimethylphenyl, 2,4,6-tritrifluoromethylphenyl,
2,4,6-trimethoxyphenyl, 2,4,6-tritrifluoromethoxyphenyl,
2-chloro-4-$CF_3$-phenyl, 2-fluoro-3-chloro-phenyl,
2-chloro-4-$CF_3$-phenyl, 2-chloro-4-methoxy-phenyl,
2-methoxy-4-isopropyl-phenyl, 2-$CF_3$-4-methoxy-phenyl,
2-methyl-4-methoxy-5-fluoro-phenyl,
2-methyl-4-methoxy-phenyl, 2-chloro-4-$CF_3O$-phenyl,
2,4,5-trimethyl-phenyl, 2-methyl-4-chloro-phenyl,
methyl-C(=O)NH—, ethyl-C(=O)NH—, propyl-C(=O)NH—,
isopropyl-C(=O)NH—, butyl-C(=O)NH—, phenyl-C(=O)NH—,
4-acetylphenyl, 3-acetamidophenyl, 4-pyridyl, 2-furanyl,
2-thiophenyl, 2-naphthyl;

2-Me-5-F-phenyl, 2-F-5-Me-phenyl, 2-MeO-5-F-phenyl,
2-Me-3-Cl-phenyl, 3-NO$_2$-phenyl, 2-NO$_2$-phenyl,
2-Cl-3-Me-phenyl, 2-Me-4-EtO-phenyl, 2-Me-4-F-phenyl,
2-Cl-6-F-phenyl, 2-Cl-4-(CHF$_2$)O-phenyl,
2,4-diMeO-6-F-phenyl, 2-CF$_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-CF$_3$-4-EtO-phenyl, 2-CF$_3$-4-iPrO-phenyl,
2-CF$_3$-4-Cl-phenyl, 2-CF$_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH$_3$CH(OH)-4-MeO-phenyl,
2-CH$_3$CH(OH)-4-F-phenyl, 2-CH$_3$CH(OH)-4-Cl-phenyl,
2-CH$_3$CH(OH)-4-Me-phenyl, 2-CH$_3$CH(OMe)-4-MeO-phenyl,
2-CH$_3$C(=O)-4-MeO-phenyl, 2-CH$_3$C(=O)-4-F-phenyl,
2-CH$_3$C(=O)-4-Cl-phenyl, 2-CH$_3$C(=O)-4-Me-phenyl,
2-H$_2$C(OH)-4-MeO-phenyl, 2-H$_2$C(OMe)-4-MeO-phenyl,
2-H$_3$CCH$_2$CH(OH)-4-MeO-phenyl, 2-H$_3$CCH$_2$C(=O)-4-MeO-phenyl,
2-CH$_3$CO$_2$CH$_2$CH$_2$-4-MeO-phenyl,
(Z)-2-HOCH$_2$CH=CH-4-MeO-phenyl,
(E)-2-HOCH$_2$CH=CH-4-MeO-phenyl,
(Z)-2-CH$_3$CO$_2$CH=CH-4-MeO-phenyl,
(E)-2-CH$_3$CO$_2$CH=CH-4-MeO-phenyl,
2-CH$_3$OCH$_2$CH$_2$-4-MeO-phenyl,
2-F-4-MeO-phenyl, 2-Cl-4-F-phenyl,
(2-Cl-phenyl)-CH=CH—, (3-Cl-phenyl)—CH=CH—,
(2,6-diF-phenyl)-CH=CH—, —CH$_2$CH=CH$_2$,
phenyl-CH=CH—, (2-Me-4-MeO-phenyl)-CH=CH—,
cyclohexyl, cyclopentyl, cyclohexylmethyl,
EtCO$_2$CH$_2$CH$_2$—, EtCO$_2$CH$_2$CH$_2$CH$_2$—, EtCO$_2$CH$_2$CH$_2$CH$_2$CH$_2$—,
benzyl, 2-F-benzyl, 3-F-benzyl, 4-F-benzyl,
3-MeO-benzyl, 3-OH-benzyl, 2-MeO-benzyl,
2-OH-benzyl, 2-MeOC(=O)-3-MeO-phenyl,
2-Me-4-CN-phenyl, 2-Me-3-CN-phenyl,
2-Me-4-MeS-phenyl, 2-CF$_3$-4-CN-phenyl,
2-CHO-phenyl, 3-CHO-phenyl, 2-HOCH$_2$-phenyl,
3-HOCH$_2$-phenyl, 3-MeOCH$_2$-phenyl,
3-Me$_2$NCH$_2$-phenyl, 3-CN-4-F-phenyl,
2-Me-4-H$_2$NCO-phenyl, 2-Me-4-MeOC(=O)-phenyl,
3-H$_2$NCO-4-F-phenyl, 2-Me$_2$NCH$_2$-4-MeO-phenyl-,
2-Me-4-CH$_3$C(=O)-phenyl, phenyl-S—, Me$_2$N—,
1-pyrrolidinyl,
phenyl-NH—, benzyl-NH—, (1-naphthyl)-NH—,
(2-naphthyl)-NH—, (2-[1,1'-biphenyl])-NH—,
(3-[1,1'-biphenyl])-NH—, (4-[1,1'-biphenyl])-NH—,
(2-F-phenyl)-NH—, (2-Cl-phenyl)-NH—,
(2-CF$_3$-phenyl)-NH—, (2-CH$_3$-phenyl)-NH—,
(2-OMe-phenyl)-NH—, (2-CN-phenyl)-NH—,
(2-OCF$_3$-phenyl)-NH—, (2-SMe-phenyl)-NH—,
(3-F-phenyl)-NH—, (3-Cl-phenyl)-NH—,
(3-CF$_3$-phenyl)-NH—, (3-CH$_3$-phenyl)-NH—,
(3-OMe-phenyl)-NH—, (3-CN-phenyl)-NH—,
(3-OCF$_3$-phenyl)-NH—, (3-SMe-phenyl)-NH—,
(4-F-phenyl)-NH—, (4-Cl-phenyl)-NH—,
(4-CF$_3$-phenyl)-NH—, (4-CH$_3$-phenyl)-NH—,
(4-OMe-phenyl)-NH—, (4-CN-phenyl)-NH—,
(4-OCF$_3$-phenyl)-NH—, (4-SMe-phenyl)-NH—,
(2,3-diCl-phenyl)-NH—, (2,4-diCl-phenyl)-NH—,
(2,5-diCl-phenyl)-NH—, (2,6-diCl-phenyl)-NH—,
(3,4-diCl-phenyl)-NH—, (3,5-diCl-phenyl)-NH—,
(2,3-diF-phenyl)-NH—, (2,4-diF-phenyl)-N—,
(2,5-diF-phenyl)-NH—, (2,6-diF-phenyl)-NH—,
(3,4-diF-phenyl)-NH—, (3,5-diF-phenyl)-NH—,
(2,3-diCH$_3$-phenyl)-NH—, (2,4-diCH$_3$-phenyl)-NH—,
(2,5-diCH$_3$-phenyl)-NH—, (2,6-diCH$_3$-phenyl)-NH—,
(3,4-diCH$_3$-phenyl)-NH—, (3,5-diCH$_3$-phenyl)-NH—,
(2,3-diCF$_3$-phenyl)-NH—, (2,4-diCF$_3$-phenyl)-NH—,
(2,5-diCF$_3$-phenyl)-NH—, (2,6-diCF$_3$-phenyl)-NH—,
(3,4-diCF$_3$-phenyl)-NH—, (3,5-diCF$_3$-phenyl)-NH—,
(2,3-diOMe-phenyl)-NH—, (2,4-diOMe-phenyl)-NH—,
(2,5-diOMe-phenyl)-NH—, (2,6-diOMe-phenyl)-NH—,
(3,4-dioMe-phenyl)-NH—, (3,5-diOMe-phenyl)-NH—,
(2-F-3-Cl-phenyl)-NH—, (2-F-4-Cl-phenyl)-NH—,
(2-F-5-Cl-phenyl)-NH—, (2-F-6-Cl-phenyl)-NH—,
(2-F-3-CH$_3$-phenyl)-NH—, (2-F-4-CH$_3$-phenyl)-NH—,
(2-F-5-CH$_3$-phenyl)-NH—, (2-F-6-CH$_3$-phenyl)-NH—,
(2-F-3-CF$_3$-phenyl)-NH—, (2-F-4-CF$_3$-phenyl)-NH—,
(2-F-5-CF$_3$-phenyl)-NH—, (2-F-6-CF$_3$-phenyl)-NH—,
(2-F-3-OMe-phenyl)-NH—, (2-F-4-OMe-phenyl)-NH—,
(2-F-5-oMe-phenyl)-NH—, (2-F-6-OMe-phenyl)-NH—,
(2-Cl-3-F-phenyl)-NH—, (2-Cl-4-F-phenyl)-NH—,
(2-Cl-5-F-phenyl)-NH—, (2-Cl-6-F-phenyl)-NH—,
(2-Cl-3-CH$_3$-phenyl)-NH—, (2-Cl-4-CH$_3$-phenyl)-NH—,
(2-Cl-5-CH$_3$-phenyl)-NH—, (2-Cl-6-CH$_3$-phenyl)-NH—,
(2-Cl-3-CF$_3$-phenyl)-NH—, (2-Cl-4-CF$_3$-phenyl)-NH—,
(2-Cl-5-CF$_3$-phenyl)-NH—, (2-Cl-6-CF$_3$-phenyl)-NH—,
(2-Cl-3-OMe-phenyl)-NH—, (2-Cl-4-OMe-phenyl)-NH—,
(2-Cl-5-OMe-phenyl)-NH—, (2-Cl-6-OMe-phenyl)-NH—,
(2-CH$_3$-3-F-phenyl)-NH—, (2-CH$_3$-4-F-phenyl)-NH—,
(2-CH$_3$-5-F-phenyl)-NH—, (2-CH$_3$-6-F-phenyl)-NH—,
(2-CH$_3$-3-Cl-phenyl)-NH—, (2-CH$_3$-4-Cl-phenyl)-NH—,
(2-CH$_3$-5-Cl-phenyl)-NH—, (2-CH$_3$-6-Cl-phenyl)-NH—,
(2-CH$_3$-3-CF$_3$-phenyl)-NH—, (2-CH$_3$-4-CF$_3$-phenyl)-NH—,
(2-CH$_3$-5-CF$_3$-phenyl)-NH—, (2-CH$_3$-6-CF$_3$-phenyl)-NH—,
(2-CH$_3$-3-OMe-phenyl)-NH—, (2-CH$_3$-4-OMe-phenyl)-NH—,
(2-CH$_3$-5-OMe-phenyl)-NH—, (2-CH$_3$-6-OMe-phenyl)-NH—,
(2-CF$_3$-3-F-phenyl)-NH—, (2-CF$_3$-4-F-phenyl)-NH—, (2-CF$_3$-5-F-phenyl)-NH—, (2-CF$_3$-6-F-phenyl)-NH—,
(2-CF$_3$-3-Cl-phenyl)-NH—, (2-CF$_3$-4-Cl-phenyl)-NH—,
(2-CF$_3$-5-Cl-phenyl)-NH—, (2-CF$_3$-6-Cl-phenyl)-NH—,
(2-CF$_3$-3-CH$_3$-phenyl)-NH—, (2-CF$_3$-4-CH$_3$-phenyl)-NH—,
(2-CH$_3$-5-CF$_3$-phenyl)-NH—, (2-CF$_3$-6-CH$_3$-phenyl)-NH—,
(2-CF$_3$-3-OMe-phenyl)-NH—, (2-CF$_3$-4-OMe-phenyl)-NH—,
(2-CF$_3$-5-OMe-phenyl)-NH—, (2-CF$_3$-6-OMe-phenyl)-NH—,
(2-OMe-3-F-phenyl)-NH—, (2-OMe-4-F-phenyl)-NH—,
(2-OMe-5-F-phenyl)-NH—, (2-OMe-6-F-phenyl)-NH—,
(2-OMe-3-Cl-phenyl)-NH—, (2-OMe-4-Cl-phenyl)-NH—,
(2-OMe-5-Cl-phenyl)-NH—, (2-OMe-6-Cl-phenyl)-NH—,
(2-OMe-3-CH$_3$-phenyl)-NH—, (2-OMe-4-CH$_3$-phenyl)-NH—,
(2-OMe-5-CH$_3$-phenyl)-NH—, (2-OMe-6-CH$_3$-phenyl)-NH—,
(2-OMe-3-CF$_3$-phenyl)-NH—, (2-OMe-4-CF$_3$-phenyl)-NH—,
(2-OMe-5-CF$_3$-phenyl)-NH—, (2-OMe-6-CF$_3$-phenyl)-NH—
(3-CF$_3$-4-Cl-phenyl)-NH—, (3-CF$_3$-4-C(O)CH$_3$-phenyl)-NH—,
(2,3,5-triCl-phenyl)-NH—, (3-CH$_3$-4-CO$_2$Me-phenyl)-NH—, and
(3-CHO-4-OMe-phenyl)-NH—.

11. A compound of formula (I):

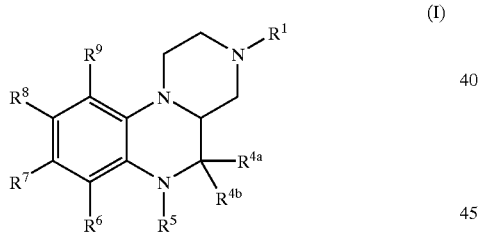

(I)

or a stereoisomer or a pharmaceutically acceptable salt form thereof, wherein:

$R^1$ is selected from
  $C_{1-6}$ alkyl substituted with Z,
  $C_{2-6}$ alkenyl substituted with Z,
  $C_{2-6}$ alkynyl substituted with Z,
  $C_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  $C_{1-6}$ alkyl substituted with 0–2 $R^2$,
  $C_{2-6}$ alkenyl substituted with 0–2 $R^2$,
  $C_{2-6}$ alkynyl substituted with 0–2 $R^2$,
  aryl substituted with 0–2 $R^2$, and
  5–6 membered heterocyclic ring system containing at least one heteroatom selected from the group consisting of N, O, and S, said heterocyclic ring system substituted with 0–2 $R^2$;

Z is selected from H,
  —CH(OH)$R^2$,
  —C(ethylenedioxy)$R^2$,
  —O$R^2$,
  —S$R^2$,
  —N$R^2R^3$,
  —C(O)$R^2$,
  —C(O)N$R^2R^3$,
  —N$R^3$C(O)$R^2$,
  —C(O)O$R^2$,
  —OC(O)$R^2$,
  —CH(=N$R^4$)N$R^2R^3$,
  —NHC(=N$R^4$)N$R^2R^3$,
  —S(O)$R^2$,
  —S(O)$_2R^2$,
  —S(O)$_2$N$R^2R^3$, and —N$R^3$S(O)$_2R^2$;

$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  aryl substituted with 0–5 $R^{42}$;
  $C_{3-10}$ carbocyclic residue substituted with 0–3 $R^{41}$, and
  5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H, methyl, ethyl, propyl, and butyl;

$R^{4a}$ is H or $C_{1-4}$ alkyl;

$R^{4b}$ is H;

alternatively, $R^{4a}$ and $R^{4b}$ are taken together to form =O or =S;

$R^5$ is H or $C_{1-4}$ alkyl;

$R^6$ is H or $C_{1-4}$ alkyl;

alternatively, $R^5$ and $R^6$ are taken together to form a fused heterocyclic ring of formula:

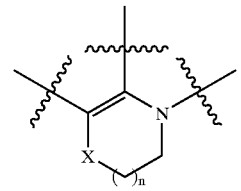

wherein:
X is a bond, —CH$_2$—, —O—, —S—, —S(=O)—, —S(=O)$_2$—, —NR$^{10}$—, —CH$_2$CH$_2$—, —OCH$_2$—, —SCH$_2$—, —CH$_2$O—, —CH$_2$S—, —CH$_2$NR$^{10}$—, —NR$^{10}$CH$_2$—, —NHC(=O)—, or —C(=O)NH—; and n is 1 or 2;

$R^7$, $R^8$, and $R^9$, at each occurrence, are independently selected from
  H, halo, —CF$_3$, —OCF$_3$, —OH, —CN, —NO$_2$, —NR$^{46}$R$^{47}$,
  $C_{1-8}$ alkyl, $C_{2-8}$ alkenyl, $C_{2-8}$ alkynyl, $C_{1-4}$ haloalkyl,
  $C_{1-8}$ alkoxy, ($C_{1-4}$ haloalkyl)oxy,
  $C_{1-4}$ alkyl substituted with 0–2 $R^{11}$,
  $C_{3-10}$ carbocyclic residue substituted with 0–3 $R^{33}$, aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$,
$NR^{14}C(O)R^{12}$, $C(O)OR^{12}$, $OC(O)R^{12}$, $OC(O)OR^{12}$,
$CH(=NR^{14})NR^{12}R^{13}$, $NHC(=NR^{14})NR^{12}R^{13}$, $S(O)R^{12}$, $S(O)_2R^{12}$,
$S(O)NR^{12}R^{13}$, $S(O)_2NR^{12}R^{13}$, $NR^{14}S(O)R^{12}$, $NR^{14}S(O)_2R^{12}$,
$NR^{12}C(O)R^{15}$, $NR^{12}C(O)OR^{15}$, $NR^{12}S(O)_2R^{15}$, and $NR^{12}C(O)NHR^{15}$;

$R^{10}$ is selected from H, $C_{1-4}$ alkyl, $C_{2-4}$ alkenyl, $C_{2-4}$ alkynyl, and $C_{1-4}$ alkoxy;

$R^{11}$ is selected from
H, halo, —$CF_3$, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$,
$CH(=NR^{14})NR^{12}R^{13}$, $NHC(=NR^{14})NR^{12}R^{13}$,
$S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^{12}$, at each occurrence, is independently selected from
$C_{1-4}$ alkyl,
$C_{2-4}$ alkenyl,
$C_{2-4}$ alkynyl,
$C_{3-6}$ cycloalkyl,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —$N(R^{14})$—;

$R^{14}$, at each occurrence, is independently selected from H and $C_{1-4}$ alkyl;

$R^{31}$, at each occurrence, is independently selected from H, OH, halo, $CF_3$, $SO_2R^{45}$, $NR^{46}R^{47}$, methyl, ethyl, and propyl;

$R^{33}$, at each occurrence, is independently selected from H, OH, halo, CN, $NO_2$, $CF_3$, $SO_2R^{45}$, $NR^{46}R^{47}$,
$C_{1-3}$ alkyl, $C_{2-3}$ alkenyl, $C_{2-3}$ alkynyl, $C_{3-5}$ cycloalkyl, $C_{1-3}$ haloalkyl, $C_{1-3}$ haloalkyl-oxy-, $C_{1-3}$ alkyloxy-, $C_{1-3}$ alkylthio-, $C_{1-3}$ alkyl-$C(=O)$—, and $C_{1-3}$ alkyl-$C(=O)NH$—;

$R^{41}$, at each occurrence, is independently selected from
H, $CF_3$, halo, OH, $CO_2H$, $SO_2R^{45}$, $NR^{46}R^{47}$, $NO_2$, CN, =O,
$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SR^{45}$, $NR^{46}R^{47}$, $OR^{48}$, $NO_2$, CN, $CH(=NH)NH_2$, $NHC(=NH)NH_2$, $C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —$C(=O)NH(C_{1-4}$ alkyl), —$SO_2(C_{1-4}$ alkyl), —$SO_2$(phenyl), —$C(=O)O(C_{1-4}$ alkyl), —$C(=O)$ ($C_{1-4}$ alkyl), and —$C(=O)H$; and $R^{48}$, at each occurrence, is independently selected from H, $C_{1-4}$ alkyl, —$C(=O)NH(C_{1-4}$ alkyl), —$C(=O)O(C_{1-4}$ alkyl), —$C(=O)$ ($C_{1-4}$ alkyl), and —$C(=O)H$; provided when $R^5$ is H or $C_{1-4}$ alkyl; and $R^6$ is H or $C_{1-4}$ alkyl; then $R^1$ is not $C_{1-6}$ alkyl.

12. A compound of claim 11 wherein:
$R^1$ is selected from
ethyl substituted with Z,
propyl substituted with Z,
butyl substituted with Z,
propenyl substituted with Z,
butenyl substituted with Z,
ethyl substituted with $R^2$,
propyl substituted with $R^2$,
butyl substituted with $R^2$,
propenyl substituted with $R^2$, and
butenyl substituted with $R^2$;

Z is selected from H,
—$CH(OH)R^2$,
—$OR^2$,
—$SR^2$,
—$NR^2R^3$,
—$C(O)R^2$,
—$C(O)NR^2R^3$,
—$NR^3C(O)R^2$,
—$C(O)OR^2$,
—$S(O)R^2$,
—$S(O)_2R^2$,
—$S(O)_2NR^2R^3$, and —$NR^3S(O)_2R^2$;

$R^2$, at each occurrence, is independently selected from
phenyl substituted with 0–3 $R^{42}$;
naphthyl substituted with 0–3 $R^{42}$;
cyclopropyl substituted with 0–3 $R^{41}$;
cyclobutyl substituted with 0–3 $R^{41}$;
cyclopentyl substituted with 0–3 $R^{41}$;
cyclohexyl substituted with 0–3 $R^{41}$;
pyridyl substituted with 0–3 $R^{41}$;
indolyl substituted with 0–3 $R^{41}$;
indolinyl substituted with 0–3 $R^{41}$;
benzimidazolyl substituted with 0–3 $R^{41}$;
benzotriazolyl substituted with 0–3 $R^{41}$;
benzothienyl substituted with 0–3 $R^{41}$;
benzofuranyl substituted with 0–3 R41;
phthalimid-1-yl substituted with 0–3 $R^{41}$;
inden-2-yl substituted with 0–3 $R^{41}$;
2,3-dihydro-1H-inden-2-yl substituted with 0–3 $R^{41}$;
indazolyl substituted with 0–3 $R^{41}$;
tetrahydroquinolinyl substituted with 0–3 R41; and tetrahydro-isoquinolinyl substituted with 0–3 $R^{41}$;

$R^3$, at each occurrence, is independently selected from H, methyl, and ethyl;

$R^{4a}$ is H or $C_{1-4}$ alkyl;

$R^{4b}$ is H;

alternatively, $R^{4a}$ and $R^{4b}$ are taken together to form =O;

$R^5$ is H or $C_{1-4}$ alkyl;

$R^6$ is H or $C_{1-4}$ alkyl;

alternatively, $R^5$ and $R^6$ are taken together to form a fused heterocyclic ring of formula:

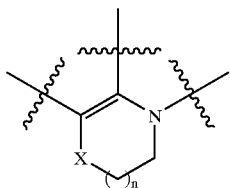

wherein:
X is —$CH_2$—, —O—, or —S—; and
n is 1;

$R^7$, $R^8$, and $R^9$, at each occurrence, are independently selected from H, F, Cl, methyl, ethyl, methoxy, —$CF_3$, and —$OCF_3$;

$R^{41}$ at each occurrence, is independently selected from H, F, Cl, Br, OH, $CF_3$, $NO_2$, CN, =O, methyl, ethyl, propyl, butyl, methoxy, and ethoxy;

$R^{42}$, at each occurrence, is independently selected from H, F, Cl, Br, OH, $CF_3$, $SO_2R^{45}$, $SR^{45}$, $NR^{46}R^{47}$ $OR_{48}$, $NO_2$, CN, =O, methyl, ethyl, propyl, butyl, methoxy, and ethoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —C(=O)NH(methyl), —C(=O)NH(ethyl), —$SO_2$(methyl), —$SO_2$(ethyl), —$SO_2$(phenyl), —C(=O)O(methyl), —C(=O)O(ethyl), —C(=O)(methyl), —C(=O)(ethyl), and —C(=O)H;

$R^{48}$, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H.

13. A compound of claim 11 wherein:
$R^1$ is selected from
—$(CH_2)_3C$(=O) (4-fluoro-phenyl),
—$(CH_2)_3C$(=O) (4-bromo-phenyl),
—$(CH_2)_3C$(=O) (4-methyl-phenyl),
—$(CH_2)_3C$(=O) (4-methoxy-phenyl),
—$(CH_2)_3C$(=O) (4-(3,4-dichloro-phenyl)phenyl),
—$(CH_2)_3C$(=O) (3-methyl-4-fluoro-phenyl),
—$(CH_2)_3C$(=O) (2,3-dimethoxy-phenyl),
—$(CH_2)_3C$(=O) (phenyl),
—$(CH_2)_3C$(=O) (4-chloro-phenyl),
—$(CH_2)_3C$(=O) (3-methyl-phenyl),
—$(CH_2)_3C$(=O) (4-t-butyl-phenyl),
—$(CH_2)_3C$(=O) (3,4-difluoro-phenyl),
—$(CH_2)_3C$(=O) (2-methoxy-5-fluoro-phenyl),
—$(CH_2)_3C$(=O) (4-fluoro-1-naphthyl),
—$(CH_2)_3C$(=O) (benzyl),
—$(CH_2)_3C$(=O) (4-pyridyl),
—$(CH_2)_3C$(=O) (3-pyridyl),
—$(CH_2)_3CH(OH)$ (4-fluoro-phenyl),
—$(CH_2)_3CH(OH)$ (4-pyridyl),
—$(CH_2)_3CH(OH)$ (2,3-dimethoxy-phenyl),
—$(CH_2)_3S$(3-fluoro-phenyl),
—$(CH_2)_3S$(4-fluoro-phenyl),
—$(CH_2)_3S$(=O) (4-fluoro-phenyl),
—$(CH_2)_3SO_2$(3-fluoro-phenyl),
—$(CH_2)_3SO_2$(4-fluoro-phenyl),
—$(CH_2)_3O$(4-fluoro-phenyl)
—$(CH_2)_3O$(phenyl),
—$(CH_2)_3O$(3-pyridyl),
—$(CH_2)_3O$(4-pyridyl),
—$(CH_2)_3O$(2-$NH_2$-phenyl),
—$(CH_2)_3O$(2-$NH_2$-5-F-phenyl),
—$(CH_2)_3O$(2-$NH_2$-4-F-phenyl),
—$(CH_2)_3O$(2-$NH_2$-3-F-phenyl),
—$(CH_2)_3O$(2-$NH_2$-4-Cl-phenyl),
—$(CH_2)_3O$(2-$NH_2$-4-OH-phenyl),
—$(CH_2)_3O$(2-$NH_2$-4-Br-phenyl),
—$(CH_2)_3O$(2-NHC(=O)Me-4-F-phenyl),
—$(CH_2)_3O$(2-NHC(=O) Me -phenyl),
—$(CH_2)_3NH$(4-fluoro-phenyl),
—$(CH_2)_3N$(methyl) (4-fluoro-phenyl),
—$(CH_2)_3CO_2$(ethyl),
—$(CH_2)_3C$(=O)N(methyl) (methoxy),
—$(CH_2)_3C$(=O)NH(4-fluoro-phenyl),
—$(CH_2)_2NHC$(=O) (phenyl),
—$(CH_2)_2NMeC$(=O) (phenyl),
—$(CH_2)_2NHC$(=O) (2-fluoro-phenyl),
—$(CH_2)_2NMeC$(=O) (2-fluoro-phenyl),
—$(CH_2)_2NHC$(=O) (4-fluoro-phenyl),
—$(CH_2)_2NMeC$(=O) (4-fluoro-phenyl),
—$(CH_2)_2NHC$(=O) (2,4-difluoro-phenyl),
—$(CH_2)_2NMeC$(=O) (2,4-difluoro-phenyl),
—$(CH_2)_3$(3-indolyl),
—$(CH_2)_3$(1-methyl-3-indolyl),
—$(CH_2)_3$(1-indolyl),
—$(CH_2)_3$(1-indolinyl),
—$(CH_2)_3$(1-benzimidazolyl),
—$(CH_2)_3$(1H-1,2,3-benzotriazol-1-yl),
—$(CH_2)_3$(1H-1,2,3-benzotriazol-2-yl),
—$(CH_2)_2$(1H-1,2,3-benzotriazol-1-yl),
—$(CH_2)_2$(1H-1,2,3-benzotriazol-2-yl),
—$(CH_2)_3$(3,4 dihydro-1(2H) -quinolinyl),
—$(CH_2)_2C$(=O) (4-fluoro-phenyl),
—$(CH_2)_2C$(=O)NH(4-fluoro-phenyl),
—$CH_2CH_2$(3-indolyl),
—$CH_2CH_2$(1-phthalimidyl),
—$(CH_2)_4C$(=O)N(methyl) (methoxy),
—$(CH_2)_4CO_2$(ethyl),
—$(CH_2)_4C$(=O) (phenyl),
—$(CH_2)_4$(cyclohexyl),
—$(CH_2)_3CH$(phenyl)$_2$,
—$CH_2CH_2CH$=C(phenyl)$_2$,
—$CH_2CH_2CH$=CMe(4-F-phenyl),
—$(CH_2)_3CH$(4-fluoro-phenyl)$_2$,
—$CH_2CH_2CH$=C(4-fluoro-phenyl)$_2$,
—$(CH_2)_2$(2,3-dihydro-1H-inden-2-yl),
—$(CH_2)_3C$(=O) (2-$NH_2$-phenyl),
—$(CH_2)_3C$(=O) (2-$NH_2$-5-F-phenyl),
—$(CH_2)_3C$(=O) (2-$NH_2$-4-F-phenyl),
—$(CH_2)_3C$(=O) (2-$NH_2$-3-F-phenyl),
—$(CH_2)_3C$(=O) (2-$NH_2$-4-Cl-phenyl),
—$(CH_2)_3C$(=O) (2-$NH_2$-4-OH-phenyl),
—$(CH_2)_3C$(=O) (2-$NH_2$-4-Br-phenyl),
—$(CH_2)_3$(1H-indazol-3-yl)

—(CH$_2$)$_3$(5-F-1H-indazol-3-yl),
—(CH$_2$)$_3$(7-F-1H-indazol-3-yl),
—(CH$_2$)$_3$(6-1H-indazol-3-yl),
—(CH$_2$)$_3$(6-Br-1H-indazol-3-yl),
—(CH$_2$)$_3$(=O) (2NHMe-phenyl),
—(CH$_2$)$_3$(1-benzothien-3-yl),
—(CH$_2$)$_3$(6-F-1H-indol-1-yl),
—(CH2)$_3$(5-F-1H-indol-1-yl),
—(CH$_2$)$_3$(6-F-2,3-dihydro-1H-indol-1-yl),
—(CH$_2$)$_3$(5-F-2,3-dihydro-1H-indol-1-yl),
—(CH$_2$)$_3$(6-F-1H-indol-3-yl),
—(CH$_2$)$_3$(5-F-1H-indol-3-yl),
—(CH$_2$)$_3$(5-F-1H-indol-3-yl),
—(CH$_2$)$_3$(9H-purin-9-yl),
—(CH$_2$)$_3$(7H-purin-7-yl),
—(CH$_2$)$_3$(6-F-1H-indazol-3-yl),
—(CH$_2$)$_3$C(=O) (2-NHSO$_2$Me-4-F-phenyl),
—(CH$_2$)$_3$C(=O) (2-NHC(=O)Me-4-F-phenyl),
—(CH$_2$)$_3$C(=O) (2-NHC(=O)Me-phenyl),
—(CH$_2$)$_3$C(=O) (2-NHCO$_2$Et-4-F-phenyl),
—(CH$_2$)$_3$C(=O) (2-NHC(=O)NHEt-4-F-phenyl),
—(CH$_2$)$_3$C(=O) (2-NHCHO-4-F-phenyl),
—(CH$_2$)$_3$C(=O) (2-OH-4-F-phenyl),
—(CH$_2$)$_3$C(=O) (2-MeS-4-F-phenyl),
—(CH$_2$)$_3$C(=O) (2-NHSO$_2$Me-4-F-phenyl),
—(CH$_2$)$_2$C(Me)CO$_2$Me,
—(CH$_2$)$_2$C(Me)CH(OH) (4-F-phenyl)$_2$,
—(CH$_2$)$_2$C(Me)CH(OH) (4-Cl-phenyl)$_2$,
—(CH$_2$)$_2$C(Me)C(=O) (4-F-phenyl),
—(CH$_2$)$_2$C(Me)C(=O) (2-MeO-4-F-phenyl),
—(CH$_2$)$_2$C(Me)C(=O) (3-Me-4-F-phenyl),
—(CH$_2$)$_2$C(Me)C(=O) (2-Me-phenyl),
—(CH$_2$)$_2$C(Me)C(=O)phenyl,

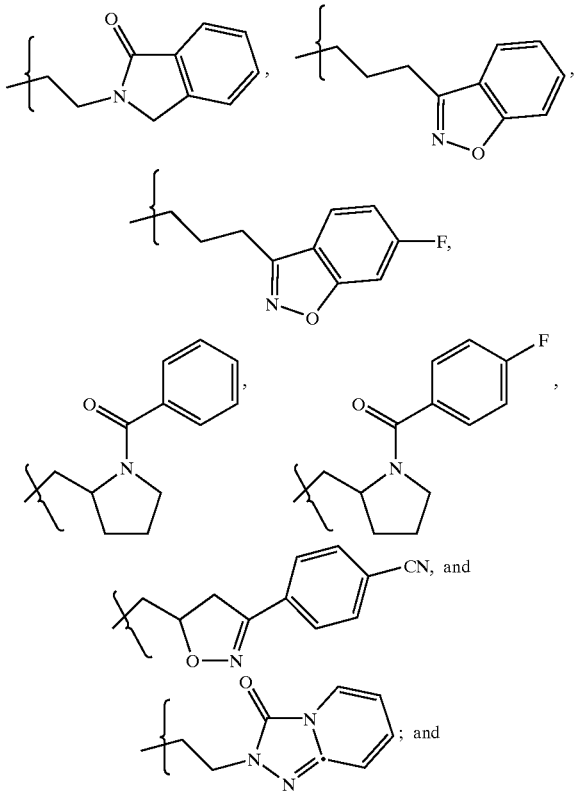

$R^{4a}$ is H;
$R^{4b}$ is H;

alternatively, $R^{4a}$ and $R^{4b}$ are taken together to form =O;
$R^5$ is H, methyl, ethyl, propyl, or butyl;
$R^6$ is H, methyl, ethyl, propyl, or butyl;
alternatively, $R^5$ and $R^6$ are taken together to form a fused heterocyclic ring of formula:

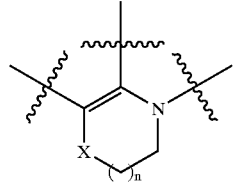

wherein:
X is —CH$_2$—, —O—, or —S—; and
n is 1;
$R^7$, $R^8$, and $R^9$, at each occurrence, are independently selected from
hydrogen, fluoro, chloro, bromo, cyano, methyl, ethyl, propyl, isopropyl, butyl, t-butyl, nitro,
trifluoromethyl, methoxy, ethoxy, isopropoxy,
trifluoromethoxy, phenyl, benzyl,
HC(=O)—, methylC(=O)—, ethylC(=O)—, propylC(=O)—,
isopropylC(=O)—, n-butylC(=O)—, isobutylC(=O)—,
secbutylC(=O)—, tertbutylC(=O)—, phenylC(=O)—,
methylC(=O)NH—, ethylC(=O)NH—, propylC(=O)NH—,
isopropylC(=O)NH—, n-butylC(=O)NH—, isobutylC(=O)NH—,
secbutylC(=O)NH—, tertbutylC(=O)NH—, phenylC(=O)NH—,
methylamino-, ethylamino-, propylamino-, isopropylamino-,
n-butylamino-, isobutylamino-, secbutylamino-, tertbutylamino-, phenylamino-,
provided that two of substituents $R^7$, $R^8$, and $R^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy.

14. A pharmaceutical composition comprising a pharmaceutically acceptable carrier and a therapeutically effective amount of a compound of claim 1, or a pharmaceutically acceptable salt thereof.

15. A pharmaceutical composition comprising a pharmaceutically acceptable carrier and a therapeutically effective amount of a compound of claim 11, or a pharmaceutically acceptable salt thereof.

16. A method for treating a human suffering from a disorder associated with 5HT2C receptor modulation comprising administering to a patient in need thereof a therapeutically effective amount of a compound of claim 1, or a pharmaceutically acceptable salt thereof.

17. A method of claim 16 for treating a human suffering from a disorder associated with 5HT2C receptor modulation wherein the compound is a 5HT2C agonist.

18. A method for treating a human suffering from a disorder associated with 5HT2A receptor modulation comprising administering to a patient in need thereof a therapeutically effective amount of a compound of claim 11, or a pharmaceutically acceptable salt thereof.

19. A method of claim 18 for treating a human suffering from a disorder associated with 5HT2A receptor modulation wherein the compound is a 5HT2A antagonist.

20. A method for treating obesity comprising administering to a patient in need thereof a therapeutically effective amount of a compound of claim 1, or a pharmaceutically acceptable salt thereof.

21. A method for treating schizophrenia comprising administering to a patient in need thereof a therapeutically effective amount of a compound of claim 11, or a pharmaceutically acceptable salt thereof.

22. A method for treating depression comprising administering to a patient in need thereof a therapeutically effective amount of a compound of claim 11, or a pharmaceutically acceptable salt thereof.

* * * * *